US009206458B2

(12) United States Patent
Calvo-Byrd et al.

(10) Patent No.: US 9,206,458 B2
(45) Date of Patent: *Dec. 8, 2015

(54) EFFECTS OF ALTERATION OF EXPRESSION OF THE MTFA GENE AND ITS HOMOLOGS ON THE PRODUCTION OF FUNGAL SECONDARY METABOLITES

(71) Applicant: BOARD OF TRUSTEES OF NORTHERN ILLINOIS UNIVERSITY, Dekalb, IL (US)

(72) Inventors: Ana M. Calvo-Byrd, Dekalb, IL (US); Vellaisamy Ramamoorthy, Dekalb, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/070,498

(22) Filed: Nov. 2, 2013

(65) Prior Publication Data

US 2014/0134671 A1    May 15, 2014

Related U.S. Application Data

(63) Continuation-in-part of application No. 14/070,094, filed on Nov. 1, 2013, now Pat. No. 8,927,255.

(60) Provisional application No. 61/721,777, filed on Nov. 2, 2012.

(51) Int. Cl.

| | |
|---|---|
| *C12P 21/02* | (2006.01) |
| *C12P 37/00* | (2006.01) |
| *C12N 1/14* | (2006.01) |
| *C12P 1/02* | (2006.01) |
| *C12P 7/66* | (2006.01) |
| *C12P 17/18* | (2006.01) |
| *C07K 14/37* | (2006.01) |

(52) U.S. Cl.
CPC ............ *C12P 37/00* (2013.01); *C07K 14/37* (2013.01); *C12N 1/14* (2013.01); *C12P 1/02* (2013.01); *C12P 7/66* (2013.01); *C12P 17/181* (2013.01)

(58) Field of Classification Search
None
See application file for complete search history.

(56) References Cited

PUBLICATIONS

Calvo, Fungal Genetics and Biology vol. 45 (2008) pp. 1053-1061.*
Barrios-Gonzalez et al., "Penicillin Production by Solid State Fermentation", *Biotechnology Letters*, 10(11): 793-798 (1988).
Brown et al., "Twenty-five coregulated transcripts define a sterigmatocystin gene cluster in Aspergillus nidulans", *Proc. Natl. Acad. Sci. USA*, 93: 1418-1422 (1996).
Calvo et al., "veA is Required for Toxin and Sclerotial Production in Aspergillus parasiticus", *Applied & Environmental Microbiology*, 70(8): 4733-4739 (2004).
Calvo, "The VeA regulatory system and its role in morphological and checmical development in fungi" *Fungal Genetics and Biology*, 45: 1053-1061 (2008).
Cole et al., *Handbook of Toxic Fungal Metabolites*, Academic Press, Chap. 1-2, 18 (1981).
Duran et al., "Production of cyclopiazonic acid, alfatrem, and aflatoxin by Aspergillus flavus is regulated by veA, a gene necessary for sclerotial formation", *Applied Microbiology and Biotechnology*, 73: 1158-1168 (2007).
Fernandez-Canon, "Overexpression of two penicillin structural genes in Aspergillus nidulans", *Molecular and General Genetics MGG*, 246(1): 110-118 (1995).
Käfer, "Meiotic and Mitotic Recombination in Aspergillus and its Chromosomal Aberrations," *Advance in Genetics*, vol. 19, Ed. E.W. Caspari, Academic Press, pp. 33-131 (1977).
Kato et al., "The Expression of Sterigmatocystin and Penicillin Genes in Aspergillus nidulans is Controlled by veA, a Gene Required for Sexual Development", *Eukaryotic Cell*, 2(6): 1178-1186 (2003).
Keil et al., "Overproduction of a single protein, Pc-Pex11p, results in 2-fold enhanced penicililin production by Penicillin chrysogenum", *Fungal Genetics and Biology*, 42: 154-164 (2005).
Keller et al., "Metabolic Pathway Gene Clusters in Filamentous Fungi", *Fungal Genetics and Biology*, 21: 17-29 (1997).
Kim et al., "The veA gene activates sexual development in Aspergillus nidulans", *Fungal Genetics and Biology*, 37: 72-80 (2002).
Miller et al., "Direct and indirect gene replacements in Aspergillus nidulans", *Molecular and Cellular Biology*, 5(7): 1714-1721 (1985).
Miller et al., "Position-dependent and -independent mechanisms regulate cell-specific expression of the SpoC1 gene cluster of Aspergillus nidulans", *Molecular and Cellular Biology*, 7(1): 427-434 (1987).
Myung et al., "FvVE1 Regulates Biosynthesis of Fumonisins and Fusarins in Fusarium verticillioides", *Journal of Agricultural and Food Chemistry*, 57: 5089-5094 (2009).
Osherov et al., "Conidial Germination in Aspergillus nidulans Requires RAS Signaling and Protein Synthesis", *Genetics*, 155: 647-656 (2000).
Pontecorvo, "The Genetics of Aspergillus nidulans", *Advances in Genetics*, 5: 141-238 (1953).
Ramamoorthy et al. "The Putative C2H2 Transcription Factor MtfA is a Novel Regulator of Secondary Metabolism and Morphogenesis in Aspergillus nidulans", *PLOS ONE*, 8(9): 1-16 (2013).
Ramamoorthy et al., "veA-dependent RNA-pol II transcription elongation factor-like protein, RtfA, is associated with secondary metabolism and morphological development in Aspergillus nidulans", *Molecular Microbiology*, 84(4): 795-814 (2012).
Sambrook et al., "Molecular Cloning, A Laboratory Manual," 3rd Ed., vol. 2, Chap. 1, 5-8 (2001).
Yelton et al., "Developmental regulation of the Aspergillus nidulans trpC gene", *Proceedings of the National Academy of Sciences*, 80: 7576-7580 (1983).
Yu et al., "Conservation of structure and function of the aflatoxin regulatory gene aflR from Aspergillus nidulans and A. flavus", *Current Genetics*, 29: 549-555 (1996).

* cited by examiner

*Primary Examiner* — Jim Ketter
(74) *Attorney, Agent, or Firm* — Barnes & Thornburg LLP; Alice O. Martin

(57) ABSTRACT

Many fungal secondary metabolites are of industrial interest, such as antibiotics, while others are undesirable compounds such as mycotoxins. Overexpression of mtfA enhances production of fungal compounds with applications in the medical field, and overexpression or impaired mtfA expression decreases the production of compounds that negatively affect health/agriculture/economy such as mycotoxins.

14 Claims, 34 Drawing Sheets

```
A.nidulans      1  MDEAN..QPGPE--PALTA.SR.SPPAFEPGSFYAAS--------------TS.T.T-
A.oryzae        1  MDEA...-PGPE--PIYKS.AS.SPPPSSAGSYKRPAEH--DSYF--------S.S.AP
A.niger         1  MDEA...HPGPD--PIMKS.AS.SPPMT--SYKRSIERTSDSYFPSVP---IS.T.SP
A.kawachii      1  MDEA...HPGPD--PIMKS.AS.SPPMT--SYKRSIEQTSDSYFPSVP---IS.T.SP
N.fischeri      1  MDEA...PSESDTVPTFRS.SIQNSSAS---HYKRLSEQYTGSYFSAAPTHTTS.S.TP
P.chrysogenum   1  MDSN...HSAAV------PI.TPVES-----------------------SY.K.S-
C.immitis       1  MNEG...CDQPH--QLRAPASS.SEHR---------RSPSIPKPLQTESSSCASP.S.FE
A.capsulatus    1  MNSI...SYHSP--PSTYP.SGTSQKRQ--SLQSESSLSVSNGYYDRNASN-LA.A.SP
U.reesii        1  MNSS...CDQTA--PFHGCATS.FEHHQ------RIRSPSIPKRSHEENSSSASP.PPFA
P.marneffei     1  MDNV--------------------------------------------------
B.fuckeliana    1  M-AS...NPYTV--HPMAQ.SS.--------------------------T.VNAP
N.tetrasperma   1  M-AP.T.-------PQYPAQP.--------------------------G.A---
N.crassa        1  M-AP...-------PQYPAQP.--------------------------G.A---
M.oryzae        1  M-AA...QQPYPI--RQQQSQ.--------------------------S.MVQP
C.globosum      1  M-AN...HYAHV---PQHSLQ-.--------------------------G.M---
F.oxysporum     1  M------------------------------------

A.nidulans     43
A.oryzae       48
A.niger        53
A.kawachii     53
N.fischeri     58
P.chrysogenum  29
C.immitis      51
A.capsulatus   56
U.reesii       54
P.marneffei     5
B.fuckeliana   28
N.tetrasperma  19
N.crassa       19
M.oryzae       26
C.globosum     23
F.oxysporum     2

A.nidulans     91  --------------------------LDKNPS-------.GAAPIR......
A.oryzae       95  --------------------------EFRSPY------DSVSTPNG......
A.niger       101  --------------------------DSRQQSQAYDLK.NGPQI......
A.kawachii    101  --------------------------DSRQQSQAYDLK.NCPQI......
N.fischeri    105  --------------------------GPPY------DSITPN......
P.chrysogenum  75  --------------------------SLGDRH------VRVQSYE......
C.immitis     100  ------------------GMERR----TIDQ------TLKQ.P.......
A.capsulatus  104  --------------------DLKSQGH-GATQKP------IHRP.M......
U.reesii      103  --------------------ALERR-GACADQ------IRQ.P.......
P.marneffei    12  ---------------------HDS------DY.GP.......
B.fuckeliana   74  ------------------KEDYRPESGH-QYGPSS------SMSS.G.....QS
N.tetrasperma  59  ----------------LHFSKPDNRPNSSQ----FGNP------.-SI.AN......SS
N.crassa       59  ----------------LHFSKPDNRPNSSQ---FGNP------.-SI.AN......SS
M.oryzae       73  --------------------AQQSRPNSSH--YSNA------VQSV.Q......TS
C.globosum     75  MSSSWWDMGHLDTDSTPAQGSRPETRPNSSH----YTNP------V-TI.T......SS
F.oxysporum    41  --------------------PPPSHGHSRAGSEW------.RSSHP......ST A.nidulans    113  G..HSAG.-S..SISMI-----KSE.PAP.S---------APVSLPG.P.P
A.oryzae      117  .SGLHSGL...SGKAI----KLE...M--------------T.P.P
A.niger       129  G..HSAG.A...AASDAAPKRSD..PQV.M---------------A.P.P
A.kawachii    129  G..HSAG.A...AASDAAPKRSD..PQV.M---------------A.P.P
N.fischeri    125  G..HSMG...AG..ATSSSAVMKNTE..SQA.I------------G.P.P
P.chrysogenum  97  G..HAHRRA..-VE..HKEAH-----------------------QHHL
C.immitis     125  ..MNSTSQ..ST..PPRSAIS-----LP.LVR.Y.SPVSE-----VPEGRRMSQ.SRH
A.capsulatus  133  G..LDGRN..AG..SAHSPISVANLT.SSSAL.SYQHR------MPQG----P.PPQ
U.reesii      130  ..MG.VR..SPSA..PPRTAIS-----LP.LIG.Y.SPVSE-----APEGRPMSQ.SRH
P.marneffei    31  C..TEG-S..ASLPSGRSHSA-----SI.SAV..SHQQRTSLFSISASLQNTP.-HP
B.fuckeliana  106  C..NR-Q..SQA.T..SYSVV-SAP-NYY.NP..QVSAIKN----MEPHAQRQP.Q.H
N.tetrasperma  92  .AS..Y-...SKPA.QSQGS----SNYY.ET..LSQ-------HEADSRQM--A.AA
N.crassa       92  .AS..Y-...SKPA.QSQGS----SNYY.ET..LSQ-------HEADSRQM--A.A.
```

```
B.fuckeliana    309  SFESASMV---------------------------------------
N.tetrasperma   286  SFESSNGRSSGNSNNGASA----------------------------
N.crassa        286  SFESSNGRSSGNSNNSASA----------------------------
M.oryzae        296  NYDSSSSNGTAMH----------------------------------
C.globosum      319  NYDSSSTTSSTGTMNSNTGGSRP------------------------
F.oxysporum     265  SFEFNGSVIRG------------------------------------
A.nidulans           -----------------------------------------------
A.oryzae             -----------------------------------------------
A.niger              -----------------------------------------------
A.kawachii           -----------------------------------------------
N.fischeri           -----------------------------------------------
P.chrysogenum        -----------------------------------------------
C.immitis            -----------------------------------------------
A.capsulatus         -----------------------------------------------
U.reesii        388  ESNGTLSPTKRRVKLAFSLDCQSTSSSRLALLFQSL
P.marneffei          -----------------------------------------------
B.fuckeliana         -----------------------------------------------
N.tetrasperma        -----------------------------------------------
N.crassa             -----------------------------------------------
M.oryzae             -----------------------------------------------
C.globosum           -----------------------------------------------
F.oxysporum          -----------------------------------------------
```

FIG. 11 (cont.)

```
A.nidulans      1   MDXANQPGPEPALTAKSRYSPPAFEPGSFYAA------S---------------T
A.oryzae        1   MDXAS-PGPEPIYKSRASYSPPPSSAGSYKRP------AE--------------HDSYF
A.niger         1   MDXASHPGPDPIMKSRASYSPPM---TSYKRS------IEHTSDSYFP--SV---PI
A.kawachii      1   MDXASHPGPDPIMKSRASYSPPM---TSYKRS------IEQTSDSYFP--SV---PI
N.fischeri      1   MDXAS-PSESDTVPTPRSRSIQNSSASHYKRL------SEQYTGSYPS--AAPTHT
P.chrysogenum   1   MDXSNHSAAVKPI-----YTP--------------------------V---ES
C.immitis       1   MNXSSCDQPHQLRAPASSYSEHR----------RSP---SIPKPLQT--ESSSCAS
A.capsulatus    1   MNXSHSYHSPPST-----YP---HSGTSQKRQSLQSESSLSVSNGYYD---RNASNL
U.reesii        1   MNXSSCDQTAPFHGSATSYFEHHQR--------IRSP---SIPKRSHE--ENSSSAS
P.marneffei     1   ----------------------------------------------------
B.fuckeliana    1   -MA---------------------------------SSLVSNPYTVHPMAQHSSY
N.tetrasperma   1   ----------------------------------MAPTTLTPQ--YPAQPY
N.crassa        1   ----------------------------------MAPTTLTPQ--YPAQPY
M.oryzae        1   -MA---------------------------------ATMIQQPYPIH--QQQSQY
C.globosum      1   -MA---------------------------------NTMVTHYAHVP--QHSLQY
F.oxysporum     1   ----------------------------------------------------

A.nidulans      38  XT-RTXARSSALXDSTQAP-------KRQRLSSPMH--
A.oryzae        42  SRAPXAQ-PEGADSTYAA-------KRQRTSPPPR--
A.niger         47  TRSPXPQSPEGAMHAA--------KRTRMTPPLQ--
A.kawachii      47  TRSPXPHSPEGAMHAA--------KRTRMTPPLQ--
N.fischeri      52  SRTPXPXLSPPAEDQ-PKCSLPSISLLENAAHA-------KRQRTSLSTH--
P.chrysogenum   23  -YKRSPXLSPPA--DKVFEGQHAATSLTINLPERQRLSPSLG--
C.immitis       45  PYSRFERLPLSPPXEDGKTQFRGVVSDAHV------AKRQRTNPPPS--
A.capsulatus    50  AMARSPQPQ-SXFQGADCLSPVHI-------AHRPNPLST--
U.reesii        48  PYPPFATLPLSPPEGKTTFQSVDTHV------AKRQRANPPPS--
P.marneffei     1   -------------------------MDNVPASKRA--------
B.fuckeliana    22  VNAPQPXPT-SGLSSPTEQAQQQSSPQQAAFKE-----
N.tetrasperma   16  GXAP----XPS-NKCSLPSISNXLVMADQPTSETSPQSQQLH----------
N.crassa        16  GXAP----XPS-NKCSLPSISNXLVMADQPTSETSPQSQQLH----------
M.oryzae        20  MVQPQGXP-D-NKCSLPSISNLLGLADQPTSETSAQYTPXAEATTRLLATG
C.globosum      20  GYMP----XPA-AKCSLPSISNXLGLADQPTSETSPQSQQQQAQQQQQQC
F.oxysporum     1   ------------MXE-QKCSLPSISNLLGLPTSESSPTSRQHSPRFEV-----

A.nidulans      88  -------------------RXPLDKNP-SA---------GAAPIRGSGFHSA
A.oryzae        92  -------------------RXSEFRSP-YDS---------VSTPNGHSG
A.niger         98  -------------------RXLDSRQQ-SQAY--DLKANGPQIGGSFHSA
A.kawachii      98  -------------------RXLDSRQQ-SQAY--DLKANGPQIGGSFHSA
N.fischeri      102 -------------------RX--SGPX-YDS--------ITPHGSGFHSN
P.chrysogenum   78  -------------------D--------------RHVRVQSYEGSGHAHR
C.immitis       97  -------------------IXLGMEXRT------IDQTLKQFPLMNST
A.capsulatus    101 ----------------GXVDLKSQGHGAT--QKPIHRPMIGSELDXR
U.reesii        100 -------------------IXLALEXRG--AC--ADQAIRQRPLMGGV
P.marneffei     11  -------------------RX--------DSGDYSRGFCSGFTEG
B.fuckeliana    76  -------------------DYEXGHQYGPSSSMSSRGQSXGFEDCR
N.tetrasperma   61  -------------------FSKPDNNXSQF--GNPA-SIRANSSXASFGY
N.crassa        61  -------------------FSKPDNNXSQF--GNPA-SIRANSSXASFGY
M.oryzae        78  ---KQATKGNNLAVILTSQTAAQQSNXSHY--SNAVQSVRQTSXSFDGY
C.globosum      75  MSSSWWDMGHLDTDSTPAQGSKPETXSHY--TNPV-TIRTSSXASFQF
F.oxysporum     41  ---------------------PPSXGHSRAG--SEWAKSSHRSTXASFGY A.nidulans      120 GHSPSS--------SISXISMIKSEYPA--PPSAPVS-LP----G-SPXRSSISQXS
A.oryzae        124 HHSPSA--------SSVXSGK----AIK--LESYSQT-PX---X-SPSDRSSISQXS
```

FIG. 24

```
A.niger        136 GHSPAS--------S-ISAASDAAAPKR--SDSYPQV-PM---A-SPSDRSSISSQ S
A.kawachii     136 GHSPAS--------S-ISAASDAAAPKR--SDSYPQV-PM---A-SPSDRSSISSQ S
N.fischeri     132 GHSPSA--------SSVSATSSSAVMKN--TETYSQA-PM---G-SPSDRSSISSQ S
P.chrysogenum  104 RASPVE--------SLSHKEAH----------------------QHHLHRSSISSNSS
C.immitis      132 SQSPSTSSPPRSAISLPSLVRSYPSEV----SEVPEGRRM---SQMSRHSRGASTSGTSQ
A.capsulatus   140 NHSPAGSSPSSAHSPISVANLT---SSSSADPSYQHRMPQ---GPPQSTNSP
U.reesii       137 NHSPSASSPPRTAISLPGLIGSYPSEV----SEAPEGRRY---SQMSRHSSSSQ
P.marneffei     38 SSPASLPSGRSHSASISSAVSHPSHQQRTSLPSISASLQN---S-PIHPSERLGISSLSS
B.fuckeliana   113 QSPSQASTSSYSVVSAPNYYFN-PSQVSAINNMEPHAQRQPVQ VTRRVSMPVSSMGY -
N.tetrasperma   99 RSPSSKPASQSQG---SNYYYETTPPLSQHEADSR--QM-A AAPRAPVQSSTFQTQ-
N.crassa        99 RSPSSKPASQSQG---SNYYYETTPPLSQHEADSR--QM-A ATPRAPVQSSTFQTQ-
M.oryzae       133 NSPSNKSVSQLPA---TGYYFEATPPGHME-MEPR--PH--M  RSRVPVQAPPA S-
C.globosum     132 NSPS RSVSQVPN---GSNYFFETTPPLQME-ADAR--QMTAAAAVSVQASAYQPQ-
F.oxysporum     78 SSPTRKPSNQAYPGSAPRTYYETTPPLEAD---AQ--RQASV AA PPA APYPQ- A.nidulans     165 APQ-HQHGPYASPAAPSS----PSSAMYYQHRPASSG  QAP--------
A.oryzae       165 VHH-VSAAPYASPAA-SSS----APSAM-YYQRP---SG  QTP--ATVPS
A.niger        180 VQG-VSSASYASPA-SS----ASSAMF-YQRT---------------APS
A.kawachii     180 VQG-VSSASYASPA-SS----ASSAMF-YQRT---------------APS
N.fischeri     177 VQH-AACAPYASPA- SS----TPS AAYYQRNP-APNQNP--GSFPP
P.chrysogenum  132 VHIPRNTVPYASPV-TAP----Q--QPMYYPREPTT-SQPSTPASAPQ
C.immitis      185 LSGPET--RYPSPPNVNSPS AAA----PKP EYYPASR--RVPPVA------
A.capsulatus   194 VSLPEKHYAPSSNLSSTP AL----ANSSE-YYPRES-HEPSTSIPLAAP-
U.reesii       190 HPGPEA--RYPSPTLSGP SAAP----PKPEYYSSGAR--PTNPPFVT------
P.marneffei     94 HDSSRL--SHAIPSPSS ---TASITTTA----TPS S-YYSTSE--EKAPPRSHSTSAPV
B.fuckeliana   171 HSPFNGSYTMSPGAQSYYP---QTQSPQV SLYYQRPL--PQQP PPM------
N.tetrasperma  151 ---YPSSAGYS-SQSG NPYYPPMQPTPPPQ-QQM GLYYQRPL--PQTPA--------
N.crassa       151 ---YPSSAGYS-SQSG NPYYPPMQPTPPPQ-QQM GLYYQRPL--PQTPA--------
M.oryzae       184 ---YSAPYGMA-PSNP AAY PSMQPTPPPQQPQI SLYYQRPL--PQAEP-P--------
C.globosum     185 ---YAPGPAYM-SQPA  SYPPMQSAAPPQ-TQM GLYYQRPL--PQPPP--------
F.oxysporum    132 ---QAHPTVYA-NPAP GAYYPAACVPPAV-QPQPMNPYYQRPL--PQA PPP-------

A.nidulans     213 --------------PPPPQHQP S-TPAWQHHHYFPPSSNTPYQQNHDRYICRTCHKAF
A.oryzae       213 PS------AAPMPASATHQQ T-TPYQQNHDRYICRTCHKAF
A.niger        219 TS------AAPLPTPAAPQQ S-NPAWQHHHYFPPSSTPYQQNHDRYICRTCHKAF
A.kawachii     219 TS------AAPLPTPAAPQQ S-NPAWQHHHYFPPSSTPYQQNHDRYICRTCHKAF
N.fischeri     228 TS------AASLP-SPGHQQ S-TTPYQQNHDRYICRTCHKAF
P.chrysogenum  184 MPPVQVQTQQPHSHSHSSSA S-TPYQQNHDRYICRTCHKAF
C.immitis      230 --------FAVLPSQPTHPQ -GSPAWQHHHYFPPSNLHDRYICRICHKAF
A.capsulatus   247 ------------PAQQHHHHS------ISTWQHHHYFPPSNTAPYQQNHDRYICRICHKAF
U.reesii       235 --------FAVLPSQPTHPQ -A GSPAWQHHHYFPPSNLNHDRYICRICHKAF
P.marneffei    143 TP---------STLVPPPPA SNHLT
B.fuckeliana   220 ---------------MPVSVT TPSSGANPWQHHHYISPSSASQDRYICQTCNKAF
N.tetrasperma  197 ---------------VPVPVT APVTGANPWQHHHYIASQDRYICQTCNKAF
N.crassa       197 ---------------VPVPVT APVTGANPWQHHHYIASQDRYICQTCNKAF
M.oryzae       230 ---------------MPVNVS GPQSGANPWQHHHYISPSAASQDRYICQTCNKAF
C.globosum     231 ---------------MSMSMT APTA-GNPWQHHHYIAPSASQDRYICPTCSKAF
F.oxysporum    178 ---------------VSMPA--PAPSGANPWQHHHYLNGAAASQDRYICPTCNKAF A.nidulans     260 SRPSSLRIHSHSHTGEKPFRCTHAGCGKAFSVRSNMKRHER------AVAMV--
A.oryzae       266 SRPSSLRIHSHSHTGEKPFRCTHAGCGKAFSVRSNMKRHER------PVATAM
A.niger        272 SRPSSLRIHSHSHTGEKPFRCTHAGCGKAFSVRSNMKRHER------GCHSGRPVATAM
A.kawachii     272 SRPSSLRIHSHSHTGEKPFRCTHAGCGKAFSVRSNMKRHER------GCHSGRPVATAM
N.fischeri     280 SRPSSLRIHSHSHTGEKPFRCTHAGCGKAFSVRSNMKRHER------PVATAM
P.chrysogenum  243 SRPSSLRIHSHSHTGEKPFRCTHAGCGKAFSVRSNMKRHER------GCHSGRPAPAPAA
C.immitis      281 SRPSSLRIHSHSHTGEKPFRCPHAGCGKAFSVRSNMKRHER------GCHPGRSAPPSA
A.capsulatus   291 VNCGKSFSVRSNMKRHER------PTQAAL
U.reesii       286 SRPSSLRIHSHSHTGEKPFRCPHAGCGKAFSVRNPSQRSLIEKRKGYAIGFDEWVLT
P.marneffei    194 SRPSSLRIHSHSHTGEKPFRCTHAGCGKAFSVRSNMKRHER------GCHSGRPMTATV
```

FIG. 24 (cont.)

```
B.fuckeliana    266 QNCGKAFSVRSNMKRHER------GCHSFESASMV--
N.tetrasperma   243 ------GCHSFESSNGRSS
N.crassa        243 ------GCHSFESSNGRSS
M.oryzae        276 ------GCHNYDSSSSNGT
C.globosum      276 FPGCGKAFSVRSNMKRHER------GCHNYDSSSTTSS
F.oxysporum     222 ------GCHSFEFNGSVIR A.nidulans
A.oryzae        320 --------------------------------------------------
A.niger         326 --------------------------------------------------
A.kawachii      326 --------------------------------------------------
N.fischeri      334 Q-------------------------------------------------
P.chrysogenum   297 TALVV---------------------------------------------
C.immitis       335 VN------------------------------------------------
A.capsulatus    345 N-------------------------------------------------
U.reesii        346 ITPTIRSTNEQIYTTASCKIANVAVININRRIAELRKSFNRRSNGTLSPTKRRVKLAFS
P.marneffei     248 --------------------------------------------------
B.fuckeliana
N.tetrasperma   297 GNSNN---GASA--------------------------------------
N.crassa        297 GNSNN---SASA--------------------------------------
M.oryzae        330 AMH-----------------------------------------------
C.globosum      330 TGTMNSNTGGSR------P-------------------------------
F.oxysporum     276 G-------------------------------------------------
```

FIG. 24 (cont.)

SEQUENCE LISTING

```
<160> NUMBER OF SEQ ID NOS: 93

<210> SEQ ID NO 1
<211> LENGTH: 936
<212> TYPE: DNA
<213> ORGANISM: Aspergillus nidulans

<400> SEQUENCE: 1
atggatctcg ccaacctcat ctcccaaccg gggcctgagc ctgctctgac ggccaaatca    60
agatacagcc ctcctgcctt tgaaccgggc tccttctacg ccgcatctac ttcattcacg   120
cggacacaag cgccactatc gcctccagtc gaggatagat cttctcgctg ctcactgcca   180
tcaatctctg cgcttcttga cagcgcagac ggcgcctcga cacaagctcc aaagcgccaa   240
cggctcagct ctccaatgca ccgtgaaccg cttgacaaga acccatctgc cggcgctgct   300
cccatccgtc tcccgcccac tcctccattg cgccccggct ccggcttcca cagcgccggc   360
cactcgccct cgagctccat ctcatccatc tcgatgatca agtccgagta cccggcacca   420
ccatcagctc cagtctctct tccgggcctt cccagcccaa ccgaccgctc gtccatctcg   480
agccaagggt ctgcgccgca gcaccagcat ggtccctacg cctcgccagc tcccagcgtg   540
gcgccctctt actcctcgcc cgttgagccc tcaccctcat cggcaatgta ctaccaacac   600
cagcggcccg catcctcagg cacataccag gctcctccac ccccgccgca acaccagccc   660
atgatctcgc ccgtgacacc ggcctggcag caccaccact acttccctcc ttcctcaaac   720 acacccctacc agcagaacca cgaccgatat atctgccgca cctgccacaa ggcgttctcg   780
cggccctcga gtctgcgcat ccacagccat agccacaccg gcgagaagcc atttcggtgc   840
acacatgccg gatgcggcaa agcctttagt gtacggagca acatgaagcg ccatgagcgc   900
ggctgccata ccgggagggc tgtcgcgatg gtgtaa                              936

<210> SEQ ID NO 2
<211> LENGTH: 258
<212> TYPE: PRT
<213> ORGANISM: Aspergillus nidulans

<400> SEQUENCE: 2

Met Asp Leu Ala Asn Gln Pro Gly Pro Glu Pro Ala Leu Thr Ala Lys
1               5                   10                  15

Ser Arg Tyr Ser Pro Pro Ala Phe Glu Pro Gly Ser Phe Tyr Ala Ala
            20                  25                  30

Ser Thr Ser Phe Thr Arg Thr Gln Ala Arg Ser Ser Ala Leu Leu Asp
        35                  40                  45

Ser Thr Gln Ala Pro Lys Arg Gln Arg Leu Ser Ser Pro Met His Arg
    50                  55                  60

Glu Pro Leu Asp Lys Asn Pro Ser Ala Gly Ala Ala Pro Ile Arg Gly
65                  70                  75                  80

Ser Gly Phe His Ser Ala Gly His Ser Pro Ser Ser Ser Ile Ser Ser
                85                  90                  95
```

```
Ile Ser Met Ile Lys Ser Glu Tyr Pro Ala Pro Pro Ser Ala Pro Val
                100                 105                 110

Ser Leu Pro Gly Ser Pro Thr Asp Arg Ser Ser Ile Ser Ser Gln Gly
            115                 120                 125

Ser Ala Pro Gln His Gln His Gly Pro Tyr Ala Ser Pro Ala Ala Pro
        130                 135                 140

Ser Ser Pro Ser Ser Ala Met Tyr Tyr Gln His Gln Arg Pro Ala Ser
145                 150                 155                 160

Ser Gly Thr Tyr Gln Ala Pro Pro Pro Pro Gln His Gln Pro Met
                165                 170                 175

Ile Ser Thr Pro Ala Trp Gln His His Tyr Phe Pro Pro Ser Ser
                180                 185                 190

Asn Thr Pro Tyr Gln Gln Asn His Asp Arg Tyr Ile Cys Arg Thr Cys
                195                 200                 205

His Lys Ala Phe Ser Arg Pro Ser Ser Leu Arg Ile His Ser His Ser
        210                 215                 220

His Thr Gly Glu Lys Pro Phe Arg Cys Thr His Ala Gly Cys Gly Lys
225                 230                 235                 240

Ala Phe Ser Val Arg Ser Asn Met Lys Arg His Glu Arg Ala Val Ala
                245                 250                 255

Met Val

<210> SEQ ID NO 3
<211> LENGTH: 247
<212> TYPE: PRT
<213> ORGANISM: Aspergillus oryzae

<400> SEQUENCE: 3

Met Asp Leu Ala Ser Gly Pro Glu Pro Ile Tyr Lys Ser Arg Ala
1               5                   10                  15

Ser Tyr Ser Pro Pro Pro Ser Ser Ala Gly Ser Tyr Lys Arg Pro Ala
                20                  25                  30

Glu His Asp Ser Tyr Phe Ser Arg Ala Pro Gln Ala Gln Pro Glu Gly
            35                  40                  45

Ala Asp Ser Thr Tyr Ala Ala Lys Arg Gln Arg Thr Ser Pro Pro Pro
50                  55                  60

Arg Arg Glu Ser Glu Phe Arg Ser Pro Tyr Asp Ser Val Ser Thr Pro
65                  70                  75                  80

Asn Gly His Ser Gly His His Ser Pro Ser Ala Ser Ser Val Thr Ser
                85                  90                  95

Gly Lys Ala Ile Lys Leu Glu Ser Tyr Ser Gln Thr Pro Met Thr Ser
                100                 105                 110

Pro Ser Asp Arg Ser Ser Ile Ser Ser Gln Gly Ser Val His His Val
            115                 120                 125

Ser Ala Ala Pro Tyr Ala Ser Pro Ala Ala Ser Ser Ala Pro Ser
        130                 135                 140

Ala Met Tyr Tyr Gln Arg Pro Ser Gly Ser Tyr Gln Thr Pro Ala Thr
145                 150                 155                 160

Val Pro Ser Pro Ser Ala Ala Pro Met Pro Ala Ser Ala Thr His Gln
                165                 170                 175

Gln Met Ile Thr Thr Pro Tyr Gln Gln Asn His Asp Arg Tyr Ile Cys
            180                 185                 190

Arg Thr Cys His Lys Ala Phe Ser Arg Pro Ser Ser Leu Arg Ile His
        195                 200                 205
```

```
Ser His Ser His Thr Gly Glu Lys Pro Phe Arg Cys Thr His Ala Gly
    210                 215                 220

Cys Gly Lys Ala Phe Ser Val Arg Ser Asn Met Lys Arg His Glu Arg
225                 230                 235                 240

Pro Val Ala Thr Ala Met Val
                245
```

<210> SEQ ID NO 4
<211> LENGTH: 272
<212> TYPE: PRT
<213> ORGANISM: Aspergillus niger

<400> SEQUENCE: 4

```
Met Asp Leu Ala Ser His Pro Gly Pro Asp Pro Ile Met Lys Ser Arg
1               5                   10                  15

Ala Ser Tyr Ser Pro Pro Met Thr Ser Tyr Lys Arg Ser Ile Glu His
            20                  25                  30

Thr Ser Asp Ser Tyr Phe Pro Ser Val Pro Ile Thr Arg Ser Pro Gln
        35                  40                  45

Pro Gln Ser Pro Glu Gly Ala Met His Ala Ala Lys Arg Thr Arg Met
    50                  55                  60

Thr Pro Pro Leu Gln Arg Asp Leu Asp Ser Arg Gln Gln Ser Gln Ala
65                  70                  75                  80

Tyr Asp Leu Lys Ala Asn Gly Pro Gln Ile Gly Ser Ser Phe His Ser
                85                  90                  95

Ala Gly His Ser Pro Ala Ser Ser Ile Ser Ala Ala Ser Asp Ala Ala
            100                 105                 110

Ala Pro Lys Arg Ser Asp Ser Tyr Pro Gln Val Pro Met Ala Ser Pro
        115                 120                 125

Ser Asp Arg Ser Ser Ile Ser Ser Gln Gly Ser Val Gln Gly Val Ser
    130                 135                 140

Ser Ala Ser Tyr Ala Ser Pro Ala Ser Ser Ala Ser Ala Met Phe
145                 150                 155                 160

Tyr Gln Arg Thr Ala Pro Ser Thr Ser Ala Ala Pro Leu Pro Thr Pro
                165                 170                 175

Ala Ala Pro Gln Gln Ile Ile Ser Asn Pro Ala Trp Gln His His His
            180                 185                 190

Tyr Phe Pro Pro Ser Ser Thr Thr Pro Tyr Gln Gln Asn His Asp Arg
        195                 200                 205

Tyr Ile Cys Arg Thr Cys His Lys Ala Phe Ser Arg Pro Ser Ser Leu
    210                 215                 220

Arg Ile His Ser His Ser His Thr Gly Glu Lys Pro Phe Arg Cys Thr
225                 230                 235                 240

His Ala Gly Cys Gly Lys Ala Phe Ser Val Arg Ser Asn Met Lys Arg
                245                 250                 255

His Glu Arg Gly Cys His Ser Gly Arg Pro Val Ala Thr Ala Met Val
            260                 265                 270
```

<210> SEQ ID NO 5
<211> LENGTH: 272
<212> TYPE: PRT
<213> ORGANISM: Aspergillus kawachii

<400> SEQUENCE: 5

```
Met Asp Leu Ala Ser His Pro Gly Pro Asp Pro Ile Met Lys Ser Arg
1               5                   10                  15
```

```
Ala Ser Tyr Ser Pro Pro Met Thr Ser Tyr Lys Arg Ser Ile Glu Gln
            20                  25                  30

Thr Ser Asp Ser Tyr Phe Pro Ser Val Pro Ile Thr Arg Ser Pro Gln
        35                  40                  45

Pro His Ser Pro Glu Gly Ala Met His Ala Ala Lys Arg Thr Arg Met
    50                  55                  60

Thr Pro Pro Leu Gln Arg Asp Leu Asp Ser Arg Gln Gln Ser Gln Ala
65                  70                  75                  80

Tyr Asp Leu Lys Ala Asn Gly Pro Gln Ile Gly Ser Ser Phe His Ser
                85                  90                  95

Ala Gly His Ser Pro Ala Ser Ser Ile Ser Ala Ala Ser Asp Ala Ala
            100                 105                 110

Ala Pro Lys Arg Ser Asp Ser Tyr Pro Gln Val Pro Met Ala Ser Pro
        115                 120                 125

Ser Asp Arg Ser Ser Ile Ser Ser Gln Gly Ser Val Gln Gly Val Ser
    130                 135                 140

Ser Ala Ser Tyr Ala Ser Pro Ala Ser Ser Ala Ser Ser Ala Met Phe
145                 150                 155                 160

Tyr Gln Arg Thr Ala Pro Ser Thr Ser Ala Ala Pro Leu Pro Thr Pro
                165                 170                 175

Ala Ala Pro Gln Gln Ile Ile Ser Asn Pro Ala Trp Gln His His His
            180                 185                 190

Tyr Phe Pro Pro Ser Ser Thr Thr Pro Tyr Gln Gln Asn His Asp Arg
        195                 200                 205

Tyr Ile Cys Arg Thr Cys His Lys Ala Phe Ser Arg Pro Ser Ser Leu
    210                 215                 220

Arg Ile His Ser His Ser His Thr Gly Glu Lys Pro Phe Arg Cys Thr
225                 230                 235                 240

His Ala Gly Cys Gly Lys Ala Phe Ser Val Arg Ser Asn Met Lys Arg
                245                 250                 255

His Glu Arg Gly Cys His Ser Gly Arg Pro Val Ala Thr Ala Met Val
            260                 265                 270

<210> SEQ ID NO 6
<211> LENGTH: 280
<212> TYPE: PRT
<213> ORGANISM: Neosartorya fischeri

<400> SEQUENCE: 6

Met Asp Val Ala Ser Pro Ser Glu Ser Asp Thr Val Pro Thr Phe Arg
1               5                   10                  15

Ser Arg Ser Ile Gln Asn Ser Ser Ala Ser His Tyr Lys Arg Leu Ser
            20                  25                  30

Glu Gln Tyr Thr Gly Ser Tyr Phe Ser Ala Ala Pro Thr His Thr Thr
        35                  40                  45

Ser Arg Thr Pro Gln Pro Pro Leu Ser Pro Ala Glu Asp Gln Pro
    50                  55                  60

Lys Cys Ser Leu Pro Ser Ile Ser Ile Leu Leu Glu Asn Ala Ala His
65                  70                  75                  80

Ala Ala Lys Arg Gln Arg Thr Ser Leu Ser Thr His Arg Asp Ser Gly
                85                  90                  95

Pro Pro Tyr Asp Ser Ile Thr Pro His Gly Ser Gly Phe His Ser Asn
            100                 105                 110

Gly His Ser Pro Ser Ala Ser Ser Val Ser Ala Thr Ser Ser Ser Ala
```

```
              115                 120                 125
Val Met Lys Asn Thr Glu Thr Tyr Ser Gln Ala Pro Ile Gly Ser Pro
130                 135                 140

Thr Asp Arg Ser Ser Ile Ser Ser Gln Gly Ser Val Gln His Ala Ala
145                 150                 155                 160

Gly Ala Pro Tyr Ala Ser Pro Ala Ser Phe Ser Ser Thr Pro Ser Thr
                165                 170                 175

Ala Ala Tyr Tyr Gln Arg Asn Pro Ala Pro Asn Gln Asn Pro Gly Ser
            180                 185                 190

Phe Pro Pro Thr Ser Ala Ala Ser Leu Pro Ser Pro Gly His Gln Gln
        195                 200                 205

Met Ile Ser Thr Thr Pro Tyr Gln Gln Asn His Asp Arg Tyr Ile Cys
210                 215                 220

Arg Thr Cys His Lys Ala Phe Ser Arg Pro Ser Ser Leu Arg Ile His
225                 230                 235                 240

Ser His Ser His Thr Gly Glu Lys Pro Phe Arg Cys Thr His Ala Gly
                245                 250                 255

Cys Gly Lys Ala Phe Ser Val Arg Ser Asn Met Lys Arg His Glu Arg
            260                 265                 270

Pro Val Ala Thr Ala Met Val Gln
        275                 280

<210> SEQ ID NO 7
<211> LENGTH: 244
<212> TYPE: PRT
<213> ORGANISM: Penicillium chrysogenum

<400> SEQUENCE: 7

Met Asp Leu Ser Asn His Ser Ala Ala Val Lys Pro Ile Tyr Thr Pro
1               5                   10                  15

Val Glu Ser Tyr Lys Arg Ser Pro Pro Leu Ser Pro Ala Pro Lys
            20                  25                  30

Val Phe Glu Gly Gln His Ala Ala Thr Ser Leu Thr Leu Asn Leu Pro
        35                  40                  45

Glu Arg Gln Arg Leu Ser Pro Ser Leu Gly Asp Arg His Val Arg Val
    50                  55                  60

Gln Ser Tyr Glu Gly Ser Gly His Ala His Arg Arg Ala Ser Pro Val
65                  70                  75                  80

Glu Ser Leu Ser His Lys Glu Ala His Gln His His Leu His Arg Ser
                85                  90                  95

Ser Ile Ser Ser Asn Ser Ser Val His Ile Pro Arg Asn Thr Val Pro
            100                 105                 110

Tyr Ala Ser Pro Val Thr Ala Pro Gln Gln Pro Met Tyr Tyr Pro Arg
        115                 120                 125

Pro Pro Thr Thr Ser Gln Pro Ser Thr Pro Ala Ser Ala Pro Gln Met
130                 135                 140

Pro Pro Val Gln Val Gln Thr Gln Gln Pro His Ser His Ser His Ser
145                 150                 155                 160

Ser Ser Ala Leu Ile Ser Thr Pro Tyr Gln Gln Asn His Asp Arg Tyr
                165                 170                 175

Ile Cys Arg Thr Cys His Lys Ala Phe Ser Arg Pro Ser Ser Leu Arg
            180                 185                 190

Ile His Ser His Ser His Thr Gly Glu Lys Pro Phe Arg Cys Thr His
        195                 200                 205
```

```
Ala Gly Cys Gly Lys Ala Phe Ser Val Arg Ser Asn Met Lys Arg His
    210                 215                 220

Glu Arg Gly Cys His Ser Gly Arg Pro Ala Pro Ala Pro Ala Ala Thr
225                 230                 235                 240

Ala Leu Val Val

<210> SEQ ID NO 8
<211> LENGTH: 297
<212> TYPE: PRT
<213> ORGANISM: Coccidioides immitis

<400> SEQUENCE: 8

Met Asn Val Ser Ser Cys Asp Gln Pro His Gln Leu Arg Ala Pro Ala
1               5                   10                  15

Ser Ser Tyr Ser Glu His Arg Arg Ser Pro Ser Ile Pro Lys Pro Leu
            20                  25                  30

Gln Thr Glu Ser Ser Ser Cys Ala Ser Pro Tyr Ser Arg Phe Glu Arg
        35                  40                  45

Leu Pro Leu Ser Pro Pro Glu Glu Asp Gly Lys Thr Gln Phe Arg Gly
    50                  55                  60

Val Val Ser Asp Ala His Val Ala Lys Arg Gln Arg Thr Asn Pro Pro
65                  70                  75                  80

Pro Ser Ile Asp Leu Gly Met Glu Arg Arg Thr Ile Asp Gln Thr Leu
                85                  90                  95

Lys Gln Arg Pro Leu Met Asn Ser Thr Ser Gln Ser Pro Ser Thr Ser
            100                 105                 110

Ser Pro Pro Arg Ser Ala Ile Ser Leu Pro Ser Leu Val Arg Ser Tyr
        115                 120                 125

Pro Ser Pro Val Ser Glu Val Pro Glu Gly Arg Arg Met Ser Gln Ile
    130                 135                 140

Ser Arg His Ser Arg Gly Ala Ser Thr Ser Gln Thr Ser Gln Leu Ser
145                 150                 155                 160

Gly Pro Glu Thr Arg Tyr Pro Ser Pro Pro Asn Val Asn Ser Pro Thr
                165                 170                 175

Phe Ala Ala Ala Pro Lys Pro Thr Glu Tyr Tyr Pro Ala Ser Arg Pro
            180                 185                 190

Val Pro Pro Val Ala Phe Ala Val Leu Pro Ser Gln Pro Thr His Pro
        195                 200                 205

Gln Val Leu Gly Ser Pro Ala Trp Gln His His Tyr Phe Pro Pro
    210                 215                 220

Ser Asn Leu Asn His Asp Arg Tyr Ile Cys Arg Ile Cys His Lys Ala
225                 230                 235                 240

Phe Ser Arg Pro Ser Ser Leu Arg Ile His Ser His Ser His Thr Gly
                245                 250                 255

Glu Lys Pro Phe Arg Cys Pro His Ala Gly Cys Gly Lys Ala Phe Ser
            260                 265                 270

Val Arg Ser Asn Met Lys Arg His Glu Arg Gly Cys His Pro Gly Arg
        275                 280                 285

Ser Ala Pro Pro Ser Ala Leu Val Asn
    290                 295

<210> SEQ ID NO 9
<211> LENGTH: 268
<212> TYPE: PRT
<213> ORGANISM: Ajellomyces capsulatus
```

<400> SEQUENCE: 9

Met Asn Leu Ser His Ser Tyr His Ser Pro Ser Thr Tyr Pro His
1               5                   10                  15

Ser Gly Thr Ser Gln Lys Arg Gln Ser Leu Gln Ser Glu Ser Ser Leu
            20                  25                  30

Ser Val Ser Asn Gly Tyr Tyr Asp Arg Asn Ala Ser Asn Leu Ala Tyr
        35                  40                  45

Ala Arg Ser Pro Gln Pro Gln Ser Arg Phe Gln Gly Ala Asp Gln Leu
    50                  55                  60

Ser Pro Val His Ile Ala His Arg Pro Asn Pro Leu Ser Thr Gly Glu
65              70                  75                  80

Val Asp Leu Lys Ser Gln Gly His Gly Ala Thr Gln Lys Pro Ile His
                85                  90                  95

Arg Pro Arg Met Ile Gly Ser Gly Leu Asp Gly Arg Asn His Ser Pro
            100                 105                 110

Ala Gly Ser Ser Pro Ser Ser Ala His Ser Pro Ile Ser Val Ala Asn
        115                 120                 125

Leu Thr Ser Ser Ser Ala Asp Pro Ser Tyr Gln His Arg Met Pro
    130                 135                 140

Gln Gly Pro Pro Gln Ser Thr Asn Ser Pro Val Ser Leu Pro Glu Lys
145                 150                 155                 160

His Tyr Ala Pro Ser Ser Asn Leu Ser Ser Thr Pro Phe Ala Leu Ala
                165                 170                 175

Asn Ser Thr Glu Tyr Tyr His Arg Pro Ser His Pro Pro Ser Thr Ser
            180                 185                 190

Ile Pro Leu Ala Ala Pro Pro Ala Gln Gln His His His Ser Met
        195                 200                 205

Ile Ser Thr Trp Gln His His His Tyr Phe Pro Pro Ser Asn Thr Ala
    210                 215                 220

Pro Tyr Pro Gln Asn His Asp Arg Tyr Ile Cys Arg Ile Cys His Lys
225                 230                 235                 240

Ala Phe Val Asn Cys Gly Lys Ser Phe Ser Val Arg Ser Asn Met Lys
                245                 250                 255

Arg His Glu Arg Pro Thr Gln Ala Ala Leu Val Asn
            260                 265

<210> SEQ ID NO 10
<211> LENGTH: 360
<212> TYPE: PRT
<213> ORGANISM: Uncinocarpus reesii

<400> SEQUENCE: 10

Met Asn Val Ser Ser Cys Asp Gln Thr Ala Pro Phe His Gly Ser Ala
1               5                   10                  15

Thr Ser Tyr Phe Glu His His Gln Arg Ile Arg Ser Pro Ser Ile Pro
            20                  25                  30

Lys Arg Ser His Glu Glu Asn Ser Ser Ala Ser Pro Tyr Pro Pro
        35                  40                  45

Phe Ala Thr Leu Pro Leu Ser Pro Pro Glu Gly Lys Thr Thr Phe Gln
    50                  55                  60

Ser Val Asp Thr His Val Ala Lys Arg Gln Arg Ala Asn Pro Pro Pro
65              70                  75                  80

Ser Ile Asp Leu Ala Leu Glu Arg Arg Gly Ala Cys Ala Asp Gln Ala
                85                  90                  95

```
Ile Arg Gln Arg Pro Leu Met Gly Gly Val Asn His Ser Pro Ser Ala
            100                 105                 110

Ser Ser Pro Pro Arg Thr Ala Ile Ser Leu Pro Ser Leu Ile Gly Ser
        115                 120                 125

Tyr Pro Ser Pro Val Ser Glu Ala Pro Glu Gly Arg Arg Met Ser Gln
    130                 135                 140

Ile Ser Arg His Ser Ser Ser Gln His Pro Gly Pro Glu Ala Arg
145                 150                 155                 160

Tyr Pro Ser Pro Thr Leu Ser Ser Pro Ser Phe Ala Ala Pro Pro
                165                 170                 175

Lys Pro Glu Tyr Tyr Ser Ser Gly Ala Arg Pro Thr Asn Phe Pro Pro
            180                 185                 190

Val Thr Phe Ala Val Leu Pro Ser Gln Pro Thr His Pro Gln Met Val
        195                 200                 205

Ala Leu Gly Ser Pro Ala Trp Gln His His Tyr Phe Pro Pro Ser
    210                 215                 220

Asn Leu Asn His Asp Arg Tyr Ile Cys Arg Ile Cys His Lys Ala Phe
225                 230                 235                 240

Ser Arg Pro Ser Ser Leu Arg Ile His Ser His Ser His Thr Gly Glu
                245                 250                 255

Lys Pro Phe Arg Cys Pro His Ala Gly Cys Gly Lys Ala Phe Ser Val
            260                 265                 270

Arg Asn Gln Pro Arg Ser Gln Arg Ser Leu Ile Glu Lys Arg Lys Gly
        275                 280                 285

Tyr Ala Ile Gly Phe Asp Glu Trp Val Leu Thr Met Ile Thr Pro Thr
    290                 295                 300

Ile Arg Ser Thr Asn Glu Gln Ile Tyr Thr Thr Ala Ser Cys Lys Ile
305                 310                 315                 320

Ala Asn Val Ala Val Ile Asn Ile Asn Arg Arg Ile Ala Glu Leu Arg
                325                 330                 335

Lys Ser Phe Arg Asn Arg Arg Ser Asn Gly Thr Leu Ser Pro Thr Lys
            340                 345                 350

Arg Arg Val Lys Leu Ala Phe Ser
        355                 360

<210> SEQ ID NO 11
<211> LENGTH: 205
<212> TYPE: PRT
<213> ORGANISM: Penicillium marneffei

<400> SEQUENCE: 11

Met Asp Asn Val Pro Ala Ser Lys Arg Ala Arg His Asp Ser Gly Asp
1               5                   10                  15

Tyr Ser Arg Gly Phe Cys Ser Gly Phe Thr Glu Gly Ser Ser Pro Ala
            20                  25                  30

Ser Leu Pro Ser Gly Arg Ser His Ser Ala Ser Ile Ser Ser Ala Val
        35                  40                  45

Ser His Pro Ser His Gln Gln Arg Thr Ser Leu Pro Ser Ile Ser Ala
    50                  55                  60

Ser Leu Gln Asn Thr Pro Ile His Pro Ser Glu Arg Leu Ser Ile Ser
65                  70                  75                  80

Ser Leu Ala Ser His Asp Ser Ser Arg Leu Ser His Ala Ile Pro Ser
                85                  90                  95

Pro Ser Ser Thr Thr Ala Ser Ile Thr Thr Thr Ala Thr Pro Ser Thr
            100                 105                 110
```

```
Ser Tyr Tyr Ser Thr Ser Glu Glu Lys Ala Tyr Pro Arg Ser His Ser
            115                 120                 125

<213> ORGANISM: Neurospora tetrasperma

<400> SEQUENCE: 13

```
Met Ala Pro Thr Thr Leu Thr Pro Gln Tyr Pro Ala Gln Pro Tyr Gly
1               5                   10                  15

Phe Ala Pro Pro Pro Ser Asn Lys Cys Ser Leu Pro Ser Ile Ser Asn
                20                  25                  30

Leu Leu Val Met Ala Asp Gln Pro Thr Ser Glu Thr Ser Pro Gln Ser
            35                  40                  45

Gln Gln Leu His Phe Ser Lys Pro Asp Asn Asn Ser Ser Gln Phe Gly
        50                  55                  60

Asn Pro Ala Ser Ile Arg Ala Asn Ser Ser Glu Ala Ser Phe Glu Gly
65                  70                  75                  80

Tyr Arg Ser Pro Ser Ser Lys Pro Ala Ser Gln Ser Gln Gly Ser Ser
                85                  90                  95

Asn Tyr Tyr Tyr Glu Thr Thr Pro Pro Leu Ser Gln His Glu Ala Asp
                100                 105                 110

Ser Arg Gln Met Ala Thr Ala Ala Pro Arg Ala Pro Val Gln Ser Ser
            115                 120                 125

Thr Phe Gln Thr Gln Tyr Pro Ser Ser Ala Gly Tyr Ser Ser Gln Ser
        130                 135                 140

Gly Met Asn Pro Tyr Tyr Pro Pro Met Gln Pro Thr Pro Pro Gln
145                 150                 155                 160

Gln Gln Met Ser Gly Leu Tyr Tyr Gln Arg Pro Leu Pro Gln Thr Pro
                165                 170                 175

Ala Val Pro Val Pro Val Thr Leu Ala Pro Val Thr Gly Ala Asn Pro
                180                 185                 190

Trp Gln His His His Tyr Ile Ala Ser Gln Asp Arg Tyr Ile Cys Gln
                195                 200                 205

Thr Cys Asn Lys Ala Phe Gly Cys His Ser Phe Glu Ser Ser Asn Gly
        210                 215                 220

Arg Ser Ser Gly Asn Ser Asn Gly Ala Ser Ala
225                 230                 235
```

<210> SEQ ID NO 14
<211> LENGTH: 236
<212> TYPE: PRT
<213> ORGANISM: Neurospora crassa

<400> SEQUENCE: 14

```
Met Ala Pro Thr Thr Leu Thr Pro Gln Tyr Pro Ala Gln Pro Tyr Gly
1               5                   10                  15

Phe Ala Pro Pro Pro Ser Asn Lys Cys Ser Leu Pro Ser Ile Ser Asn
                20                  25                  30

Leu Leu Val Met Ala Asp Gln Pro Thr Ser Glu Thr Ser Pro Gln Ser
            35                  40                  45

Gln Gln Leu His Phe Ser Lys Pro Asp Asn Asn Ser Ser Gln Phe Gly
        50                  55                  60

Asn Pro Ala Ser Ile Arg Ala Asn Ser Ser Glu Ala Ser Phe Glu Gly
65                  70                  75                  80

Tyr Arg Ser Pro Ser Ser Lys Pro Ala Ser Gln Ser Gln Gly Ser Ser
                85                  90                  95

Asn Tyr Tyr Tyr Glu Thr Thr Pro Pro Leu Ser Gln His Glu Ala Asp
                100                 105                 110

Ser Arg Gln Met Ala Thr Ala Thr Pro Arg Ala Pro Val Gln Ser Ser
```

```
        115                 120                 125

Thr Phe Gln Thr Gln Tyr Pro Ser Ser Ala Gly Tyr Ser Ser Gln Ser
    130                 135                 140

Gly Met Asn Pro Tyr Tyr Pro Pro Met Gln Pro Thr Pro Pro Pro Gln
145                 150                 155                 160

Gln Gln Met Ser Gly Leu Tyr Tyr Gln Arg Pro Leu Pro Gln Thr Pro
                165                 170                 175

Ala Val Pro Val Pro Val Thr Leu Ala Pro Val Thr Gly Ala Asn Pro
            180                 185                 190

Trp Gln His His His Tyr Ile Ala Ser Gln Asp Arg Tyr Ile Cys Gln
        195                 200                 205

Thr Cys Asn Lys Ala Phe Gly Cys His Ser Phe Glu Ser Ser Asn Gly
    210                 215                 220

Arg Ser Ser Gly Asn Ser Asn Asn Ser Ala Ser Ala
225                 230                 235

<210> SEQ ID NO 15
<211> LENGTH: 267
<212> TYPE: PRT
<213> ORGANISM: Magnaporthe oryzae

<400> SEQUENCE: 15

Met Ala Ala Thr Met Ile Gln Gln Pro Tyr Pro Ile His Gln Gln Gln
1               5                   10                  15

Ser Gln Tyr Met Val Gln Pro Gln Gly Pro Pro Asp Asn Lys Cys Ser
            20                  25                  30

Leu Pro Ser Ile Ser Asn Leu Leu Gly Leu Ala Asp Gln Pro Thr Ser
        35                  40                  45

Glu Thr Ser Ala Gln Tyr Thr Pro Arg Ala Glu Ala Thr Thr Arg Leu
    50                  55                  60

Leu Ala Thr Gly Lys Gln Ala Thr Lys Gly Asn Asn Leu Ala Val Ile
65                  70                  75                  80

Leu Thr Ser Gln Thr Ala Ala Gln Gln Ser Asn Ser Ser His Tyr Ser
                85                  90                  95

Asn Ala Val Gln Ser Val Arg Gln Thr Ser Glu Thr Ser Phe Asp Gly
            100                 105                 110

Tyr Asn Ser Pro Ser Asn Lys Ser Val Ser Gln Leu Pro Ala Thr Gly
        115                 120                 125

Tyr Tyr Phe Glu Ala Thr Pro Pro Pro Gly His Met Glu Met Glu Pro
    130                 135                 140

Arg Pro His Met Thr Ser Val Ser Arg Val Pro Val Gln Ala Pro Phe
145                 150                 155                 160

Ala Gln Ser Ala Tyr Ser Ala Pro Tyr Gly Met Ala Pro Ser Asn Pro
                165                 170                 175

Met Ala Ala Tyr Tyr Pro Thr Met Gln Pro Thr Pro Pro Pro Gln Gln
            180                 185                 190

Pro Gln Ile Ser Ser Leu Tyr Tyr Gln Arg Pro Leu Pro Gln Ala Phe
        195                 200                 205

Pro Pro Met Pro Val Asn Val Ser Met Gly Pro Gln Ser Gly Ala Asn
    210                 215                 220

Pro Trp Gln His His His Tyr Ile Ser Pro Ser Ala Ala Ser Gln Asp
225                 230                 235                 240

Arg Tyr Ile Cys Gln Thr Cys Asn Lys Ala Phe Gly Cys His Asn Tyr
                245                 250                 255
```

```
Asp Ser Ser Ser Ser Asn Gly Thr Ala Met His
            260                 265
```

<210> SEQ ID NO 16
<211> LENGTH: 291
<212> TYPE: PRT
<213> ORGANISM: Chaetomium globosum

<400> SEQUENCE: 16

```
Met Ala Asn Thr Met Val Thr His Tyr Ala His Val Pro Gln His Ser
1               5                   10                  15

Leu Gln Tyr Gly Tyr Met Pro Pro Ala Ala Lys Cys Ser Leu Pro
            20                  25                  30

Ser Ile Ser Asn Leu Leu Gly Leu Ala Asp Gln Pro Thr Ser Glu Thr
            35                  40                  45

Ser Pro Gln Ser Gln Gln Gln Gln Ala Gln Gln Gln Gln Gln
        50                  55                  60

Gln Cys Met Ser Ser Trp Trp Asp Met Gly His Leu Asp Thr Asp
65                  70                  75                  80

Ser Thr Pro Ala Gln Gly Ser Lys Pro Glu Thr Asn Ser Ser His Tyr
                85                  90                  95

Thr Asn Pro Val Thr Ile Arg Thr Ser Ser Asp Ala Ser Phe Glu Gly
            100                 105                 110

Phe Asn Ser Pro Ser Thr Arg Ser Val Ser Gln Val Pro Asn Gly Ser
            115                 120                 125

Asn Tyr Phe Phe Glu Thr Thr Pro Pro Leu Gln Met Glu Ala Asp Ala
    130                 135                 140

Arg Gln Met Thr Ala Ala Ala Val Ser Val Gln Ala Ser Ala Tyr
145                 150                 155                 160

Gln Pro Gln Tyr Ala Pro Gly Pro Ala Tyr Met Ser Gln Pro Ala Met
                165                 170                 175

Thr Ser Tyr Tyr Pro Pro Met Gln Ser Ala Ala Pro Pro Gln Thr Gln
            180                 185                 190

Met Ser Gly Leu Tyr Tyr Gln Arg Pro Leu Pro Gln Pro Pro Met
            195                 200                 205

Ser Met Ser Met Thr Leu Ala Pro Thr Ala Gly Asn Pro Trp Gln His
    210                 215                 220

His His Tyr Ile Ala Pro Ser Ala Ser Gln Asp Arg Tyr Ile Cys Pro
225                 230                 235                 240

Thr Cys Ser Lys Ala Phe Phe Pro Gly Cys Gly Lys Ala Phe Ser Val
                245                 250                 255

Arg Ser Asn Met Lys Arg His Glu Arg Gly Cys His Asn Tyr Asp Ser
            260                 265                 270

Ser Ser Thr Thr Ser Thr Gly Thr Met Asn Ser Asn Thr Gly Gly
        275                 280                 285

Ser Arg Pro
    290
```

<210> SEQ ID NO 17
<211> LENGTH: 214
<212> TYPE: PRT
<213> ORGANISM: Fusarium oxysporum

<400> SEQUENCE: 17

```
Met Glu Glu Gln Lys Cys Ser Leu Pro Ser Ile Ser Asn Leu Leu Gly
1               5                   10                  15
```

```
Leu Pro Thr Ser Glu Ser Ser Pro Thr Ser Arg Gln His Ser Pro Arg
             20                  25                  30

Phe Glu Val Pro Pro Pro Ser His Gly His Ser Arg Ala Gly Ser Glu
         35                  40                  45

Trp Ala Lys Ser Ser His Arg Ser Thr Asp Ala Ser Phe Glu Gly Tyr
 50                  55                  60

Ser Ser Pro Thr Arg Lys Pro Ser Asn Gln Ala Tyr Pro Gly Ser Ala
 65                  70                  75                  80

Pro Arg Thr Tyr Tyr Tyr Glu Thr Thr Pro Leu Glu Ala Asp Ala
                 85                  90                  95

Gln Arg Gln Ala Ser Val Thr Ala Ala Thr Pro Pro Ala Thr Ala Pro
            100                 105                 110

Tyr Pro Gln Gln Ala His Pro Thr Val Tyr Ala Asn Pro Ala Pro Val
            115                 120                 125

Gly Ala Tyr Tyr Pro Ala Ala Gln Val Pro Pro Ala Val Gln Pro Gln
        130                 135                 140

Glu Met Asn Pro Tyr Tyr Gln Arg Pro Leu Pro Gln Ala Tyr Pro Pro
145                 150                 155                 160

Pro Val Ser Met Pro Ala Pro Ala Pro Ser Gly Ala Asn Pro Trp Gln
                165                 170                 175

His His His Tyr Leu Asn Gly Ala Ala Ala Ser Gln Asp Arg Tyr Ile
            180                 185                 190

Cys Pro Thr Cys Asn Lys Ala Phe Gly Cys His Ser Phe Glu Phe Asn
            195                 200                 205

Gly Ser Val Ile Arg Gly
        210
```

```
<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacggcgatt cactcacttg ggc                                                23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taacttacgc atgagaagca gccg                                               24

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaaaaccgc ggggatctgc actaggagat tg                                      32
```

```
<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaaaaggta ccgaccgtga tacctgatct tc                                 32

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaaaaggta ccatggatct cgccaacctc atc                                33

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaaaattaa ttaattacac catcgcgaca gccc                               34

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atggaagagg aagttgctgc tctcgttatc gacaatggtt c                       41

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caatggaggg gaagacggca cggg                                          24

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagcccccag cgatcagc                                                 18

<210> SEQ ID NO 27
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggggttgct ctcgtgcc                                                 18

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttatctaaag gccccccat caa                                            23

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgtcctcct ccccgataat taccgtc                                       27

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
catctcacca gccacaatta caggcggaac catcac                             36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgcgagcca gacacagagg tcataacagt gcttgc                             36

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tccagcaaat ggaaccgtgg aatcaggtgc tc                                 32

<210> SEQ ID NO 33
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaagggatgg ggcaagaatg agacttctgc gggtaa                               36

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agctgcctgg tgacggtagt tgttgttggt gttgc                                35

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caggaacgaa tgcctatgcc cgactttctc tctgga                               36

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacaaggaca gaccgtgatg caggaga                                         27

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cccgacgcag ccttagcgaa caagac                                          26

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccattgactt cgcaactggc ctcattcatg gcaaa                                35

<210> SEQ ID NO 39
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 39
gccttccggc ccacatgatc gaagac                                          26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gccccaagtc cattgtcctc gttcac                                          26

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tctgcgcctg ctcgagagca gcatc                                           25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catggaccct acagcactcc ttcct                                           25

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgctctcaa agttccgct                                                  19

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccccacctca tctccagcat c                                               21

<210> SEQ ID NO 45
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 45
caccatcgcg acagccct                                                   18

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaattgtgt tactccacct cctcg                                           25

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttgagatcgc ttgcgctcct ag                                              22

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agggctgtcg cgatggtgac cggtcgcctc aaacaatgct ct                        42

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgaggaggtg gagtaacaca attgggtctg agaggaggca ctgatgcg                  48

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atggagcccc cagcgatcag ccag                                            24

<210> SEQ ID NO 51
<211> LENGTH: 31
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 51
ttggtgatgg tgctgtctttt ggctgctcaa c                                        31

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gccctcaccc tcatcggcaa tg                                                   22

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggtcgtggtt ctgctggtag ggtgt                                                25

<210> SEQ ID NO 54
<211> LENGTH: 936
<212> TYPE: DNA
<213> ORGANISM: Aspergillus nidulans

<400> SEQUENCE: 54
atggatctcg ccaacctcat ctcccaaccg gggcctgagc ctgctctgac ggccaaatca          60
agatacagcc ctcctgcctt tgaaccgggc tccttctacg ccgcatctac ttcattcacg         120
cggacacaag cgccactatc gcctccagtc gaggatagat cttctcgctg ctcactgcca         180
tcaatctctg cgcttcttga cagcgcagac ggcgcctcga cacaagctcc aaagcgccaa         240
cggctcagct ctccaatgca ccgtgaaccg cttgacaaga acccatctgc cggcgctgct         300
cccatccgtc tcccgcccac tcctccattg cgccccggct ccggcttcca cagcgccggc         360
cactcgccct cgagctccat ctcatccatc tcgatgatca agtccgagta cccggcacca         420
ccatcagctc cagtctctct tccgggcctt cccagcccaa ccgaccgctc gtccatctcg         480
agccaagggt ctgcgccgca gcaccagcat ggtccctacg cctcgccagc tcccagcgtg         540
gcgccctctt actcctcgcc cgttgagccc tcaccctcat cggcaatgta ctaccaacac         600
cagcggcccg catcctcagg cacataccag gctcctccac cccgccgca acaccagccc         660 atgatctcgc ccgtgacacc ggcctggcag caccaccact acttccctcc ttcctcaaac         720 acccctacc agcagaacca cgaccgatat atctgccgca cctgccacaa ggcgttctcg         780
cggccctcga gtctgcgcat ccacagccat agccacaccg gcgagaagcc atttcggtgc         840
acacatgccg gatgcggcaa agcctttagt gtacggagca acatgaagcg ccatgagcgc         900
ggctgccata ccgggagggc tgtcgcgatg gtgtaa                                    936

<210> SEQ ID NO 55
<211> LENGTH: 960
<212> TYPE: DNA
<213> ORGANISM: Aspergillus oryzae

<400> SEQUENCE: 55

```
atggatctcg ccagccttat cactccgggt cctgaaccca tctacaagtc tcgggcatcc      60
tacagccctc ctcccagctc tgcgggttcc tacaagcgcc cggctgaaca cgactcttac     120
ttctcgtact cgcgcgcccc gcaagcccct ctttccccgc cagtcgagga ccagcccaag     180
tgctctcttc cctctatctc gactctcttg gaaggcgccg acagcgcatc gacatatgct     240
gcaaagcgtc aaagaaccag cccacccccg cgcagggagt ctgagttccg ttcacccttat    300
gactcagtct caacaccaaa tggccctcct actccacctt tgcgccctga atcgggcttc     360
cacagcggcc accactctcc ctctgcttcg tccgtgacta gtggaaaggc catcaagctc     420
gagtcgtact cgcaaacccc catgacactg cctagcccgt ccgatagatc ctcgatctcc     480
agccagggct ctgtccacca cgtttccgct gctccctacg cttctcctgc ccccagtgtg     540
gcctcgtact cttcgccggt tgaatcctcg gctccgtccg ccatgtacta ccagagacct     600
tccggctcct accagacccc cgctactgtg cctagcccct ccgctgctcc tatgcctgca     660
tctgccacac accagcagat gattactccc gtcactccgg cctggcagca ccaccactac     720
ttcccgcctt ccagctcggc accctaccaa cagaaccacg accggtatat ctgccggact     780
tgccacaagg ccttctccag accatccagc ctgcgcatcc actctcacag ccacactggc     840
gagaagccat ccgctgcac ccacgccggc tgcggtaagg cgttcagcgt acgaagcaac      900
atgaagcgcc acgagcgcgg ctgccacacc ggacgccccg tcgccaccgc catggtataa     960
```

<210> SEQ ID NO 56
<211> LENGTH: 1008
<212> TYPE: DNA
<213> ORGANISM: Aspergillus clavatus

<400> SEQUENCE: 56

```
atggatctcg caaacctcat ctcgcatccc acctccgagg ctgcctcgac tttcaagtcg      60
aggtcagctc agagtcctcc cgcctttcaa gcgaaccctt acaagcgtct ctccggatcg     120
tcgatgagct cttacttcac ctccgtaccg acgaccgcga catcgtattc tcgcaccccg     180
cagccaccac tctccccacc cgtcgacgac cggcccagat gttcgctgcc ctcaatctcg     240
actctactgg agggtgcaga cagcgcagcc gcacatgcag cgaaacgcca agaactagc      300
ctctcggcgc atagggatct tgatgcccgt cctcagtcgc aaccgtatga cacgatcacc     360
ccacatgcct tgccacctac gccgccattg cgtcctggct cgggttttcg cagcaacggc     420
cattcgcctt cagcctcgtc tgtttccgca acgagcgcca gcacggtgat caagaccgaa     480
acatatcctc agcctcacat cggccttccc agcccgacag atcgctcctc catctccagc     540
caaggatcgg tgcagcatgc gcccggagcc ccgtatgcgt cgccagcgcc tagcgtggca     600
tcttactcgt cacctgtcga gccttccaca ccgtccagcg cagcctacta tcaaagaaag     660
gccccttcag ctcccttcca gaacccaggc agcgtcccct cagcatcggc cgctcaccag     720
cagcttatca ccccccatcac ccccgcctgg caacaccacc actatttccc cccatccagc     780
tcaaccgcct accagcagaa ccatgatcgc tacatctgcc gcacctgcca caaagcgttc     840
tcgcgccctt ccagtctgcg catccactcc cacagccaca cgggcgagaa gccctttcgc     900
tgcacacacg ccggctgcgg caaggccttc agcgtgcgaa gcaatatgaa cgccatgag      960
cgtggatgcc atacaggccg cccagtcgcc actgctatgg tgtcataa                 1008
```

<210> SEQ ID NO 57
<211> LENGTH: 978

```
<212> TYPE: DNA
<213> ORGANISM: Aspergillus niger

<400> SEQUENCE: 57
atggatctcg ccagcctcat ctcccacccg ggacccgatc ccatcatgaa gtctagagcc      60
tcatacagcc ctcccatgac ttcctacaag cgctccatcg aacacacctc ggactcctac     120
ttcccctccg tcccgatctc ctacacccgc tccccgcagc ctcctctctc ccgcctgtc     180
gaggaccagt cccccaagtg ctctcttccc tccatctcta ccttgctcga gggcgcagat     240
ggcgcagcta tgcatgcagc aaagcgcact agaatgaccc tcctctgca cgcgacctt     300
gattcccgc aacagtcgca agcatatgac ctcaaagcta cggcccca aatcgccttg        360
ccccccaccc cccattgcg ccccggttct agcttccaca gcgccggaca ctcccccgcc      420
tcctccatct ctgctgccag cgatgctgct gcgcccaagc gctccgactc ctaccctcaa     480
gtgcccatgg ctctgcctag cccctcggat cgctcgtcca tctccagcca gggttcagtt     540
cagggtgtct ccagtgcttc ctacgcttct cccgctccca cgtctcttc ctactcctct      600
cccattgagc cttcggcctc gtccgccatg ttctaccaac gcacggctcc ctccacttcc     660
gccgctcctc tcccgacgcc agcagcaccg caacagatta tctcccctgt gaaccctgcc     720
tggcagcacc accactactt ccctccctcc agcaccacgc cctaccagca gaaccatgat     780
cgctatatct gccgcacctg ccacaaggcc ttctcgagac cctccagcct gcgcatccac     840
tcccacagcc acacgggcga aagcccttc cgctgcaccc acgccggttg tgggaaggcc      900
ttcagcgtgc gcagcaacat gaagcgtcat gagcgtggct gccacagtgg tcggcccgtc     960
gcaaccgcca tggtttaa                                                   978

<210> SEQ ID NO 58
<211> LENGTH: 978
<212> TYPE: DNA
<213> ORGANISM: Aspergillus kawachii

<400> SEQUENCE: 58
atggatctcg ccagcctcat ctcccacccg ggacccgatc ccatcatgaa gtctagagcc      60
tcatacagcc ctcccatgac ctcttacaag cggtccatcg aacagacttc cgactcatac     120
ttcccctccg tcccgatctc ctacacccgc tccccgcagc ctcctctctc ccgcctgtg     180
gaggaccact ctcccaagtg ctctcttcct tccatctcta ccttgcttga gggcgcagat     240
ggcgcagcta tgcacgcagc aaagcgtact agaatgaccc tcctctgca gcgcgacctt     300
gattcccgcc aacagtcgca agcatatgac ctcaaagcaa cggcccccaa aatcgccctg     360
ccccccacgc ccccattgcg ccctgggtct agcttccaca gcgccggcca ctcccccgct     420
tcctccatct ctgctgccag cgatgctgct gcgcccaagc gctccgactc ctaccctcaa     480
gtgcccatgg ctctgcctag cccttcggat cggtcgtcca tctccagcca gggttccgtt     540
cagggtgtct ccagcgcttc ctacgcttct cccgcgccca cgtctcttc ctactcctct      600
cccattgagc cttcggcctc ctccgctatg ttctaccagc gcacggcgcc ttccacttcg     660
gccgctcctc tcccgacacc ggcagcaccg caacagatta tctcccctgt gaaccctgcc     720
tggcaacacc accactactt ccctccctcc agcaccacgc cctaccagca gaaccatgat     780
cgctatatct gccgcacctg ccacaaggcc ttctcgagac cttccagcct gcgcatccac     840
tcccacagcc acacgggcga aagcccttc cgctgcaccc acgctggttg tgggaaggcc      900
ttcagtgtgc gcagcaacat gaagcgtcat gagcgtggtt gccacagtgg tcggcccgtc     960
```

```
gcaactgcca tggtataa                                                  978
```

<210> SEQ ID NO 59
<211> LENGTH: 1011
<212> TYPE: DNA
<213> ORGANISM: Aspergillus fumigatus

<400> SEQUENCE: 59

```
atggatgtcg caagcctcat ctcgccttct gaatcggata ctgtcccgac cttcaggtca      60
agatcgattc agaattcatc agccagccat acaagcgcc tctccgaaca atcaacaggc     120
tcttacttct ctgctgtgcc aacacataca acgtcttact ctcgtacccc tcagccacca    180
ctgtcccctc cagcggagga ccagtccaaa tgctcgcttc cttccatctc gatcctgctt    240
gagaacgcag acggtgccgc cgcacacgca gcaaaacgcc aacgaaacag cctatcaacg    300
cacagggatt cggatccccg gcctccatat gactcgatca caccacacgc catgccgcca    360
acgccgccat tgcgtcccgg ttcgggcttc acagtaatg ccattctccc ctcgacatca     420
tctgtctctg ccgctagctc cagcgctttg atgaaaaaca cagaatcgta tcctcaggcg    480
ccaattgggc ttcctagtcc aacggatcga tcctcgatct cgagccaagg gtccgttcag    540
catgccgcca cgctcccata tgcttcgcct gctcccagcg tatcgtcctt ctcttctccc    600
atcgagccct ctacaccatc aactgccgct tactaccaaa gaaatcctgc gccgaacacc    660
ttccaaaacc caagcccctt ccccaaaaca tccacagcat ctcttccctc ccgggtcat     720
caacagatga tttctcccgt cacccccgcc tggcaacatc accactactt cccccccgtcc   780
agttccacgt cttaccagca gaaccatgat cgctacatct gccggacatg ccacaaggcc    840
ttttcgcggc cctccagcct gcgcatccac tcccacagcc acactggcga aagcctttc    900
cgttgcacac atgccggctg cggcaaggcc ttcagcgtac ggagcaatat gaagcgtcat    960
gagcgtggtt gccatacggg ccgcccagtt gctaccgcca tggtccaata g            1011
```

<210> SEQ ID NO 60
<211> LENGTH: 1005
<212> TYPE: DNA
<213> ORGANISM: Neosartorya fischeri

<400> SEQUENCE: 60

```
atggatgtcg caagcctcat ctcgccttct gaatcggata cagttccgac cttcaggtca     60
agatcgattc agaattcatc agccagccat acaagcgcc tctccgaaca atatacgggc    120
tcttacttct ctgctgcacc aacacatacg acgtcttact ctcgtacccc tcagccacca   180
ctgtcccctc cagccgagga ccagcccaaa tgctcgcttc cttccatctc gattctgctt   240
gagaacgcag acggtgccgc cgcacacgca gcaaaacgcc aaagaaccag tctatcaacg   300
cacagggatt cggggcctcc atatgactcg atcacaccac acgccatgcc accaacgccg   360
ccactgcgtc ctggttcggg cttccacagt aatggccatt ctccctcggc atcgtctgtc   420
tctgccacca gctccagcgc tgtgatgaag aacaccgaaa cgtattctca ggcgccaatt   480
gggcttccta gtccgacgga tcgatcctcg atctcgagcc aagggtccgt tcagcatgcc   540
gccggcgctc catatgcttc gcctgctccc agcgtgtcgt ccttctcttc tccgtcgag    600
ccctctacac catcaactgc cgcttactac aaagaaacc ctgcgccgaa caccttccaa    660
aacccaggct ccttccctcc aacatccgcg gcctctcttc cttccccggg tcatcaacag    720
atgatttctc ccgtcacccc cgcctggcaa catcaccact acttcccccc gtccagttcc    780
acgccttacc agcagaacca tgatcgctac atctgccgga catgccacaa ggccttctcg    840
```

| | |
|---|---|
| cggccatcca gcctgcgcat ccattcccac agccacactg gcgagaagcc tttccgctgc | 900 |
| acacatgccg gctgcggcaa ggcctttagc gtacggagca atatgaagcg tcacgagcgt | 960 |
| ggttgccata cgggccgccc ggttgctacc gccatggtcc aatag | 1005 |

<210> SEQ ID NO 61
<211> LENGTH: 960
<212> TYPE: DNA
<213> ORGANISM: Aspergillus flavus

<400> SEQUENCE: 61

| | |
|---|---|
| atggatctcg ccagccttat cactccgggt cctgaaccca tctacaagtc tcgggcatcc | 60 |
| tacagccctc ctcccagctc tgcgggttcc tacaagcgcc cggctgaaca cgactcttac | 120 |
| ttctcgtact cgcgcgcccc gcaagcccct ctttccccgc cagtcgagga ccagcccaag | 180 |
| tgctctcttc cctctatctc gactctcttg gaaggcgccg acagcgcatc gacatatgct | 240 |
| gcaaagcgtc aaagaaccag cccaccccccg cgcagggagt ctgagttccg ttcaccttat | 300 |
| gactcagtct caacaccaaa tggccctcct actccacctt gcgccctga atcgggcttc | 360 |
| cacagcggcc accactctcc ctctgcttcg tccgtgacta gtggaaaggc catcaagctc | 420 |
| gagtcgtact cgcaaacccc catgacactg cctagcccgt ccgatagatc ctcgatctcc | 480 |
| agccagggct ctgtccacca cgtttccgct gctccctacg cttctcctgc cccagtgtg | 540 |
| gcctcgtact cttcgccggt tgaatcctcg gctccgtccg ccatgtacta ccagagacct | 600 |
| tccggctcct accagacccc tgctactgtg cctagcccct ccgctgctcc tatgcctgca | 660 |
| tctgccacac accagcagat gattactccc gtcactccgg cctggcagca ccaccactac | 720 |
| ttcccgcctt ccagctcggc accctaccaa cagaaccacg accggtatat ctgccggact | 780 |
| tgccacaagg ccttctccag accatccagc ctgcgcatcc actctcacag ccacactggc | 840 |
| gagaagccat tccgctgcac ccacgccggc tgcggtaagg cgttcagcgt acgaagcaac | 900 |
| atgaagcgcc acgagcgcgg ctgccacacc ggacgccccg tcgccaccgc catggtataa | 960 |

<210> SEQ ID NO 62
<211> LENGTH: 960
<212> TYPE: DNA
<213> ORGANISM: Aspergillus terreus

<400> SEQUENCE: 62

| | |
|---|---|
| atggatctcg ccagcctaat caccccggga cctactccct tcgcatctcg tccgcctcga | 60 |
| gcttcctaca gtccccggc ttcttcgtcc ggttcataca aggcccctaa tgagcctcat | 120 |
| tatacggggt catacttccc cgccatgcct actgcgactc cagtgaccac cactacttcc | 180 |
| tactcgcgct cgccgcaacc gcctctctct cctcccgtcg aggaccagcc caagtgctct | 240 |
| ctcccttcca tctccaccct tctcggtgcc gcagacagcg ccccaatgcc cccagctaag | 300 |
| cgccagcgcc tcagtacccc cgcgcgcaga gaatccgata gctggctcca gacaacacca | 360 |
| tgcctgcctc cgacccccc gttgcgtcca ggctccggct tccacagcag cggccaccgc | 420 |
| tcgccatcat ccaacaagcc caccgaatcg gcgcccttcc cgcaacagcc cccgtgacg | 480 |
| ctccccagtc ccaccgagcg ctcctccatc tccagccagg gctccgcgca cgcgccgtac | 540 |
| gcttcgcccg ccccagcgt cgcctcgtac tcgtctcccg tcgagccctc cccggctccc | 600 |
| tccacgctgt actaccagcg ccccgccgcg cctccagcgc cttccgccgc cgcgctgct | 660 |
| cccgctcccg cgcagccctt gatctccccc gtcacccccgg cctggcagca ccaccactac | 720 |

```
ttcccgccct ccagctccac cccctaccag cagaaccatg accggtacat ctgccgtacc 780
tgccacaagg cattctcgcg cccctcgagt ctgcgcatcc attcgcacag tcacaccggc 840
gagaagccct tccgctgcac ccacgccggc tgcggcaagg ccttcagcgt ccgcagcaac 900
atgaagcgcc atgagcgcgg atgccacagc ggccgtccgg ttgctaccgc tatggtatga 960

<210> SEQ ID NO 63
<211> LENGTH: 906
<212> TYPE: DNA
<213> ORGANISM: Penicillium chrysogenum
<400> SEQUENCE: 63
atggatctct ccaacctcct ctctcacagc gcggctgtca agccgatcta tactcctgtc 60
gagtccagtt actataagcg ctcgccgcct ctgtcgccgc cagccgaaga gcccaaggtc 120
tcattgcctt caatctcgtc tctctttgag ggtgctgatg gtgctcagca cgcagctacc 180
tcgctaaccc taaaccttcc agagcgccaa cgcttgtcac catctctcgg tgaccgccat 240
gtccgggttc agtcctacga actgccccca acaccacctc tgcgccccgg ctctggccac 300
gcccaccgcc gcgcatctcc cgtggagtcg ctgtctcaca aggaagcaca ccagcatcac 360
cttcaccgtt cctctatctc cagcaacagc tcagtccaca tccctcgcaa cacagtaccc 420
tacgcctcgc ctgtaccaag cgtctcatcc tacacatctc cagtcgacgc tcctcaacag 480
ccaatgtact accctcgccc accaaccaca tcctccttcc agccctcaac accagcatca 540
gcaccccaga tgcccccctgt ccaggtccag acgcagcagc cgcactcgca ctctcactcg 600
tcttcggctc tcatctctcc tgtcaccccg gcctggcaac accaccacta cttcccgccc 660
tccaccacag ccccgtacca gcagaaccac gaccgctata tctgccgtac atgccacaag 720
gctttctcgc gcccttcctc cctgcgcatc cactcgcact cgcacactgg cgagaagccc 780
ttccgctgca cgcatgccgg ctgcggtaag gctttctccg tgcgcagtaa catgaagcgc 840
catgagcgtg gctgccattc tggtcgccct gcccctgccc ctgctgctac tgcgcttgtc 900
gtatag 906

<210> SEQ ID NO 64
<211> LENGTH: 1011
<212> TYPE: DNA
<213> ORGANISM: Coccidioides immitis
<400> SEQUENCE: 64
atgaacgttt caagcctgat cacttgcgat cagccgcacc aattgcgcgc gcctgcatct 60
tcatattctg agcaccgtcg atccccatcc atccccaagc ctttgcagac ggagagcagt 120
tcatgcgctt ctccatactc gcggttcgag cgtctccctc tttcaccgcc ggaggaggat 180
ggcaagacac agttctcact tccttctatc tcgtctcttc ttcggggcgt agatggtgtt 240
tctgatgcgc acgttgctaa gagacaacga accaaccctc ctcctagcat tgacttaggg 300
atggagagac ggactataga ccaaacatta aagcagaggc cagcgctgcc tttgacgcct 360
cctctaaggc ctgagtctgg catgaatagc acaagccagt cgccgtcaac atcatcgcca 420
ccacgaagcg ccatctcact accgagtctt gttcggagtt atccgtctcc agtttcagaa 480
gttccagagg gacgacggat gtcacagata tcgcgacatt cgcgaggggc ttcgacgtcg 540
caaacttctc aactttcagg cccagaaaca cgttacccat cgccaccaaa tgtcaactct 600
ccaacctttg ctgcccctgt tgaaccagcg ccaaagccga cagaatacta cccagccagc 660
cgaccggtaa cgtttccgcc tgtggcgttc gcagttctgc caagccagcc aactcatcct 720

| | |
|---|---|
| caggtgcttc ctcttggaag tcctgcgtgg cagcaccatc attatttccc tccttccaac | 780 |
| acagcaactt atcctctcaa tcacgataga tacatctgcc gaatatgtca taaggctttc | 840 |
| tcaagaccgt ccagcctgcg aatacactcc cacagtcata ctggcgagaa gcctttccgg | 900 |
| tgcccccatg ccggctgtgg gaaagcgttt agcgtgcgaa gcaacatgaa gcgacacgaa | 960 |
| aggggttgcc atcctggaag atcagcacca ccatcggccc tggttaactg a | 1011 |

<210> SEQ ID NO 65
<211> LENGTH: 1038
<212> TYPE: DNA
<213> ORGANISM: Ajellomyces capsulatus

<400> SEQUENCE: 65

| | |
|---|---|
| atgaatttat cccacttggt gaccagctat catagccctc cttcgacgta tccacactca | 60 |
| ggcacttcgc aaaagcgcca gtccttgcag agcgaatctt cattatctgt atcgaacgga | 120 |
| tactacgatc gcaatgcttc aaatcttgca tatgcccgct ctcctcaacc acccttatcc | 180 |
| ccacctgtcg aagagcagtc cagattctct cttccttcaa tatctagttt attgcaagga | 240 |
| gctgaccaac tctctcctgt tcatatagct aaaaaacatc gtcccaatcc actctcaact | 300 |
| ggagaagttg atttaaaatc gcagggccat ggagccaccc aaaagcccat acacaggccg | 360 |
| agaatgattt taccaccgac ccctcccatg cgcccaggct ccggattaga tggaagaaat | 420 |
| cactctcctg ccggatcgtc gccatcgtct gcacactctc ccatttcagt agccaatctc | 480 |
| acaagttcgt catcggcgga cccttcctat cagcatcgga tgccccaagg tccgttaccc | 540 |
| ccacagtcaa ccagatcgtc cgtatctcaa aattctcctg tctctctacc cgaaaagcat | 600 |
| tacgctccat cctccaattt acccaccagc tcgactccat tcgcttcccc agttgaaccc | 660 |
| ctagcgaatt ctacggaata ttatcaccgc ccatcccatc cccttctttt ctcgacatct | 720 |
| attcctctgg cagccccgcc agcgcaacag caccatcacc attctatgat ctcaacctgg | 780 |
| caacaccacc actattttcc accgtcaaat acggctccct acccacaaaa tcatgacagg | 840 |
| tatatctgtc gaatatgtca caaggcgttt tctcggcctt ctagtctgcg gattcactcg | 900 |
| cacagccata ccggcgaaaa gccattcaaa tgcccgcatg tcaactgtgg caagtcattt | 960 |
| agtgtcagga gtaacatgaa gcgacatgaa cggggttgtc atacaggcag acctacgcaa | 1020 |
| gcagctttgg tgaattaa | 1038 |

<210> SEQ ID NO 66
<211> LENGTH: 1272
<212> TYPE: DNA
<213> ORGANISM: Uncinocarpus reesii

<400> SEQUENCE: 66

| | |
|---|---|
| atgaacgttt ctagcctgat tagttgtgat cagactgctc ccttccacgg gtctgcaaca | 60 |
| tcatatttcg agcatcatca aagaatccga tcgccttcca ttcccaaaag atcacacgaa | 120 |
| gagaacagct catccgcctc tccctaccct ccttttgcaa ccctgcctct ttcgccacca | 180 |
| gaagatgacg ggaagacaac cttctcgctt ccttctatct catcccttct tcaaagcgtc | 240 |
| gacgctgctt ctgacactca cgttgccaaa cggcaacgag ccaaccccc tcctagcatt | 300 |
| gatttagctc tggagagacg aggtgcctgt gcggaccaag caatcagaca aaggccagcc | 360 |
| cttccactaa cgcctcccct gcgaccagag tcgggaatgg gcggtgtaaa tcactcgcca | 420 |
| tctgcatcat cccctccccg aaccgctatc tcactaccca gcctcattgg aagttaccca | 480 |

```
tcgccagttt cagaggctcc agaaggacga cgaatgtcgc aaatctcacg acactcaagc      540
agaacttcca tctctcaatc ctcccaacat ccagggccgg aagcccgcta cccatcgcca      600
ccaactctca gctctccttc cttcgccgct cctattgaac cacctccaaa gccagagtac      660
tactcttctg gtgcccgacc gaccaacttt ccgccagtaa ctttcgctgt ccttccaagt      720
caaccaacgc atccgcagat ggtggccttg gggagtcctg cctggcagca tcaccactac      780
tttcctccat caaacacagc aacttaccca ctcaaccacg acagatacat ttgccgaata      840
tgccacaagg cattctcacg gccgtcaagc ctgcgaattc actcgcatag tcacacaggc      900
gagaagccgt ttcgatgccc ccatgccggc tgcgggaagg cattcagcgt gcgaaatcag      960
ccccgcagcc agcgctcgtt aattgaaaaa cggaaggggt acgcgatcgg atttgacgaa     1020 tgggtttga cgatgataac gcccacaata cggagtacca acgagcaaat ctacacaact     1080
gcatcgtgta agatcgcgaa cgtggcggtg atcaacatca atagaagaat tgccgagctt     1140
cgcaagtcat ttcgcaacag acgttcgaat gggacgttgt ccccgacgaa gcgccgcgtc     1200
aaattggcat tttccctgga ttgccaatct acatcctcat ccaggcttgc ccttttaccg     1260
cagtcccttt ga                                                        1272

<210> SEQ ID NO 67
<211> LENGTH: 744
<212> TYPE: DNA
<213> ORGANISM: Penicillium marneffei

<400> SEQUENCE: 67
atggataacg tgcctgcaag caaacgtgcc cgccatgact caggcgacta cagccgtggc       60 ttcttaccte caacaccgcc aatgcgcccc tgctccgggt tcacagaagg cagctcgcct      120
gcctctcttc cttctggacg atcacattct gcttctataa gcagcgcagt ttcgcatcca      180
tcacaccaac agcgtacatc tttaccatct atttctgcat ctcttcaaaa tacaccaatc      240
cacccttcag agcgtttatc catctcctct ctcgcctctc acgactcttc ccgccttttct     300 cacgccattc ccagcccttc atctaccaca gcctcgatca caaccacagc gactccatca      360
acgtcatatt attctacatc agaagagaaa gcatatccac gatcacatag cacatccgct      420
ccagtgaccc catcaacact tgtcccacca ccaccccgcca tgctctcgcc tgtgaaccac      480
ccaggctggc aacaccacca ctacttccca cttcgactacg gacatcata cccacaaaac      540 cacgagcggt atgtctgccg tacatgccac aaggcattct ctcgtccatc cagtcttcga      600
atccactcgc atagccacac tggcgagaag ccattccgat gcacacatgc aggctgcgga      660
aaggcgttca gtgtgcgcag caatatgaag cgccacgagc gcggctgtca tagcggacga      720
cctatgacgg caactgttgt ctaa                                            744

<210> SEQ ID NO 68
<211> LENGTH: 954
<212> TYPE: DNA
<213> ORGANISM: Botryotinia fuckeliana

<400> SEQUENCE: 68
atggcctcat cgttggtttc aaacccttat acagtccatc ctatggctca acactcttcc       60
tacacatacg ttaacgcacc tcaaccacca ccctcaccac ccgtagacga aacttcaaag      120
tgttccctac catctatttc aagtctgttg ggtttggccg atggatcgag tccaacagag      180
caggctcagc aacagtcatc gccacaacaa gcagctttca aggaagatta tagaccagag      240
tctggacatc agtacggtcc ttcctcatca atgagctctc gaggtgctct tccacctaca      300
```

```
ccccccaatgc aatctgacgg tggattcgac ggcagacaat cgccgtctca agcatctact    360
tcatcatatt cagtagtttc tgcgccaaat tattacttta atccttctca agtctcggcc    420
atcaacaata tggagcctca tgcacaacgc cagccagtcc aaactgttac tcgaagagtt    480
tcaatgccag tgtcttcaat gcaatatggc cattctccgt tcaacggatc ctacactatg    540
tctcctggcg cccagtcttt gagctcttac tatccaagcc cgatacaaac acaatctccc    600
caagtttctt cactatacta tcaaagacca cttccacagc aatttcctcc gccaatgatg    660
ccagtgtctg tgactctgac tccatcatcc ggtgctaatc catggcaaca tcatcactat    720
atctctcctt cctcagcagc ctcatttcct cagtcacaag atagatacat ctgtcagact    780
tgtaacaaag cttttcgag accatcgagt ctccgaatcc acagccactc acataccggc    840
gagaaaccct tcaagtgtcc acatcaaaac tgtgggaaag ccttcagcgt taggagcaac    900
atgaagagac acgagcgagg ttgtcacagt tttgaaagcg cttcaatggt ctga          954
```

<210> SEQ ID NO 69
<211> LENGTH: 918
<212> TYPE: DNA
<213> ORGANISM: Neurospora tetrasperma

<400> SEQUENCE: 69

```
atggcaccca cgacgttaac gcctcaatat cctgcccagc cttatggctt cgctccgcca     60
ccctcccctc ctttggacga ctccaacaag tgctccctgc cctcgatttc gaacctgctt    120
gtcatggccg atcagggatc tcctacctca gagacatctc ctcagtctca gcaattgcac    180
ttctcaaagc ctgacaaccg tcccaactct tcccagtttg gcaacccagc atcgatcagg    240
gcgaacctcc cccctagtcc tcccatgtct tcggaagctt cttttgaagg ataccgctct    300
ccttcaagca agccagcaag ccagtctcag ggcagctcca actactacta tgagaccacg    360
ccgcctttga gccagcatga agccgactcc cggcagatgg ccactgctgc acccagagcc    420
cctgttcagt catcaacctt ccaaacacag taccgtcgt cagccggcta ctcgagtcag    480
tcaggcatga acccttatta ccctcccatg cagccgacac cccctccgca gcagcagatg    540
tcgggcttgt attatcagcg accactccct cagactttca cccctgctgt gccagttcca    600
gtcactctcg caccagtcac gggagccaac ccttggcaac atcaccacta tattgctcct    660
tcttccactg catcttttcc gcagtctcaa gaccggtaca tctgccagac ttgcaacaag    720
gccttctctc gaccgagctc attgcgaatc acagccact ctcacactgg tgagaagcct    780
ttcaagtgcc cccatgcagg ctgcggaaag gccttcagcg ttcgcagtaa catgaagcgt    840
catgagcgtg gctgccacag ttttgagagc agcaacggca gaagcagtgg caacagcaac    900
aacggcgcat ctgcctag                                                   918
```

<210> SEQ ID NO 70
<211> LENGTH: 918
<212> TYPE: DNA
<213> ORGANISM: Neurospora crassa

<400> SEQUENCE: 70

```
atggcaccca cgacgttaac gcctcaatat cctgcccagc cttatggctt cgctccgcca     60
ccctcccctc ctttggacga ctccaacaag tgctctctac cctcgatttc gaacctgctt    120
gtcatggccg atcagggatc tcctacctca gagacatctc ctcagtctca gcaattgcac    180
ttctcaaagc ctgacaaccg tcccaactct tcccagtttg gcaacccagc atcgatcagg    240
```

```
gcgaacctcc cccctagtcc tcccatgtct tcggaagctt cttttgaagg ataccgctct    300
ccttcgagca agccagcaag ccagtctcag ggcagctcca actactacta tgagaccacg    360
ccgcctttga gccagcatga agccgactcc cggcagatgg ccactgctac acctagagcc    420
cctgttcagt catcaacctt ccaaacacag tacccgtcgt cagccggcta ctcgagtcag    480
tcaggcatga acccttatta tcctcccatg cagccgacac cccctccgca gcagcagatg    540
tcgggcttgt attatcagcg accactccct cagactttca cccctgctgt gccagttcca    600
gtcactctcg caccagtcac gggagccaac ccttggcaac atcaccacta tattgctcct    660
tcttccactg catctttttcc gcagtctcaa gaccggtaca tctgccagac ttgcaacaag    720
gccttctctc gacccagctc attgcgaatc acagccact ctcacactgg tgagaagcct    780
ttcaagtgcc cccatgcagg ctgcggaaag gccttcagcg ttcgcagtaa catgaagcgt    840
catgagcgtg gctgccacag ttttgagagc agcaacggca gagcagtgg caacagcaac    900
aacagcgcat ctgcctag                                                  918

<210> SEQ ID NO 71
<211> LENGTH: 930
<212> TYPE: DNA
<213> ORGANISM: Magnaporthe oryzae

<400> SEQUENCE: 71
atggccgcca ccatgataca acagccctac ccaattcatc agcagcagtc gcagtacagc     60
tacatggttc agcctcaggg cccgccttcg ccgcccatgg acgacaacaa gtgctcgctt    120
ccatccatct cgaacctgct cggcttggcg gatcaaggat caccaacctc ggagacctcg    180
gcccaattcc gcgaggagca gaagcaacaa caagcagcac aacaatcaag acccaactcg    240
tcacactata gcaatgcagt ccagtctgtg cgccagggca tcccgccaac gccgccaatg    300
acttctgaga cctcattcga cggttacaac tcgccctcaa acaagtcggt cagccagctt    360
cccgccactg gctactactt tgaggcgacg ccacccccag gccacatgga gatggagccc    420
cgcccgcaca tgaccagcgt tccagggtc ccagttcagg ctccttcgc tcagtctgcc    480
tactcagctc cctatggcat ggccccagc aacccgatgg cggcctacta cccgacgatg    540
cagcccacgc ctcctcctca gcagcctcag atctctagcc tttactacca gagacccctt    600
cctcaggcct ccctcccat gctgtcaac gtctccatgg gtcctcagtc tggcgccaac    660
ccgtggcagc accaccacta catctcgcca tctgctgcgg catctttccc tcagtcccag    720
gaccgctaca tctgccagac ctgcaacaag gcattctccc gcccgagctc cttgaggata    780
cacagccact cgcacactgg cgagaagcct ttcaagtgcc ctcacgccgg ctgcggcaag    840
gctttcagcg tgcgcagcaa catgaagcgc acgagagggg ctgccacaa ctatgacagc    900
agcagcagca acggcaccgc catgcactga                                    930

<210> SEQ ID NO 72
<211> LENGTH: 1029
<212> TYPE: DNA
<213> ORGANISM: Chaetomium globosum

<400> SEQUENCE: 72
atggcaaaca caatggtcac acactacgcg cacgtacctc aacatagcct tcagtatggc     60
tacatgccgc caccttcacc gccaatggat gaggcggcaa agtgctcgct cccctctatc    120
tcgaacctcc tcgggcttgc agaccaagga tcgccgactt cggaaacgtc gccccagtcc    180
cagcagcagc aacaggcgca gcagcagcag caacagcaat gtatgagcag ctcgtggtgg    240
```

```
gatatgggac acctagatac tgactcgacc ccagcgcaag gatccaagcc ggagacgagg    300
cccaactctt cgcattacac caacccggta accattcgga caggactccc gcccagcccg    360
cccatgtcct cggatgcatc ctttgaaggt ttcaactcgc catcgaccag gtcggtgagc    420
caggtgccga acgggtcaaa ctacttcttt gagacaacgc caccgcttca gatggaagcc    480
gatgcacggc agatgaccgc tgccgccgcc gtcccgcgag tttctgtcca ggcttcagcc    540
taccagcccc agtacgctcc cggccctgcg tacatgagtc aaccagccat gacctcatac    600
tatcctccga tgcaatccgc ggcgccaccg cagacgcaaa tgtccggcct ctactaccaa    660
cgaccgcttc ctcagtcttt tccgcctccg atgtccatgt ctatgactct tgcgccgacg    720
gccgggaacc cctggcagca ccatcactac attgcccctt cggcgtcagc atcctttccc    780
cagagccagg accggtatat ctgcccgacg tgcagcaaag ccttctcgcg gcccagctcg    840
ctgcggatcc acagccactc gcacacgggc gagaagccct tcaagtgccc gttcccgggt    900
tgcggcaagg ccttcagtgt gcgcagcaac atgaagcggc acgaacgtgg gtgccacaac    960
tacgacagca gcagcacgac gagcagcacc ggcaccatga acagcaacac cggggggaagc   1020 cgtccctga                                                           1029

<210> SEQ ID NO 73
<211> LENGTH: 831
<212> TYPE: DNA
<213> ORGANISM: Fusarium oxysporum

<400> SEQUENCE: 73
atggaggaac aaaagtgctc tctaccctca atctcgaacc tcttgggttt ggccgatgcc     60
ggctcaccca cgagtgagtc ctcaccaact tcacggcaac attctcctcg ctttgaagtt    120
cctccacctt cacatggtca tagccgagct ggatctgaat gggctaaatc atcgcaccgt    180
gggcttcccc ctacaccacc tatgagcaca gacgcatctt tcgaaggcta cagctccccc    240
acaaggaaac catccaacca ggcgtatcca ggctcagcac aagaacata ctattacgag     300 accacaccac ctctagaagc cgatgcacag cgtcaggcat cagtaacggc tattcctcga    360
gcaacacctc cagcaacggc tccttatcct cagcaagctc accccacggt atacgccaac    420
ccagcaccag tgggcgctta ttacccggcg gcacaggtgc ctcctgctgt ccagcctcaa    480
gagatgaacc cttactacca gcgccctctc ccacaggctt atccccacc agtgagcatg    540 ccagcacctg ctccctcggg agcaaatcct tggcagcacc atcactatct taacccaact    600
ggagcggcgg cattcccgca aagccaggac cggtatattt gcccgacttg caacaaagcc    660
tttagcaggc ccagcagtct ccgaatccac agtcactcac ataccggaga gaaacccttc    720
aagtgtcccc atgctggatg tggcaaggct ttcagcgtac gcagcaacat gaaacgtcat    780 gagagggct gtcacagctt cgaatttaat gggtctgtga ttcggggttg a              831

<210> SEQ ID NO 74
<211> LENGTH: 311
<212> TYPE: PRT
<213> ORGANISM: Aspergillus nidulans

<400> SEQUENCE: 74

Met Asp Leu Ala Asn Leu Ile Ser Gln Pro Gly Pro Glu Pro Ala Leu
1               5                   10                  15

Thr Ala Lys Ser Arg Tyr Ser Pro Pro Ala Phe Glu Pro Gly Ser Phe
            20                  25                  30
```

Tyr Ala Ala Ser Thr Ser Phe Thr Arg Thr Gln Ala Pro Leu Ser Pro
            35                  40                  45

Pro Val Glu Asp Arg Ser Arg Cys Ser Leu Pro Ser Ile Ser Ala
 50                  55                  60

Leu Leu Asp Ser Ala Asp Gly Ala Ser Thr Gln Ala Pro Lys Arg Gln
 65                  70                  75                  80

Arg Leu Ser Ser Pro Met His Arg Glu Pro Leu Asp Lys Asn Pro Ser
                 85                  90                  95

Ala Gly Ala Ala Pro Ile Arg Leu Pro Pro Thr Pro Pro Leu Arg Pro
                100                 105                 110

Gly Ser Gly Phe His Ser Ala Gly His Ser Pro Ser Ser Ser Ile Ser
            115                 120                 125

Ser Ile Ser Met Ile Lys Ser Glu Tyr Pro Ala Pro Pro Ser Ala Pro
130                 135                 140

Val Ser Leu Pro Gly Leu Pro Ser Pro Thr Asp Arg Ser Ser Ile Ser
145                 150                 155                 160

Ser Gln Gly Ser Ala Pro Gln His Gln His Gly Pro Tyr Ala Ser Pro
                165                 170                 175

Ala Pro Ser Val Ala Pro Ser Tyr Ser Ser Pro Val Glu Pro Ser Pro
            180                 185                 190

Ser Ser Ala Met Tyr Tyr Gln His Gln Arg Pro Ala Ser Ser Gly Thr
            195                 200                 205

Tyr Gln Ala Pro Pro Pro Pro Gln His Gln Pro Met Ile Ser Pro
            210                 215                 220

Val Thr Pro Ala Trp Gln His His Tyr Phe Pro Pro Ser Ser Asn
225                 230                 235                 240

Thr Pro Tyr Gln Gln Asn His Asp Arg Tyr Ile Cys Arg Thr Cys His
                245                 250                 255

Lys Ala Phe Ser Arg Pro Ser Ser Leu Arg Ile His Ser His Ser His
                260                 265                 270

Thr Gly Glu Lys Pro Phe Arg Cys Thr His Ala Gly Cys Gly Lys Ala
            275                 280                 285

Phe Ser Val Arg Ser Asn Met Lys Arg His Glu Arg Gly Cys His Thr
290                 295                 300

Gly Arg Ala Val Ala Met Val
305                 310

<210> SEQ ID NO 75
<211> LENGTH: 319
<212> TYPE: PRT
<213> ORGANISM: Aspergillus terreus

<400> SEQUENCE: 75

Met Asp Leu Ala Ser Leu Ile Thr Pro Gly Pro Thr Pro Phe Ala Ser
 1               5                  10                  15

Arg Pro Pro Arg Ala Ser Tyr Ser Pro Pro Ala Ser Ser Ser Gly Ser
                20                  25                  30

Tyr Lys Ala Pro Asn Glu Pro His Tyr Thr Gly Ser Tyr Phe Pro Ala
            35                  40                  45

Met Pro Thr Ala Thr Pro Val Thr Thr Thr Ser Tyr Ser Arg Ser
 50                  55                  60

Pro Gln Pro Pro Leu Ser Pro Val Glu Asp Gln Pro Lys Cys Ser
 65                  70                  75                  80

Leu Pro Ser Ile Ser Thr Leu Leu Gly Ala Ala Asp Ser Ala Pro Met
                 85                  90                  95

Pro Pro Ala Lys Arg Gln Arg Leu Ser Thr Pro Ala Arg Arg Glu Ser
            100                 105                 110

Asp Ser Trp Leu Gln Thr Thr Pro Cys Leu Pro Pro Thr Pro Pro Leu
        115                 120                 125

Arg Pro Gly Ser Gly Phe His Ser Ser Gly His Arg Ser Pro Ser Ser
    130                 135                 140

Asn Lys Pro Thr Glu Ser Ala Pro Phe Pro Gln Gln Pro Pro Val Thr
145                 150                 155                 160

Leu Pro Ser Pro Thr Glu Arg Ser Ser Ile Ser Ser Gln Gly Ser Ala
                165                 170                 175

His Ala Pro Tyr Ala Ser Pro Ala Pro Ser Val Ala Ser Tyr Ser Ser
            180                 185                 190

Pro Val Glu Pro Ser Pro Ala Pro Ser Thr Leu Tyr Tyr Gln Arg Pro
        195                 200                 205

Ala Ala Pro Pro Ala Pro Ser Ala Ala Ala Ala Pro Ala Pro Ala
    210                 215                 220

Gln Pro Leu Ile Ser Pro Val Thr Pro Ala Trp Gln His His His Tyr
225                 230                 235                 240

Phe Pro Pro Ser Ser Ser Thr Pro Tyr Gln Gln Asn His Asp Arg Tyr
                245                 250                 255

Ile Cys Arg Thr Cys His Lys Ala Phe Ser Arg Pro Ser Ser Leu Arg
            260                 265                 270

Ile His Ser His Ser His Thr Gly Glu Lys Pro Phe Arg Cys Thr His
        275                 280                 285

Ala Gly Cys Gly Lys Ala Phe Ser Val Arg Ser Asn Met Lys Arg His
    290                 295                 300

Glu Arg Gly Cys His Ser Gly Arg Pro Val Ala Thr Ala Met Val
305                 310                 315

<210> SEQ ID NO 76
<211> LENGTH: 319
<212> TYPE: PRT
<213> ORGANISM: Aspergillus flavus

<400> SEQUENCE: 76

Met Asp Leu Ala Ser Leu Ile Thr Pro Gly Pro Glu Pro Ile Tyr Lys
1               5                   10                  15

Ser Arg Ala Ser Tyr Ser Pro Pro Ser Ser Ala Gly Ser Tyr Lys
            20                  25                  30

Arg Pro Ala Glu His Asp Ser Tyr Phe Ser Tyr Ser Arg Ala Pro Gln
        35                  40                  45

Ala Pro Leu Ser Pro Pro Val Glu Asp Gln Pro Lys Cys Ser Leu Pro
    50                  55                  60

Ser Ile Ser Thr Leu Leu Glu Gly Ala Asp Ser Ala Ser Thr Tyr Ala
65                  70                  75                  80

Ala Lys Arg Gln Arg Thr Ser Pro Pro Arg Arg Glu Ser Glu Phe
                85                  90                  95

Arg Ser Pro Tyr Asp Ser Val Ser Thr Pro Asn Gly Pro Pro Thr Pro
            100                 105                 110

Pro Leu Arg Pro Glu Ser Gly Phe His Ser Gly His His Ser Pro Ser
        115                 120                 125

Ala Ser Ser Val Thr Ser Gly Lys Ala Ile Lys Leu Glu Ser Tyr Ser
    130                 135                 140

Gln Thr Pro Met Thr Leu Pro Ser Pro Ser Asp Arg Ser Ser Ile Ser

```
            145                 150                 155                 160
Ser Gln Gly Ser Val His His Val Ser Ala Ala Pro Tyr Ala Ser Pro
                165                 170                 175

Ala Pro Ser Val Ala Ser Tyr Ser Ser Pro Val Glu Ser Ser Ala Pro
                180                 185                 190

Ser Ala Met Tyr Tyr Gln Arg Pro Ser Gly Ser Tyr Gln Thr Pro Ala
                195                 200                 205

Thr Val Pro Ser Pro Ser Ala Ala Pro Met Pro Ala Ser Ala Thr His
            210                 215                 220

Gln Gln Met Ile Thr Pro Val Thr Pro Ala Trp Gln His His Tyr
225                 230                 235                 240

Phe Pro Pro Ser Ser Ser Ala Pro Tyr Gln Gln Asn His Asp Arg Tyr
                245                 250                 255

Ile Cys Arg Thr Cys His Lys Ala Phe Ser Arg Pro Ser Ser Leu Arg
                260                 265                 270

Ile His Ser His Ser His Thr Gly Glu Lys Pro Phe Arg Cys Thr His
                275                 280                 285

Ala Gly Cys Gly Lys Ala Phe Ser Val Arg Ser Asn Met Lys Arg His
            290                 295                 300

Glu Arg Gly Cys His Thr Gly Arg Pro Val Ala Thr Ala Met Val
305                 310                 315

<210> SEQ ID NO 77
<211> LENGTH: 335
<212> TYPE: PRT
<213> ORGANISM: Aspergillus clavatus

<400> SEQUENCE: 77

Met Asp Leu Ala Asn Leu Ile Ser His Pro Thr Ser Glu Ala Ala Ser
1               5                   10                  15

Thr Phe Lys Ser Arg Ser Ala Gln Ser Pro Ala Phe Gln Ala Asn
                20                  25                  30

Pro Tyr Lys Arg Leu Ser Gly Ser Ser Met Ser Ser Tyr Phe Thr Ser
                35                  40                  45

Val Pro Thr Thr Ala Thr Ser Tyr Ser Arg Thr Pro Gln Pro Pro Leu
            50                  55                  60

Ser Pro Pro Val Asp Asp Arg Pro Arg Cys Ser Leu Pro Ser Ile Ser
65                  70                  75                  80

Thr Leu Leu Glu Gly Ala Asp Ser Ala Ala Ala His Ala Ala Lys Arg
                85                  90                  95

Gln Arg Thr Ser Leu Ser Ala His Arg Asp Leu Asp Ala Arg Pro Gln
                100                 105                 110

Ser Gln Pro Tyr Asp Thr Ile Thr Pro His Ala Leu Pro Pro Thr Pro
                115                 120                 125

Pro Leu Arg Pro Gly Ser Gly Phe Arg Ser Asn Gly His Ser Pro Ser
            130                 135                 140

Ala Ser Ser Val Ser Ala Thr Ser Ala Ser Thr Val Ile Lys Thr Glu
145                 150                 155                 160

Thr Tyr Pro Gln Pro His Ile Gly Leu Pro Ser Pro Thr Asp Arg Ser
                165                 170                 175

Ser Ile Ser Ser Gln Gly Ser Val Gln His Ala Pro Gly Ala Pro Tyr
                180                 185                 190

Ala Ser Pro Ala Pro Ser Val Ala Ser Tyr Ser Ser Pro Val Glu Pro
                195                 200                 205
```

```
Ser Thr Pro Ser Ser Ala Ala Tyr Tyr Gln Arg Lys Ala Pro Ser Ala
    210                 215                 220

Pro Phe Gln Asn Pro Gly Ser Val Pro Ser Ala Ser Ala His Gln
225                 230                 235                 240

Gln Leu Ile Thr Pro Ile Thr Pro Ala Trp Gln His His Tyr Phe
                245                 250                 255

Pro Pro Ser Ser Ser Thr Ala Tyr Gln Gln Asn His Asp Arg Tyr Ile
                260                 265                 270

Cys Arg Thr Cys His Lys Ala Phe Ser Arg Pro Ser Ser Leu Arg Ile
            275                 280                 285

His Ser His Ser His Thr Gly Glu Lys Pro Arg Cys Thr His Ala
    290                 295                 300

Gly Cys Gly Lys Ala Phe Ser Val Arg Ser Asn Met Lys Arg His Glu
305                 310                 315                 320

Arg Gly Cys His Thr Gly Arg Pro Val Ala Thr Ala Met Val Ser
                325                 330                 335
```

<210> SEQ ID NO 78
<211> LENGTH: 336
<212> TYPE: PRT
<213> ORGANISM: Aspergillus fumigatus

<400> SEQUENCE: 78

```
Met Asp Val Ala Ser Leu Ile Ser Pro Ser Glu Ser Asp Thr Val Pro
1               5                   10                  15

Thr Phe Arg Ser Arg Ser Ile Gln Asn Ser Ser Ala Ser His Tyr Lys
            20                  25                  30

Arg Leu Ser Glu Gln Ser Thr Gly Ser Tyr Phe Ser Ala Val Pro Thr
        35                  40                  45

His Thr Thr Ser Tyr Ser Arg Thr Pro Gln Pro Leu Ser Pro Pro
    50                  55                  60

Ala Glu Asp Gln Ser Lys Cys Ser Leu Pro Ser Ile Ser Ile Leu Leu
65                  70                  75                  80

Glu Asn Ala Asp Gly Ala Ala His Ala Ala Lys Arg Gln Arg Asn
            85                  90                  95

Ser Leu Ser Thr His Arg Asp Ser Asp Pro Arg Pro Tyr Asp Ser
        100                 105                 110

Ile Thr Pro His Ala Met Pro Pro Thr Pro Pro Leu Arg Pro Gly Ser
        115                 120                 125

Gly Phe His Ser Asn Gly His Ser Pro Ser Thr Ser Ser Val Ser Ala
    130                 135                 140

Ala Ser Ser Ser Ala Leu Met Lys Asn Thr Glu Ser Tyr Pro Gln Ala
145                 150                 155                 160

Pro Ile Gly Leu Pro Ser Pro Thr Asp Arg Ser Ser Ile Ser Ser Gln
                165                 170                 175

Gly Ser Val Gln His Ala Ala Ser Ala Pro Tyr Ala Ser Pro Ala Pro
            180                 185                 190

Ser Val Ser Ser Phe Ser Ser Pro Ile Glu Pro Ser Thr Pro Ser Thr
        195                 200                 205

Ala Ala Tyr Tyr Gln Arg Asn Pro Ala Pro Asn Thr Phe Gln Asn Pro
    210                 215                 220

Ser Pro Phe Pro Gln Thr Ser Thr Ala Ser Leu Pro Ser Pro Gly His
225                 230                 235                 240

Gln Gln Met Ile Ser Pro Val Thr Pro Ala Trp Gln His His His Tyr
                245                 250                 255
```

```
Phe Pro Pro Ser Ser Ser Thr Ser Tyr Gln Gln Asn His Asp Arg Tyr
            260                 265                 270

Ile Cys Arg Thr Cys His Lys Ala Phe Ser Arg Pro Ser Ser Leu Arg
        275                 280                 285

Ile His Ser His Ser His Thr Gly Glu Lys Pro Phe Arg Cys Thr His
    290                 295                 300

Ala Gly Cys Gly Lys Ala Phe Ser Val Arg Ser Asn Met Lys Arg His
305                 310                 315                 320

Glu Arg Gly Cys His Thr Gly Arg Pro Val Ala Thr Ala Met Val Gln
                325                 330                 335

<210> SEQ ID NO 79
<211> LENGTH: 319
<212> TYPE: PRT
<213> ORGANISM: Aspergillus oryzae

<400> SEQUENCE: 79

Met Asp Leu Ala Ser Leu Ile Thr Pro Gly Pro Glu Pro Ile Tyr Lys
1               5                   10                  15

Ser Arg Ala Ser Tyr Ser Pro Pro Ser Ser Ala Gly Ser Tyr Lys
            20                  25                  30

Arg Pro Ala Glu His Asp Ser Tyr Phe Ser Tyr Ser Arg Ala Pro Gln
        35                  40                  45

Ala Pro Leu Ser Pro Pro Val Glu Asp Gln Pro Lys Cys Ser Leu Pro
    50                  55                  60

Ser Ile Ser Thr Leu Leu Glu Gly Ala Asp Ser Ala Ser Thr Tyr Ala
65                  70                  75                  80

Ala Lys Arg Gln Arg Thr Ser Pro Pro Arg Arg Glu Ser Glu Phe
                85                  90                  95

Arg Ser Pro Tyr Asp Ser Val Ser Thr Pro Asn Gly Pro Pro Thr Pro
            100                 105                 110

Pro Leu Arg Pro Glu Ser Gly Phe His Ser Gly His His Ser Pro Ser
        115                 120                 125

Ala Ser Ser Val Thr Ser Gly Lys Ala Ile Lys Leu Glu Ser Tyr Ser
130                 135                 140

Gln Thr Pro Met Thr Leu Pro Ser Pro Ser Asp Arg Ser Ser Ile Ser
145                 150                 155                 160

Ser Gln Gly Ser Val His His Val Ser Ala Ala Pro Tyr Ala Ser Pro
                165                 170                 175

Ala Pro Ser Val Ala Ser Tyr Ser Pro Val Glu Ser Ser Ala Pro
            180                 185                 190

Ser Ala Met Tyr Tyr Gln Arg Pro Ser Gly Ser Tyr Gln Thr Pro Ala
        195                 200                 205

Thr Val Pro Ser Pro Ser Ala Ala Pro Met Pro Ala Ser Ala Thr His
    210                 215                 220

Gln Gln Met Ile Thr Pro Val Thr Pro Ala Trp Gln His His His Tyr
225                 230                 235                 240

Phe Pro Pro Ser Ser Ala Pro Tyr Gln Gln Asn His Asp Arg Tyr
                245                 250                 255

Ile Cys Arg Thr Cys His Lys Ala Phe Ser Arg Pro Ser Ser Leu Arg
            260                 265                 270

Ile His Ser His Ser His Thr Gly Glu Lys Pro Phe Arg Cys Thr His
        275                 280                 285

Ala Gly Cys Gly Lys Ala Phe Ser Val Arg Ser Asn Met Lys Arg His
```

```
              290                 295                 300
Glu Arg Gly Cys His Thr Gly Arg Pro Val Ala Thr Ala Met Val
305                 310                 315

<210> SEQ ID NO 80
<211> LENGTH: 325
<212> TYPE: PRT
<213> ORGANISM: Aspergillus niger

<400> SEQUENCE: 80

Met Asp Leu Ala Ser Leu Ile Ser His Pro Gly Pro Asp Pro Ile Met
1               5                   10                  15

Lys Ser Arg Ala Ser Tyr Ser Pro Pro Met Thr Ser Tyr Lys Arg Ser
            20                  25                  30

Ile Glu His Thr Ser Asp Ser Tyr Phe Pro Ser Val Pro Ile Ser Tyr
        35                  40                  45

Thr Arg Ser Pro Gln Pro Pro Leu Ser Pro Pro Val Glu Asp Gln Ser
    50                  55                  60

Pro Lys Cys Ser Leu Pro Ser Ile Ser Thr Leu Leu Glu Gly Ala Asp
65                  70                  75                  80

Gly Ala Ala Met His Ala Ala Lys Arg Thr Arg Met Thr Pro Pro Leu
                85                  90                  95

Gln Arg Asp Leu Asp Ser Arg Gln Ser Gln Ala Tyr Asp Leu Lys
            100                 105                 110

Ala Asn Gly Pro Gln Ile Ala Leu Pro Pro Thr Pro Pro Leu Arg Pro
        115                 120                 125

Gly Ser Ser Phe His Ser Ala Gly His Ser Pro Ala Ser Ser Ile Ser
    130                 135                 140

Ala Ala Ser Asp Ala Ala Ala Pro Lys Arg Ser Asp Ser Tyr Pro Gln
145                 150                 155                 160

Val Pro Met Ala Leu Pro Ser Pro Ser Asp Arg Ser Ser Ile Ser Ser
                165                 170                 175

Gln Gly Ser Val Gln Gly Val Ser Ser Ala Ser Tyr Ala Ser Pro Ala
            180                 185                 190

Pro Ser Val Ser Ser Tyr Ser Ser Pro Ile Glu Pro Ser Ala Ser Ser
        195                 200                 205

Ala Met Phe Tyr Gln Arg Thr Ala Pro Ser Thr Ser Ala Ala Pro Leu
    210                 215                 220

Pro Thr Pro Ala Ala Pro Gln Gln Ile Ile Ser Pro Val Asn Pro Ala
225                 230                 235                 240

Trp Gln His His His Tyr Phe Pro Pro Ser Ser Thr Thr Pro Tyr Gln
                245                 250                 255

Gln Asn His Asp Arg Tyr Ile Cys Arg Thr Cys His Lys Ala Phe Ser
            260                 265                 270

Arg Pro Ser Ser Leu Arg Ile His Ser His Ser His Thr Gly Glu Lys
        275                 280                 285

Pro Phe Arg Cys Thr His Ala Gly Cys Gly Lys Ala Phe Ser Val Arg
    290                 295                 300

Ser Asn Met Lys Arg His Glu Arg Gly Cys His Ser Gly Arg Pro Val
305                 310                 315                 320

Ala Thr Ala Met Val
                325

<210> SEQ ID NO 81
<211> LENGTH: 325
```

```
<212> TYPE: PRT
<213> ORGANISM: Aspergillus kawachii

<400> SEQUENCE: 81

Met Asp Leu Ala Ser Leu Ile Ser His Pro Gly Pro Asp Pro Ile Met
1               5                   10                  15

Lys Ser Arg Ala Ser Tyr Ser Pro Met Thr Ser Tyr Lys Arg Ser
            20                  25                  30

Ile Glu Gln Thr Ser Asp Ser Tyr Phe Pro Ser Val Pro Ile Ser Tyr
                35                  40                  45

Thr Arg Ser Pro Gln Pro Pro Leu Ser Pro Pro Val Glu Asp His Ser
        50                  55                  60

Pro Lys Cys Ser Leu Pro Ser Ile Ser Thr Leu Leu Glu Gly Ala Asp
65                  70                  75                  80

Gly Ala Ala Met His Ala Ala Lys Arg Thr Arg Met Thr Pro Pro Leu
                85                  90                  95

Gln Arg Asp Leu Asp Ser Arg Gln Gln Ser Gln Ala Tyr Asp Leu Lys
            100                 105                 110

Ala Asn Gly Pro Gln Ile Ala Leu Pro Pro Thr Pro Pro Leu Arg Pro
        115                 120                 125

Gly Ser Ser Phe His Ser Ala Gly His Ser Pro Ala Ser Ser Ile Ser
130                 135                 140

Ala Ala Ser Asp Ala Ala Ala Pro Lys Arg Ser Asp Ser Tyr Pro Gln
145                 150                 155                 160

Val Pro Met Ala Leu Pro Ser Pro Ser Asp Arg Ser Ser Ile Ser Ser
                165                 170                 175

Gln Gly Ser Val Gln Gly Val Ser Ser Ala Ser Tyr Ala Ser Pro Ala
            180                 185                 190

Pro Ser Val Ser Ser Tyr Ser Ser Pro Ile Glu Pro Ser Ala Ser Ser
        195                 200                 205

Ala Met Phe Tyr Gln Arg Thr Ala Pro Ser Thr Ser Ala Ala Pro Leu
210                 215                 220

Pro Thr Pro Ala Ala Pro Gln Gln Ile Ile Ser Pro Val Asn Pro Ala
225                 230                 235                 240

Trp Gln His His His Tyr Phe Pro Pro Ser Ser Thr Thr Pro Tyr Gln
                245                 250                 255

Gln Asn His Asp Arg Tyr Ile Cys Arg Thr Cys His Lys Ala Phe Ser
            260                 265                 270

Arg Pro Ser Ser Leu Arg Ile His Ser His Ser His Thr Gly Glu Lys
        275                 280                 285

Pro Phe Arg Cys Thr His Ala Gly Cys Gly Lys Ala Phe Ser Val Arg
290                 295                 300

Ser Asn Met Lys Arg His Glu Arg Gly Cys His Ser Gly Arg Pro Val
305                 310                 315                 320

Ala Thr Ala Met Val
                325

<210> SEQ ID NO 82
<211> LENGTH: 334
<212> TYPE: PRT
<213> ORGANISM: Neosartorya fischeri

<400> SEQUENCE: 82

Met Asp Val Ala Ser Leu Ile Ser Pro Ser Glu Ser Asp Thr Val Pro
1               5                   10                  15
```

Thr Phe Arg Ser Arg Ser Ile Gln Asn Ser Ser Ala Ser His Tyr Lys
            20                  25                  30

Arg Leu Ser Glu Gln Tyr Thr Gly Ser Tyr Phe Ser Ala Ala Pro Thr
        35                  40                  45

His Thr Thr Ser Tyr Ser Arg Thr Pro Gln Pro Pro Leu Ser Pro Pro
 50                  55                  60

Ala Glu Asp Gln Pro Lys Cys Ser Leu Pro Ser Ile Ser Ile Leu Leu
65                  70                  75                  80

Glu Asn Ala Asp Gly Ala Ala His Ala Ala Lys Arg Gln Arg Thr
                85                  90                  95

Ser Leu Ser Thr His Arg Asp Ser Gly Pro Pro Tyr Asp Ser Ile Thr
            100                 105                 110

Pro His Ala Met Pro Pro Thr Pro Pro Leu Arg Pro Gly Ser Gly Phe
        115                 120                 125

His Ser Asn Gly His Ser Pro Ser Ala Ser Ser Val Ser Ala Thr Ser
130                 135                 140

Ser Ser Ala Val Met Lys Asn Thr Glu Thr Tyr Ser Gln Ala Pro Ile
145                 150                 155                 160

Gly Leu Pro Ser Pro Thr Asp Arg Ser Ser Ile Ser Ser Gln Gly Ser
            165                 170                 175

Val Gln His Ala Ala Gly Ala Pro Tyr Ala Ser Pro Ala Pro Ser Val
        180                 185                 190

Ser Ser Phe Ser Ser Pro Val Glu Pro Ser Thr Pro Ser Thr Ala Ala
    195                 200                 205

Tyr Tyr Gln Arg Asn Pro Ala Pro Asn Thr Phe Gln Asn Pro Gly Ser
210                 215                 220

Phe Pro Pro Thr Ser Ala Ala Ser Leu Pro Ser Pro Gly His Gln Gln
225                 230                 235                 240

Met Ile Ser Pro Val Thr Pro Ala Trp Gln His His Tyr Phe Pro
            245                 250                 255

Pro Ser Ser Ser Thr Pro Tyr Gln Gln Asn His Asp Arg Tyr Ile Cys
        260                 265                 270

Arg Thr Cys His Lys Ala Phe Ser Arg Pro Ser Ser Leu Arg Ile His
    275                 280                 285

Ser His Ser His Thr Gly Glu Lys Pro Phe Arg Cys Thr His Ala Gly
290                 295                 300

Cys Gly Lys Ala Phe Ser Val Arg Ser Asn Met Lys Arg His Glu Arg
305                 310                 315                 320

Gly Cys His Thr Gly Arg Pro Val Ala Thr Ala Met Val Gln
            325                 330

<210> SEQ ID NO 83
<211> LENGTH: 301
<212> TYPE: PRT
<213> ORGANISM: Penicillium chrysogenum

<400> SEQUENCE: 83

Met Asp Leu Ser Asn Leu Leu Ser His Ser Ala Ala Val Lys Pro Ile
1               5                   10                  15

Tyr Thr Pro Val Glu Ser Ser Tyr Tyr Lys Arg Ser Pro Pro Leu Ser
            20                  25                  30

Pro Pro Ala Glu Glu Pro Lys Val Ser Leu Pro Ser Ile Ser Ser Leu
        35                  40                  45

Phe Glu Gly Ala Asp Gly Ala Gln His Ala Ala Thr Ser Leu Thr Leu
 50                  55                  60

```
Asn Leu Pro Glu Arg Gln Arg Leu Ser Pro Ser Leu Gly Asp Arg His
 65                  70                  75                  80

Val Arg Val Gln Ser Tyr Glu Leu Pro Pro Thr Pro Pro Leu Arg Pro
                 85                  90                  95

Gly Ser Gly His Ala His Arg Arg Ala Ser Pro Val Glu Ser Leu Ser
            100                 105                 110

His Lys Glu Ala His Gln His His Leu His Arg Ser Ser Ile Ser Ser
        115                 120                 125

Asn Ser Ser Val His Ile Pro Arg Asn Thr Val Pro Tyr Ala Ser Pro
130                 135                 140

Val Pro Ser Val Ser Ser Tyr Thr Ser Pro Val Asp Ala Pro Gln Gln
145                 150                 155                 160

Pro Met Tyr Tyr Pro Arg Pro Pro Thr Thr Ser Ser Phe Gln Pro Ser
                165                 170                 175

Thr Pro Ala Ser Ala Pro Gln Met Pro Pro Val Gln Val Gln Thr Gln
            180                 185                 190

Gln Pro His Ser His Ser His Ser Ser Ala Leu Ile Ser Pro Val
        195                 200                 205

Thr Pro Ala Trp Gln His His His Tyr Phe Pro Pro Ser Thr Thr Ala
210                 215                 220

Pro Tyr Gln Gln Asn His Asp Arg Tyr Ile Cys Arg Thr Cys His Lys
225                 230                 235                 240

Ala Phe Ser Arg Pro Ser Ser Leu Arg Ile His Ser His Ser His Thr
                245                 250                 255

Gly Glu Lys Pro Phe Arg Cys Thr His Ala Gly Cys Gly Lys Ala Phe
            260                 265                 270

Ser Val Arg Ser Asn Met Lys Arg His Glu Arg Gly Cys His Ser Gly
        275                 280                 285

Arg Pro Ala Pro Ala Pro Ala Ala Thr Ala Leu Val Val
    290                 295                 300

<210> SEQ ID NO 84
<211> LENGTH: 336
<212> TYPE: PRT
<213> ORGANISM: Coccidioides immitis

<400> SEQUENCE: 84

Met Asn Val Ser Ser Leu Ile Thr Cys Asp Gln Pro His Gln Leu Arg
1               5                   10                  15

Ala Pro Ala Ser Ser Tyr Ser Glu His Arg Arg Ser Pro Ser Ile Pro
            20                  25                  30

Lys Pro Leu Gln Thr Glu Ser Ser Ser Cys Ala Ser Pro Tyr Ser Arg
        35                  40                  45

Phe Glu Arg Leu Pro Leu Ser Pro Glu Glu Asp Gly Lys Thr Gln
50                  55                  60

Phe Ser Leu Pro Ser Ile Ser Ser Leu Leu Arg Gly Val Asp Gly Val
65                  70                  75                  80

Ser Asp Ala His Val Ala Lys Arg Gln Arg Thr Asn Pro Pro Ser
                85                  90                  95

Ile Asp Leu Gly Met Glu Arg Arg Thr Ile Asp Gln Thr Leu Lys Gln
            100                 105                 110

Arg Pro Ala Leu Pro Leu Thr Pro Pro Leu Arg Pro Glu Ser Gly Met
        115                 120                 125

Asn Ser Thr Ser Gln Ser Pro Ser Thr Ser Ser Pro Pro Arg Ser Ala
```

```
            130                 135                 140
Ile Ser Leu Pro Ser Leu Val Arg Ser Tyr Pro Ser Pro Val Ser Glu
145                 150                 155                 160

Val Pro Glu Gly Arg Arg Met Ser Gln Ile Ser Arg His Ser Arg Gly
                165                 170                 175

Ala Ser Thr Ser Gln Thr Ser Gln Leu Ser Gly Pro Glu Thr Arg Tyr
            180                 185                 190

Pro Ser Pro Pro Asn Val Asn Ser Pro Thr Phe Ala Ala Pro Val Glu
                195                 200                 205

Pro Ala Pro Lys Pro Thr Glu Tyr Tyr Pro Ala Ser Arg Pro Val Thr
            210                 215                 220

Phe Pro Pro Val Ala Phe Ala Val Leu Pro Ser Gln Pro Thr His Pro
225                 230                 235                 240

Gln Val Leu Pro Leu Gly Ser Pro Ala Trp Gln His His Tyr Phe
                245                 250                 255

Pro Pro Ser Asn Thr Ala Thr Tyr Pro Leu Asn His Asp Arg Tyr Ile
                260                 265                 270

Cys Arg Ile Cys His Lys Ala Phe Ser Arg Pro Ser Ser Leu Arg Ile
            275                 280                 285

His Ser His Ser His Thr Gly Glu Lys Pro Phe Arg Cys Pro His Ala
            290                 295                 300

Gly Cys Gly Lys Ala Phe Ser Val Arg Ser Asn Met Lys Arg His Glu
305                 310                 315                 320

Arg Gly Cys His Pro Gly Arg Ser Ala Pro Ser Ala Leu Val Asn
                325                 330                 335

<210> SEQ ID NO 85
<211> LENGTH: 345
<212> TYPE: PRT
<213> ORGANISM: Ajellomyces capsulatus

<400> SEQUENCE: 85

Met Asn Leu Ser His Leu Val Thr Ser Tyr His Ser Pro Pro Ser Thr
1               5                   10                  15

Tyr Pro His Ser Gly Thr Ser Gln Lys Arg Gln Ser Leu Gln Ser Glu
            20                  25                  30

Ser Ser Leu Ser Val Ser Asn Gly Tyr Tyr Asp Arg Asn Ala Ser Asn
        35                  40                  45

Leu Ala Tyr Ala Arg Ser Pro Gln Pro Pro Leu Ser Pro Pro Val Glu
    50                  55                  60

Glu Gln Ser Arg Phe Ser Leu Pro Ser Ile Ser Ser Leu Leu Gln Gly
65                  70                  75                  80

Ala Asp Gln Leu Ser Pro Val His Ile Ala Lys Lys His Arg Pro Asn
                85                  90                  95

Pro Leu Ser Thr Gly Glu Val Asp Leu Lys Ser Gln Gly His Gly Ala
            100                 105                 110

Thr Gln Lys Pro Ile His Arg Pro Arg Met Ile Leu Pro Pro Thr Pro
        115                 120                 125

Pro Met Arg Pro Gly Ser Gly Leu Asp Gly Arg Asn His Ser Pro Ala
    130                 135                 140

Gly Ser Ser Pro Ser Ser Ala His Ser Pro Ile Ser Val Ala Asn Leu
145                 150                 155                 160

Thr Ser Ser Ser Ser Ala Asp Pro Ser Tyr Gln His Arg Met Pro Gln
                165                 170                 175
```

```
Gly Pro Leu Pro Pro Gln Ser Thr Arg Ser Ser Val Ser Gln Asn Ser
            180                 185                 190

Pro Val Ser Leu Pro Glu Lys His Tyr Ala Pro Ser Ser Asn Leu Pro
        195                 200                 205

Thr Ser Ser Thr Pro Phe Ala Ser Pro Val Glu Pro Leu Ala Asn Ser
    210                 215                 220

Thr Glu Tyr Tyr His Arg Pro Ser His Pro Pro Ser Phe Ser Thr Ser
225                 230                 235                 240

Ile Pro Leu Ala Ala Pro Pro Ala Gln Gln His His His Ser Met
                245                 250                 255

Ile Ser Thr Trp Gln His His His Tyr Phe Pro Pro Ser Asn Thr Ala
            260                 265                 270

Pro Tyr Pro Gln Asn His Asp Arg Tyr Ile Cys Arg Ile Cys His Lys
        275                 280                 285

Ala Phe Ser Arg Pro Ser Ser Leu Arg Ile His Ser His Ser His Thr
    290                 295                 300

Gly Glu Lys Pro Phe Lys Cys Pro His Val Asn Cys Gly Lys Ser Phe
305                 310                 315                 320

Ser Val Arg Ser Asn Met Lys Arg His Glu Arg Gly Cys His Thr Gly
                325                 330                 335

Arg Pro Thr Gln Ala Ala Leu Val Asn
            340                 345

<210> SEQ ID NO 86
<211> LENGTH: 423
<212> TYPE: PRT
<213> ORGANISM: Uncinocarpus reesii

<400> SEQUENCE: 86

Met Asn Val Ser Ser Leu Ile Ser Cys Asp Gln Thr Ala Pro Phe His
1               5                   10                  15

Gly Ser Ala Thr Ser Tyr Phe Glu His His Gln Arg Ile Arg Ser Pro
            20                  25                  30

Ser Ile Pro Lys Arg Ser His Glu Glu Asn Ser Ser Ser Ala Ser Pro
        35                  40                  45

Tyr Pro Pro Phe Ala Thr Leu Pro Leu Ser Pro Pro Glu Asp Asp Gly
    50                  55                  60

Lys Thr Thr Phe Ser Leu Pro Ser Ile Ser Ser Leu Leu Gln Ser Val
65                  70                  75                  80

Asp Ala Ala Ser Asp Thr His Val Ala Lys Arg Gln Arg Ala Asn Pro
                85                  90                  95

Pro Pro Ser Ile Asp Leu Ala Leu Glu Arg Arg Gly Ala Cys Ala Asp
            100                 105                 110

Gln Ala Ile Arg Gln Arg Pro Ala Leu Pro Leu Thr Pro Pro Leu Arg
        115                 120                 125

Pro Glu Ser Gly Met Gly Gly Val Asn His Ser Pro Ser Ala Ser Ser
    130                 135                 140

Pro Pro Arg Thr Ala Ile Ser Leu Pro Ser Leu Ile Gly Ser Tyr Pro
145                 150                 155                 160

Ser Pro Val Ser Glu Ala Pro Glu Gly Arg Arg Met Ser Gln Ile Ser
                165                 170                 175

Arg His Ser Ser Arg Thr Ser Ile Ser Gln Ser Ser Gln His Pro Gly
            180                 185                 190

Pro Glu Ala Arg Tyr Pro Ser Pro Pro Thr Leu Ser Ser Pro Ser Phe
        195                 200                 205
```

Ala Ala Pro Ile Glu Pro Pro Lys Pro Glu Tyr Tyr Ser Ser Gly
    210             215                 220

Ala Arg Pro Thr Asn Phe Pro Pro Val Thr Phe Ala Val Leu Pro Ser
225             230             235                 240

Gln Pro Thr His Pro Gln Met Val Ala Leu Gly Ser Pro Ala Trp Gln
            245                 250                 255

His His His Tyr Phe Pro Pro Ser Asn Thr Ala Thr Tyr Pro Leu Asn
            260                 265                 270

His Asp Arg Tyr Ile Cys Arg Ile Cys His Lys Ala Phe Ser Arg Pro
        275                 280                 285

Ser Ser Leu Arg Ile His Ser His Ser His Thr Gly Glu Lys Pro Phe
    290                 295                 300

Arg Cys Pro His Ala Gly Cys Gly Lys Ala Phe Ser Val Arg Asn Gln
305                 310                 315                 320

Pro Arg Ser Gln Arg Ser Leu Ile Glu Lys Arg Lys Gly Tyr Ala Ile
                325                 330                 335

Gly Phe Asp Glu Trp Val Leu Thr Met Ile Thr Pro Thr Ile Arg Ser
            340                 345                 350

Thr Asn Glu Gln Ile Tyr Thr Thr Ala Ser Cys Lys Ile Ala Asn Val
        355                 360                 365

Ala Val Ile Asn Ile Asn Arg Arg Ile Ala Glu Leu Arg Lys Ser Phe
    370                 375                 380

Arg Asn Arg Arg Ser Asn Gly Thr Leu Ser Pro Thr Lys Arg Arg Val
385                 390                 395                 400

Lys Leu Ala Phe Ser Leu Asp Cys Gln Ser Thr Ser Ser Ser Arg Leu
                405                 410                 415

Ala Leu Leu Pro Gln Ser Leu
            420

<210> SEQ ID NO 87
<211> LENGTH: 247
<212> TYPE: PRT
<213> ORGANISM: Penicillium marneffei

<400> SEQUENCE: 87

Met Asp Asn Val Pro Ala Ser Lys Arg Ala Arg His Asp Ser Gly Asp
1               5                   10                  15

Tyr Ser Arg Gly Phe Leu Pro Pro Thr Pro Pro Met Arg Pro Cys Ser
            20                  25                  30

Gly Phe Thr Glu Gly Ser Ser Pro Ala Ser Leu Pro Ser Gly Arg Ser
        35                  40                  45

His Ser Ala Ser Ile Ser Ser Ala Val Ser His Pro Ser His Gln Gln
    50                  55                  60

Arg Thr Ser Leu Pro Ser Ile Ser Ala Ser Leu Gln Asn Thr Pro Ile
65                  70                  75                  80

His Pro Ser Glu Arg Leu Ser Ile Ser Ser Leu Ala Ser His Asp Ser
                85                  90                  95

Ser Arg Leu Ser His Ala Ile Pro Ser Pro Ser Ser Thr Thr Ala Ser
            100                 105                 110

Ile Thr Thr Thr Ala Thr Pro Ser Ser Tyr Tyr Ser Thr Ser Glu
        115                 120                 125

Glu Lys Ala Tyr Pro Arg Ser His Ser Thr Ser Ala Pro Val Thr Pro
    130                 135                 140

Ser Thr Leu Val Pro Pro Pro Pro Ala Met Leu Ser Pro Val Asn His

```
                145                 150                 155                 160
Pro Gly Trp Gln His His His Tyr Phe Pro Leu Ser Thr Thr Thr Ser
                    165                 170                 175

Tyr Pro Gln Asn His Glu Arg Tyr Val Cys Arg Thr Cys His Lys Ala
                    180                 185                 190

Phe Ser Arg Pro Ser Ser Leu Arg Ile His Ser His Ser His Thr Gly
                    195                 200                 205

Glu Lys Pro Phe Arg Cys Thr His Ala Gly Cys Gly Lys Ala Phe Ser
                    210                 215                 220

Val Arg Ser Asn Met Lys Arg His Glu Arg Gly Cys His Ser Gly Arg
225                 230                 235                 240

Pro Met Thr Ala Thr Val Val
                    245

<210> SEQ ID NO 88
<211> LENGTH: 317
<212> TYPE: PRT
<213> ORGANISM: Botryotinia fuckeliana

<400> SEQUENCE: 88

Met Ala Ser Ser Leu Val Ser Asn Pro Tyr Thr Val His Pro Met Ala
1               5                   10                  15

Gln His Ser Ser Tyr Thr Tyr Val Asn Ala Pro Gln Pro Pro Pro Ser
                    20                  25                  30

Pro Pro Val Asp Glu Thr Ser Lys Cys Ser Leu Pro Ser Ile Ser Ser
                    35                  40                  45

Leu Leu Gly Leu Ala Asp Gly Ser Ser Pro Thr Glu Gln Ala Gln Gln
                    50                  55                  60

Gln Ser Ser Pro Gln Gln Ala Ala Phe Lys Glu Asp Tyr Arg Pro Glu
65                  70                  75                  80

Ser Gly His Gln Tyr Gly Pro Ser Ser Met Ser Ser Arg Gly Ala
                    85                  90                  95

Leu Pro Pro Thr Pro Pro Met Gln Ser Asp Gly Gly Phe Asp Gly Arg
                    100                 105                 110

Gln Ser Pro Ser Gln Ala Ser Thr Ser Ser Tyr Ser Val Val Ser Ala
                    115                 120                 125

Pro Asn Tyr Tyr Phe Asn Pro Ser Gln Val Ser Ala Ile Asn Asn Met
                    130                 135                 140

Glu Pro His Ala Gln Arg Gln Pro Val Gln Thr Val Thr Arg Arg Val
145                 150                 155                 160

Ser Met Pro Val Ser Ser Met Gln Tyr Gly His Ser Pro Phe Asn Gly
                    165                 170                 175

Ser Tyr Thr Met Ser Pro Gly Ala Gln Ser Leu Ser Ser Tyr Tyr Pro
                    180                 185                 190

Ser Pro Ile Gln Thr Gln Ser Pro Gln Val Ser Ser Leu Tyr Tyr Gln
                    195                 200                 205

Arg Pro Leu Pro Gln Gln Phe Pro Pro Met Met Pro Val Ser Val
                    210                 215                 220

Thr Leu Thr Pro Ser Ser Gly Ala Asn Pro Trp Gln His His His Tyr
225                 230                 235                 240

Ile Ser Pro Ser Ser Ala Ala Ser Phe Pro Gln Ser Gln Asp Arg Tyr
                    245                 250                 255

Ile Cys Gln Thr Cys Asn Lys Ala Phe Ser Arg Pro Ser Ser Leu Arg
                    260                 265                 270
```

```
Ile His Ser His Ser His Thr Gly Glu Lys Pro Phe Lys Cys Pro His
            275                 280                 285

Gln Asn Cys Gly Lys Ala Phe Ser Val Arg Ser Asn Met Lys Arg His
    290                 295                 300

Glu Arg Gly Cys His Ser Phe Glu Ser Ala Ser Met Val
305                 310                 315

<210> SEQ ID NO 89
<211> LENGTH: 305
<212> TYPE: PRT
<213> ORGANISM: Neurospora tetrasperma

<400> SEQUENCE: 89

Met Ala Pro Thr Thr Leu Thr Pro Gln Tyr Pro Ala Gln Pro Tyr Gly
1               5                   10                  15

Phe Ala Pro Pro Ser Pro Pro Leu Asp Asp Ser Asn Lys Cys Ser
            20                  25                  30

Leu Pro Ser Ile Ser Asn Leu Leu Val Met Ala Asp Gln Gly Ser Pro
            35                  40                  45

Thr Ser Glu Thr Ser Pro Gln Ser Gln Gln Leu His Phe Ser Lys Pro
    50                  55                  60

Asp Asn Arg Pro Asn Ser Ser Gln Phe Gly Asn Pro Ala Ser Ile Arg
65                  70                  75                  80

Ala Asn Leu Pro Pro Ser Pro Pro Met Ser Ser Glu Ala Ser Phe Glu
            85                  90                  95

Gly Tyr Arg Ser Pro Ser Ser Lys Pro Ala Ser Gln Ser Gln Gly Ser
            100                 105                 110

Ser Asn Tyr Tyr Tyr Glu Thr Thr Pro Pro Leu Ser Gln His Glu Ala
            115                 120                 125

Asp Ser Arg Gln Met Ala Thr Ala Ala Pro Arg Ala Pro Val Gln Ser
    130                 135                 140

Ser Thr Phe Gln Thr Gln Tyr Pro Ser Ser Ala Gly Tyr Ser Ser Gln
145                 150                 155                 160

Ser Gly Met Asn Pro Tyr Tyr Pro Pro Met Gln Pro Thr Pro Pro Pro
            165                 170                 175

Gln Gln Gln Met Ser Gly Leu Tyr Tyr Gln Arg Pro Leu Pro Gln Thr
            180                 185                 190

Phe Thr Pro Ala Val Pro Val Pro Val Thr Leu Ala Pro Val Thr Gly
    195                 200                 205

Ala Asn Pro Trp Gln His His His Tyr Ile Ala Pro Ser Ser Thr Ala
    210                 215                 220

Ser Phe Pro Gln Ser Gln Asp Arg Tyr Ile Cys Gln Thr Cys Asn Lys
225                 230                 235                 240

Ala Phe Ser Arg Pro Ser Ser Leu Arg Ile His Ser His Ser His Thr
            245                 250                 255

Gly Glu Lys Pro Phe Lys Cys Pro His Ala Gly Cys Gly Lys Ala Phe
            260                 265                 270

Ser Val Arg Ser Asn Met Lys Arg His Glu Arg Gly Cys His Ser Phe
    275                 280                 285

Glu Ser Ser Asn Gly Arg Ser Ser Gly Asn Ser Asn Asn Gly Ala Ser
    290                 295                 300

Ala
305

<210> SEQ ID NO 90
```

<211> LENGTH: 305
<212> TYPE: PRT
<213> ORGANISM: Neurospora crassa

<400> SEQUENCE: 90

```
Met Ala Pro Thr Thr Leu Thr Pro Gln Tyr Pro Ala Gln Pro Tyr Gly
1               5                   10                  15

Phe Ala Pro Pro Pro Ser Pro Pro Leu Asp Asp Ser Asn Lys Cys Ser
            20                  25                  30

Leu Pro Ser Ile Ser Asn Leu Leu Val Met Ala Asp Gln Gly Ser Pro
        35                  40                  45

Thr Ser Glu Thr Ser Pro Gln Ser Gln Gln Leu His Phe Ser Lys Pro
    50                  55                  60

Asp Asn Arg Pro Asn Ser Ser Gln Phe Gly Asn Pro Ala Ser Ile Arg
65                  70                  75                  80

Ala Asn Leu Pro Pro Ser Pro Pro Met Ser Ser Glu Ala Ser Phe Glu
                85                  90                  95

Gly Tyr Arg Ser Pro Ser Ser Lys Pro Ala Ser Gln Ser Gln Gly Ser
            100                 105                 110

Ser Asn Tyr Tyr Tyr Glu Thr Thr Pro Pro Leu Ser Gln His Glu Ala
        115                 120                 125

Asp Ser Arg Gln Met Ala Thr Ala Thr Pro Arg Ala Pro Val Gln Ser
    130                 135                 140

Ser Thr Phe Gln Thr Gln Tyr Pro Ser Ser Ala Gly Tyr Ser Ser Gln
145                 150                 155                 160

Ser Gly Met Asn Pro Tyr Tyr Pro Pro Met Gln Pro Thr Pro Pro Pro
                165                 170                 175

Gln Gln Gln Met Ser Gly Leu Tyr Tyr Gln Arg Pro Leu Pro Gln Thr
            180                 185                 190

Phe Thr Pro Ala Val Pro Val Pro Val Thr Leu Ala Pro Val Thr Gly
        195                 200                 205

Ala Asn Pro Trp Gln His His His Tyr Ile Ala Pro Ser Ser Thr Ala
    210                 215                 220

Ser Phe Pro Gln Ser Gln Asp Arg Tyr Ile Cys Gln Thr Cys Asn Lys
225                 230                 235                 240

Ala Phe Ser Arg Pro Ser Ser Leu Arg Ile His Ser His Ser His Thr
                245                 250                 255

Gly Glu Lys Pro Phe Lys Cys Pro His Ala Gly Cys Gly Lys Ala Phe
            260                 265                 270

Ser Val Arg Ser Asn Met Lys Arg His Glu Arg Gly Cys His Ser Phe
        275                 280                 285

Glu Ser Ser Asn Gly Arg Ser Ser Gly Asn Ser Asn Asn Ser Ala Ser
    290                 295                 300

Ala
305
```

<210> SEQ ID NO 91
<211> LENGTH: 309
<212> TYPE: PRT
<213> ORGANISM: Magnaporthe oryzae

<400> SEQUENCE: 91

```
Met Ala Ala Thr Met Ile Gln Gln Pro Tyr Pro Ile His Gln Gln Gln
1               5                   10                  15

Ser Gln Tyr Ser Tyr Met Val Gln Pro Gln Gly Pro Pro Ser Pro Pro
            20                  25                  30
```

```
Met Asp Asp Asn Lys Cys Ser Leu Pro Ser Ile Ser Asn Leu Leu Gly
            35                  40                  45

Leu Ala Asp Gln Gly Ser Pro Thr Ser Glu Thr Ser Ala Gln Phe Arg
 50                  55                  60

Glu Glu Gln Lys Gln Gln Gln Ala Ala Gln Gln Ser Arg Pro Asn Ser
 65                  70                  75                  80

Ser His Tyr Ser Asn Ala Val Gln Ser Val Arg Gln Gly Ile Pro Pro
                85                  90                  95

Thr Pro Pro Met Thr Ser Glu Thr Ser Phe Asp Gly Tyr Asn Ser Pro
                100                 105                 110

Ser Asn Lys Ser Val Ser Gln Leu Pro Ala Thr Gly Tyr Tyr Phe Glu
            115                 120                 125

Ala Thr Pro Pro Gly His Met Glu Met Glu Pro Arg Pro His Met
130                 135                 140

Thr Ser Val Ser Arg Val Pro Val Gln Ala Pro Phe Ala Gln Ser Ala
145                 150                 155                 160

Tyr Ser Ala Pro Tyr Gly Met Ala Pro Ser Asn Pro Met Ala Ala Tyr
                165                 170                 175

Tyr Pro Thr Met Gln Pro Thr Pro Pro Gln Gln Pro Gln Ile Ser
                180                 185                 190

Ser Leu Tyr Tyr Gln Arg Pro Leu Pro Gln Ala Phe Pro Met Pro
            195                 200                 205

Val Asn Val Ser Met Gly Pro Gln Ser Gly Ala Asn Pro Trp Gln His
            210                 215                 220

His His Tyr Ile Ser Pro Ser Ala Ala Ala Ser Phe Pro Gln Ser Gln
225                 230                 235                 240

Asp Arg Tyr Ile Cys Gln Thr Cys Asn Lys Ala Phe Ser Arg Pro Ser
                245                 250                 255

Ser Leu Arg Ile His Ser His Ser His Thr Gly Glu Lys Pro Phe Lys
            260                 265                 270

Cys Pro His Ala Gly Cys Gly Lys Ala Phe Ser Val Arg Ser Asn Met
            275                 280                 285

Lys Arg His Glu Arg Gly Cys His Asn Tyr Asp Ser Ser Ser Ser Asn
            290                 295                 300

Gly Thr Ala Met His
305

<210> SEQ ID NO 92
<211> LENGTH: 342
<212> TYPE: PRT
<213> ORGANISM: Chaetomium globosum

<400> SEQUENCE: 92

Met Ala Asn Thr Met Val Thr His Tyr Ala His Val Pro Gln His Ser
1               5                   10                  15

Leu Gln Tyr Gly Tyr Met Pro Pro Ser Pro Met Asp Glu Ala
            20                  25                  30

Ala Lys Cys Ser Leu Pro Ser Ile Ser Asn Leu Leu Gly Leu Ala Asp
            35                  40                  45

Gln Gly Ser Pro Thr Ser Glu Thr Ser Pro Gln Ser Gln Gln Gln Gln
 50                  55                  60

Gln Ala Gln Gln Gln Gln Gln Gln Cys Met Ser Ser Ser Trp Trp
 65                  70                  75                  80

Asp Met Gly His Leu Asp Thr Asp Ser Thr Pro Ala Gln Gly Ser Lys
```

Pro Glu Thr Arg Pro Asn Ser Ser His Tyr Thr Asn Pro Val Thr Ile
                85                  90                  95
                            100                 105                 110

Arg Thr Gly Leu Pro Pro Ser Pro Met Ser Ser Asp Ala Ser Phe
            115                 120                 125

Glu Gly Phe Asn Ser Pro Ser Thr Arg Ser Val Ser Gln Val Pro Asn
            130                 135                 140

Gly Ser Asn Tyr Phe Phe Glu Thr Thr Pro Pro Leu Gln Met Glu Ala
145                 150                 155                 160

Asp Ala Arg Gln Met Thr Ala Ala Ala Val Pro Arg Val Ser Val
                165                 170                 175

Gln Ala Ser Ala Tyr Gln Pro Gln Tyr Ala Pro Gly Pro Ala Tyr Met
            180                 185                 190

Ser Gln Pro Ala Met Thr Ser Tyr Tyr Pro Pro Met Gln Ser Ala Ala
            195                 200                 205

Pro Pro Gln Thr Gln Met Ser Gly Leu Tyr Tyr Gln Arg Pro Leu Pro
            210                 215                 220

Gln Ser Phe Pro Pro Met Ser Met Ser Met Thr Leu Ala Pro Thr
225                 230                 235                 240

Ala Gly Asn Pro Trp Gln His His His Tyr Ile Ala Pro Ser Ala Ser
                245                 250                 255

Ala Ser Phe Pro Gln Ser Gln Asp Arg Tyr Ile Cys Pro Thr Cys Ser
            260                 265                 270

Lys Ala Phe Ser Arg Pro Ser Ser Leu Arg Ile His Ser His Ser His
            275                 280                 285

Thr Gly Glu Lys Pro Phe Lys Cys Pro Phe Pro Gly Cys Gly Lys Ala
            290                 295                 300

Phe Ser Val Arg Ser Asn Met Lys Arg His Glu Arg Gly Cys His Asn
305                 310                 315                 320

Tyr Asp Ser Ser Ser Thr Thr Ser Ser Thr Gly Thr Met Asn Ser Asn
                325                 330                 335

Thr Gly Gly Ser Arg Pro
            340

<210> SEQ ID NO 93
<211> LENGTH: 276
<212> TYPE: PRT
<213> ORGANISM: Fusarium oxysporum

<400> SEQUENCE: 93

Met Glu Glu Gln Lys Cys Ser Leu Pro Ser Ile Ser Asn Leu Leu Gly
1               5                   10                  15

Leu Ala Asp Ala Gly Ser Pro Thr Ser Glu Ser Ser Pro Thr Ser Arg
            20                  25                  30

Gln His Ser Pro Arg Phe Glu Val Pro Pro Ser His Gly His Ser
            35                  40                  45

Arg Ala Gly Ser Glu Trp Ala Lys Ser Ser His Arg Gly Leu Pro Pro
        50                  55                  60

Thr Pro Pro Met Ser Thr Asp Ala Ser Phe Glu Gly Tyr Ser Ser Pro
65                  70                  75                  80

Thr Arg Lys Pro Ser Asn Gln Ala Tyr Pro Gly Ser Ala Pro Arg Thr
                85                  90                  95

Tyr Tyr Tyr Glu Thr Thr Pro Pro Leu Glu Ala Asp Ala Gln Arg Gln
            100                 105                 110

-continued

```
Ala Ser Val Thr Ala Ile Pro Arg Ala Thr Pro Pro Ala Thr Ala Pro
        115                 120             125
Tyr Pro Gln Gln Ala His Pro Thr Val Tyr Ala Asn Pro Ala Pro Val
    130             135             140
Gly Ala Tyr Tyr Pro Ala Ala Gln Val Pro Pro Ala Val Gln Pro Gln
145             150             155                         160
Glu Met Asn Pro Tyr Tyr Gln Arg Pro Leu Pro Gln Ala Tyr Pro Pro
            165             170             175
Pro Val Ser Met Pro Ala Pro Ala Pro Ser Gly Ala Asn Pro Trp Gln
            180             185             190
His His His Tyr Leu Asn Pro Thr Gly Ala Ala Ala Phe Pro Gln Ser
        195             200             205
Gln Asp Arg Tyr Ile Cys Pro Thr Cys Asn Lys Ala Phe Ser Arg Pro
    210             215             220
Ser Ser Leu Arg Ile His Ser His Ser His Thr Gly Glu Lys Pro Phe
225             230             235                         240
Lys Cys Pro His Ala Gly Cys Gly Lys Ala Phe Ser Val Arg Ser Asn
            245             250             255
Met Lys Arg His Glu Arg Gly Cys His Ser Phe Glu Phe Asn Gly Ser
            260             265             270
Val Ile Arg Gly
        275
```

EFFECTS OF ALTERATION OF EXPRESSION OF THE MTFA GENE AND ITS HOMOLOGS ON THE PRODUCTION OF FUNGAL SECONDARY METABOLITES

CROSS REFERENCE TO RELATED APPLICATIONS

This application is a Continuation-in-Part of co-pending U.S. Utility application Ser. No. 14/070,094, filed Nov. 1, 2013, and claims priority under 35 U.S.C. §119(e) to U.S. Provisional Patent Application No. 61/721,777 filed Nov. 2, 2012. The disclosures set forth in the referenced applications are incorporated herein by reference in their entireties, including all information as originally submitted to the United States Patent and Trademark Office.

This invention was made with government support under Contract No. NIH R15A1081232 awarded by the National Institutes of Health. The U.S. Government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 25, 2013, is named 702040_SEQ_ST25.txt and is 130,139 bytes in size.

BACKGROUND

Many fungal secondary metabolites such as antibiotics, are of industrial interest. Numerous fungal secondary metabolites have beneficial biological activities that can be used in the medical field, including antibiotics and antitumor drugs. Other fungal products, such as mycotoxin, are detrimental for human and animal health and negatively impact agriculture causing economic losses. Overexpression of the gene mtfA enhances production of fungal compounds with applications in the medical field, and overexpression or impaired mtfA expression decreases the production of compounds such as mycotoxins that negatively affect health/agriculture/economy.

Species of the genus *Aspergillus* produce numerous secondary metabolites, including compounds with beneficial effects, such as antibiotics and other molecules with application in the medical field. *Aspergillus nidulans*, a model filamentous fungus studied for more than fifty years, produces the mycotoxin sterigmatocystin (ST). ST and the carcinogenic compounds called aflatoxins (AF), produced by related species such as *A. flavus, A. parasiticus*, and *A. nomiusi* are both synthesized through a conserved metabolic pathway where ST is the penultimate precursor. The genes responsible for ST/AF biosynthesis are clustered. Within the clusters, the regulatory gene aflR encodes a transcription factor that acts as a specific cluster activator.

*Aspergillus nidulans* also produces the beta-lactam antibiotic penicillin and the antitumoral compound terraquinone.

In fungi secondary metabolism, regulation is often found to be governed by genetic mechanisms also controlling asexual and sexual development. One of the main common regulatory links is the global regulatory gene veA, described to be a developmental regulator in *A. nidulans*. The connection between veA and the synthesis of numerous secondary metabolites, including ST was described. Absence of the veA gene in *A. nidulans* prevents OR expression and ST biosynthesis. VeA also regulates the production of other metabolites, including penicillin. In other fungi, veA homologs also regulate the synthesis of penicillin in *Penicillium chrysogenum* as well as cephalosporin C in *Acremonium chrysogenum*. Furthermore, veA also regulates the biosynthesis of other mycotoxins, for example AF, cyclopiazonic acid and aflatrem in *Aspergillus flavus*, trichothecenes in *F. graminerum*, and fumonisins and fusarins in *Fusarium* spp, including *F. verticillioides* and *F. fujikuroi*.

veA is extensively conserved in Ascomycetes. Most of the studies on the veA regulatory mechanism of action have been carried out using the model fungus *A. nidulans*. It is known that KapA α-importin transports the VeA protein to the nucleus, particularly in the dark, a condition that favors ST production. In the nucleus, VeA interacts with several proteins such as the light-responsive protein FphA, which interacts with the LreA-LreB. FphA, LreA and LreB also have influence fungal development and mycotoxin production. While FphA negatively regulates sexual development and the synthesis of ST, the LreA and LreB proteins play the opposite role. In the nucleus VeA also interacts with VelB and LaeA. LaeA, a chromatin-modifying protein is also required for the synthesis of ST and other secondary metabolites. Deletion of velB decreased and delayed ST production, indicating a positive role in ST biosynthesis.

In addition to its role as global regulator of development and secondary metabolism, VeA is also required for normal plant pathogenicity by several mycotoxigenic species, such as *A. flavus, F. verticillioides F. fujikuroi*, and *F. graminearum*. Deletion of veA homologs in these organisms results in a decrease in virulence with a reduction in mycotoxin biosynthesis.

SUMMARY

Manipulation of a gene encoding MtfA (Master Transcription Factor) is disclosed.

A gene replacement construct designated ΔmtfA and a ΔmtfA mutant are disclosed.

A method is disclosed to regulate expression of fungal secondary metabolites such as mycotoxin or sterigmatocystin, and synthesis of penicillin by fungal genes including
 (a) obtaining a fungal transcription factor gene, mtfA and a regulatory gene; and
 (b) overexpressing or eliminating the mtfA gene (or parts of the gene) or interrupting the gene with an insertion or deletion.

A method to increase production of penicillin from a fungus includes
 (a) obtaining a fungus capable of producing penicillin; and
 (b) causing the fungus to overexpress the mtfA gene.

A method to reduce sexual and asexual development of a fungus, includes
 (a) obtaining the fungus; and
 (b) deleting mtfA (or parts of the gene) or interrupting the gene with an insertion, in the fungus.

Orthologs of mtfA are also described.

BRIEF DESCRIPTION OF THE DRAWINGS

FIG. 11 Alignment of MtfA-like proteins in filamentous fungi. *Aspergillus nidulans* (*A.nidulans*) (SEQ ID NO: 74), *Aspergillus oryzae* (*A. oryzae*) (SEQ ID NO: 79), *Aspergillus niger* (*A.niger*) (SEQ ID NO: 80), *Aspergillus kawachii* (*A.kawachii*) (SEQ ID NO: 81), *Neosartorya fischeri* (*N.fischeri*) (SEQ ID NO: 82), *Penicillium chrysogenum* (*P.chrysogenum*) (SEQ ID NO: 83), *Coccidioides immitis* (*C. immitis*) (SEQ ID NO: 84), *Ajellomyces capsulatus* (*A.capsulatus*) (SEQ ID NO: 85), *Uncinocarpus reesii* (*U.reesii*) (SEQ ID NO: 86), *Penicillium marneffei* (*P.marneffei*) (SEQ ID NO: 87), *Botryotinia fuckeliana* (*B.fuckeliana*) (SEQ ID NO: 88), *Neurospora tetrasperma* (*N.tetrasperma*) (SEQ ID NO: 89), *Neurospora. crassa* (*N.crassa*) (SEQ ID NO: 90), *Magnaporthe oryzae* (*M.oryzae*) (SEQ ID NO: 91), *Chaetomium globosum* (*C.globosum*) (SEQ ID NO: 92) and *Fusarium oxysporum* (*F.oxysporum*) (SEQ ID NO: 93). Accession ID's and source of these sequences are as mentioned in. MAFFT version 6.0 (http://mafft.cbrc.jp/alignment/server/index.html) and BoxShade version 3.2.1 (http://www.ch.embnet.org/software/BOX_form.html) were utilized for alignment and presentation.

FIG. 24 Amino acid comparison of the predicted gene products of mtfA homologs. SEQ ID NOS 2-17, respectively, in order of appearance. The analysis indicates high conservation of this gene and gene product in different fungal species. Shaded part indicates the domains with highest conservation.

DETAILED DESCRIPTION OF THE DISCLOSURE

Figure 1:
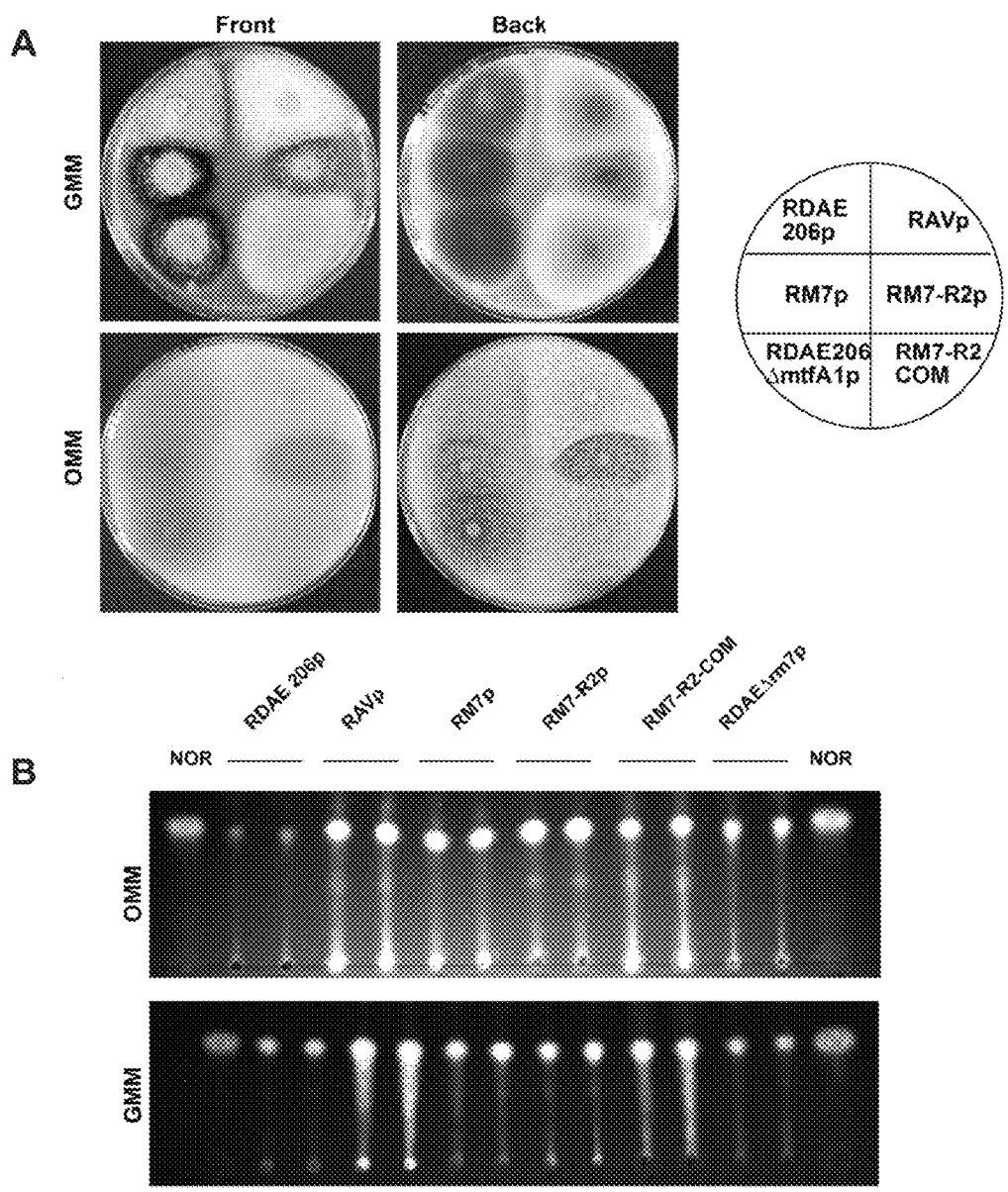
FIG. 1. Revertant mutant 7 (RM7) produces NOR. Mycelia growth and production of NOR compound. (A) Approximately 500 conidia of RM7 and RDAE206 were inoculated on top of OMM and incubated for six days at 37° C. under dark conditions. Pinkish or orange color was observed at the bottom of the plates. TLC analysis of NOR production was done. Fungal strains were top-agar inoculated at $10^6$ conidia/ml on top of OMM and GMM and incubated at light and dark conditions for six days. (B) Mycelial cores were taken, toxin were extracted and analyzed as described in methods and materials.

The fungal transcription factor encoding gene, mtfA (master transcription factor A), and is gene product, MtfA protein, are located in nuclei of fungal cells. For the first time overexpression of mtfA gene is shown to increase penicillin production and decrease mycotoxin production in the model fungus *Aspergillus nidulans*. Variations in the expression of mtfA also affect the synthesis of other secondary metabolites. Deletion of mtfA in the model fungus *Aspergillus nidulans* also decreases or eliminates sterigmatocystin production.

Manipulations to alter the expression of the fungal mtfA gene increases the production of both beneficial fungal secondary metabolites, such as penicillin G, and decrease the production of those secondary metabolites that are detrimental, such as aflatoxin-related mycotoxins.

An application of these manipulations is to increase the production of valuable fungal secondary metabolites and decrease the production of detrimental fungal secondary metabolites in fungal cells.

Secondary metabolism in the model fungus *Aspergillus nidulans* is controlled by the conserved global regulator VeA, which also governs morphological differentiation. Among the secondary metabolites regulated by VeA is the mycotoxin sterigmatocystin (ST). The presence of VeA is necessary for the biosynthesis of this carcinogenic compound. A revertant mutant was identified that synthesizes ST intermediates in the absence of VeA. The point mutation occurred at the coding region of a gene encoding a novel putative $C_2H_2$ zinc finger domain transcription factor that is designated mtfA. The *A. nidulans* mtfA gene product, MtfA, localizes at nuclei independently of the illumination regime. Deletion of the mtfA gene restored mycotoxin biosynthesis in the absence of veA, but drastically reduced mycotoxin production when mtfA gene expression was altered, by deletion or overexpression, in *A. nidulans* strains with a veA wild-type allele. mtfA regulates ST production by affecting the expression of the specific ST gene cluster activator aflR. Of interest, mtfA is also a regulator of other secondary metabolism gene clusters, such as genes responsible for the synthesis of terrequinone and penicillin. As in the case of ST, deletion or overexpression of mtfA was also detrimental for the expression of terrequinone genes. Deletion of mtfA also decreased the expression of the genes in the penicillin gene cluster, reducing penicillin production. However, over-expression of mtfA enhanced the transcription of penicillin genes, increasing penicillin production more than 5 fold with respect to the control. In addition to its effect on secondary metabolism, mtfA also affects asexual and sexual development in *A. nidulans*. Deletion of mtfA results in a reduction of conidiation and sexual stage. mtfA putative orthologs were found conserved in other fungal species.

In summary, deletion of mtfA in a deletion veA genetic background increases ST toxin production; deletion or overexpression of mtfA in a wild type (veA+) genetic background results in a reduction of ST. Because mtfA is not found in plants or animals, mtfA could be used as a genetic target to prevent or reduce toxin production and possibly the production of other secondary metabolites; deletion or over-expression of mtfA in a wild type (veA+) genetic background results in a decrease in the expression of terraquinone genes; deletion of mtfA in a wild type (veA+) genetic background results in a decrease in penicillin production; and deletion of mtfA leads to a reduction of sexual and asexual development in fungus.

Overexpression of mtfA in a wild type (veA+) genetic background results in an increase (25% increase to 5 fold) in penicillin production. Other fungi, including the commercially used antibiotic producer *Penicillium chrysogenum*, contain a mtfA ortholog.

The RM7 gene and MtfA gene are the same gene. RM7's initial name was renamed mtfA based on the *Aspergillus nidulans* nomenclature, but they have the same sequence. The accession number and the coding region of the *Aspergillus nidulans* mtfA gene in the disclosure is: accession number ANID_08741 sequence:
(SEQ ID NO: 1)
ATGGATCTCGCCAACCTCATCTCCCAACCGGGGCCTGAGCCTGCTCTGAC

GGCCAAATCAAGATACAGCCCTCCTGCCTTTGAACCGGGCTCCTTCTACG

CCGCATCTACTTCATTCACGCGGACACAAGCGCCACTATCGCCTCCAGTC

GAGGATAGATCTTCTCGCTGCTCACTGCCATCAATCTCTGCGCTTCTTGA

CAGCGCAGACGGCGCCTCGACACAAGCTCCAAAGCGCCAACGGCTCAGCT

CTCCAATGCACCGTGAACCGCTTGACAAGAACCCATCTGCCGGCGCTGCT

CCCATCCGTCTCCCGCCCACTCCTCCATTGCGCCCCGGCTCCGGCTTCCA

CAGCGCCGGCCACTCGCCCTCGAGCTCCATCTCATCCATCTCGATGATCA

AGTCCGAGTACCCGGCACCACCATCAGCTCCAGTCTCTCTTCCGGGCCTT

CCCAGCCCAACCGACCGCTCGTCCATCTCGAGCCAAGGGTCTGCGCCGCA

GCACCAGCATGGTCCCTACGCCTCGCCAGCTCCCAGCGTGGCGCCCTCTT

ACTCCTCGCCCGTTGAGCCCTCACCCTCATCGGCAATGTACTACCAACAC

CAGCGGCCCGCATCCTCAGGCACATACCAGGCTCCTCCACCCCCGCCGCA

ACACCAGCCCATGATCTCGCCCGTGACACCGGCCTGGCAGCACCACCACT

ACTTCCCTCCTTCCTCAAACACACCCTACCAGCAGAACCACGACCGATAT

ATCTGCCGCACCTGCCACAAGGCGTTCTCGCGGCCCTCGAGTCTGCGCAT

CCACAGCCATAGCCACACCGGCGAGAAGCCATTTCGGTGCACACATGCCG

GATGCGGCAAAGCCTTTAGTGTACGGAGCAACATGAAGCGCCATGAGCGC

GGCTGCCATACCGGGAGGGCTGTCGCGATGGTGTAA

Locus AN8741.2 Encoding $C_2H_2$ Type Transcription Factor is Mutated in RM7 (mtfA) Mutants Seven revertant mutants were generated capable of restoring NOR (orange color intermediate used an indicator of toxin biosynthesis) by chemical mutagenesis of RDAE206 strain which does not have veA gene and does not produce NOR. Genetic and linkage group analysis among these mutants indicated that all the mutants belongs to different linkage groups. Mutation in mtfA restored the production of NOR (FIG. 1). In order to identify possible other regulatory elements acting downstream of veA gene in the ST biosynthetic pathway, the mutated gene in RM7 mutant was analyzed. In order to make sure RM7 mutant carries a single nucleotide mutation in particular gene, an RM7 mutant was crossed with RAV-Pyro2 that lacks veA and stcE genes. However, the heterokaryon of this cross did not produce cleistothecia. Thus, an RM7 mutant was crossed with RAV-pyrol which lacks the only stcE gene. Progeny analysis of crosses between RM7 and RAV-pyrol mutants clearly showed that a mutation occurred in a single locus or very closely linked genes in the RM7 mutant.

Figure 2:
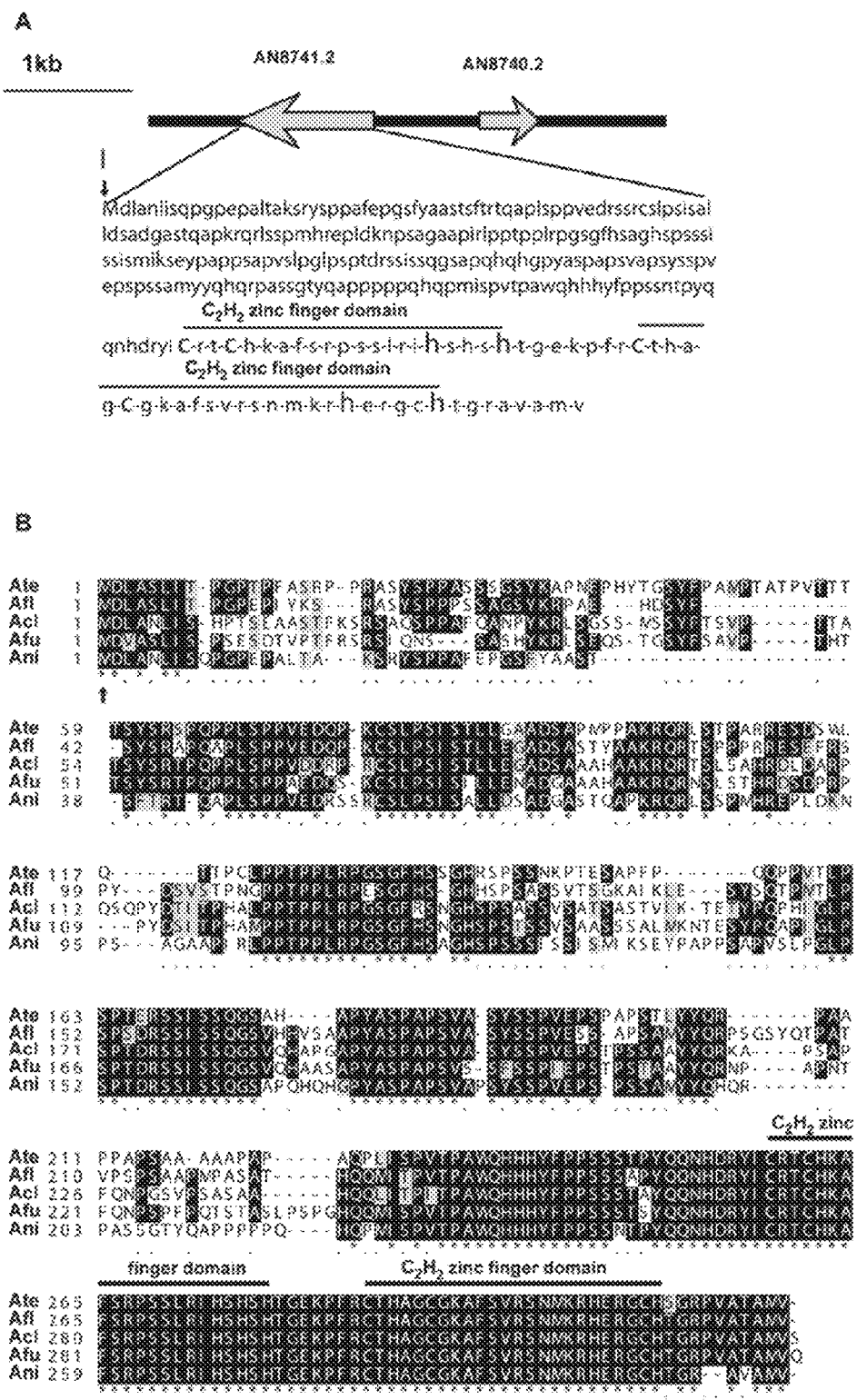
FIG. 2 RM7 mutant has single gene mutation at locus AN8741.2 Map of mtfA gene. (A) Two solid horizontal arrows indicate the two coding regions in the genome fragment of the genomic library plasmid pRG3-AMA-NOT1 that complement the RM7-R2: The coding regions are locus AN8741.2 encoding a putative $C_2H_2$ zinc finger domain transcription factor and locus AN8741.2 encoding a hypothetical proteins. Sequencing of the corresponding region in the RM7 revealed that mutation occurred at Locus AN8741.2 designated as mtfA gene. Vertical arrow indicates mutated amino acid in putative $C_2H_2$ zinc finger domain containing protein as result of point mutation at start codon (ATG to ATT resulting change of methonine to isoleucine). The protein sequence (SEQ ID NO: 74) contains two zinc finger domains represented in lines. (B) Sequence alignment. The amino acid alignment of mtfA gene of A. nidulans (Ani) (SEQ ID NO: 74) with putative homologues of A. terreus (Ate) (SEQ ID NO: 75), A. flavus (Afl) (SEQ ID NO: 76), A. clavatus (Acl) (SEQ ID NO: 77) and A. fumigates (Afu) (SEQ ID NO: 78) were analyzed using ClusterW (http://www.ebi.ac.uk/Tools/clustalw2/index.htm) land boxshade (http://www.ch.embnet.org/software/BOX_form.html) multiple sequence alignment software programs. WA of A. nidulans and its homologs having $C_2H_2$ zinc finger domain are underlined. Upward arrow indicates the amino acid metheonine at the position first amino acid of MtfA is converted to isoleucine and protein synthesis could have started using the next methonine as a start codon.

The mutated gene in the RM7-R2 progeny strain (sup–, ΔsteE), obtained as a result of a cross between RM7 and Rav-pyrol, not only brought about defective conidiation but also produced pinkish pigmentation instead of orange pigmentation on OMM. This could be due to an unknown effect caused by a suppressor gene mutation. Thus, RM7-R2 progeny were used to identify the mutated gene using genomic DNA library complementation (OSHEROV and MAY 2000). Defective conidiation/normal conidiation phenotype and pink/bright orange pigmentation were used as two selection markers for selection of positive transformants directly on the transformation medium, with assumption that the positively complemented strain would appear as full conidiation and produce orange color pigmentation on OMM medium. Upon transformation of RM7-R2 progeny with the genomic library, several positive transformants were obtained that restored conidiation and bright orange color pigmentation on OMM medium. From the positive transformants, Plasmid DNA were rescued, and sequenced. Sequencing of these rescued plasmids indicated that same kind of plasmids was recovered in independent transformants and the genomic fragment in the plasmid contained two hypothetical proteins: one is putative $C_2H_2$ finger domain protein, and another one is unknown hypothetical protein. In order to find out where exactly the mutation happened in the RM7 mutant, the corresponding genomic sequences were amplified from RM7 mutant and sequence-analyzed. Sequence analysis indicated that a gene encoding $C_2H_2$ finger domain containing a gene (designated as mtfA) is mutated and the mutation is G-T transversion at nucleotide 3 of ORF of mtfA, changing start codon from ATG (methionine) to ATT (isoleucine) of MtfA (FIG. 2). The amino acid sequence of *A. nidulans* MtfA revealed significant identity with orthologous protein from other *Aspergillus* spp such as *A. clavatus* (64%), *A. oryzae* (64% identity), *A. niger* (62%) *A. terreus* (61%), *A. flavus* (61) %, and *A. fumigates* (59%) (FIG. 2). MtfA is also conserved in other Acomycetes. No MtfA orthologous protein was found in *Saccharomyces cerevisiae*. Similarly, there are no orthologous proteins of MtfA in the plant and animal kingdoms.

Figure 3:
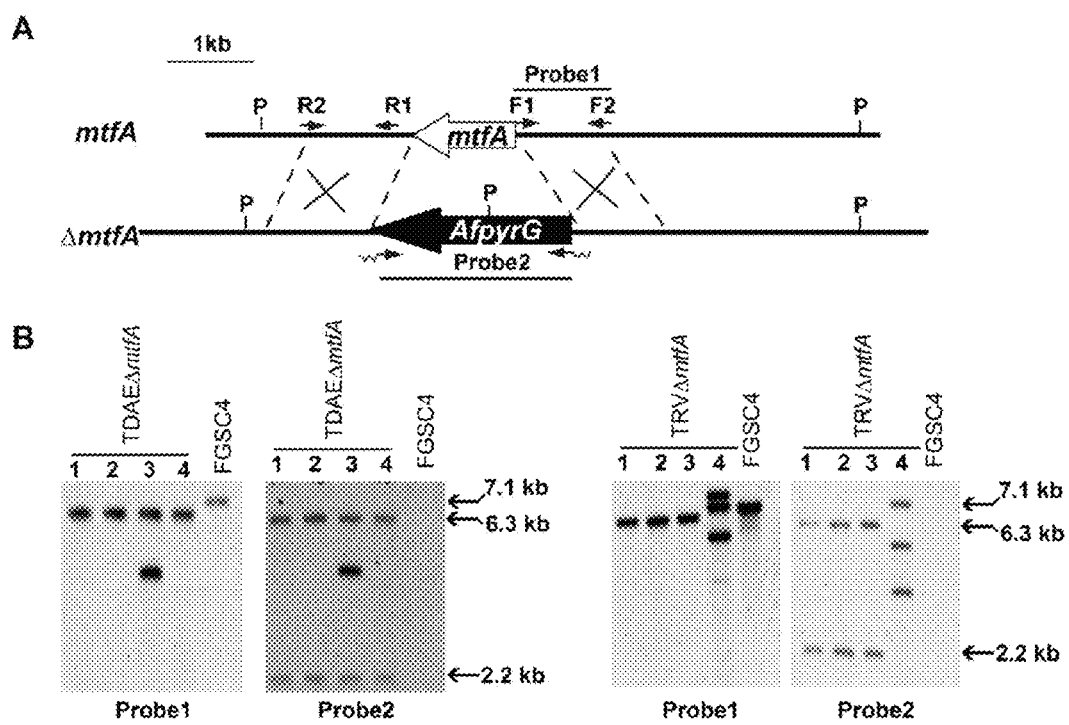
FIG. 3 Targeted mtfA deletion. (A) Diagram showing PstI sites (P) in the wild-type mtfA locus, and the same locus after gene replacement of mtfA by the A. fumigatus pyrG gene (AfpyrG), used as selection marker for fungal transformation. Recombination events between the flanking regions are indicated with crosses (X). Primers used for the construction of the deletion cassette are indicated by small arrows as described by FGSC. Fragments used as probe templates for Southern blot analyses are also shown. (B) Southern blot analyses. The ΔmtfA deletion construct was transformed in RDAE206 and RJMP 1.49 strains (Table 4). PstI digested genomic DNA of FGSC4 wild type (WT) and transformants, TDAEΔmtfA (ΔveA, ΔmtfA) and TRVΔmtfA (veA+ΔmtfA), was hybridized with probe P1, containing 5' flanking sequence of mtfA, and probe P2, containing AfpyrG coding fragment. TDAEΔmtfA transformants #1, 2 and 4 present the correct band pattern. TRVΔmtfA transformants #1, 2 and 3 present the correct band pattern.

Verification of the Generated mtfA Deletion Mutants by DNA Analysis and Effects of the mtfA Deletion Mutation on NOR Production To make sure that NOR production in RDAE206 strain is indeed due to point mutation of mtfA, and also to assess the effect of complete deletion of mtfA on ST synthesis, RDAE 206 and wild-type strain (RJMP1.49) with veA+ genetic background for complete deletion of the mtfA gene were used. A mtfA gene replacement construct was transformed into RDAE206 strain (FIG. 3) and RJMP1.49. The gene replacement was confirmed by Southern blot analysis. (FIG. 3).

A RDAE206 ΔmtfA mutant produces NOR as do RM7 mutants (FIG. 1) OMM and GMM medium, indicating mtfA gene functions in connection with veA and regulates mycotoxin synthesis.

Figure 4:
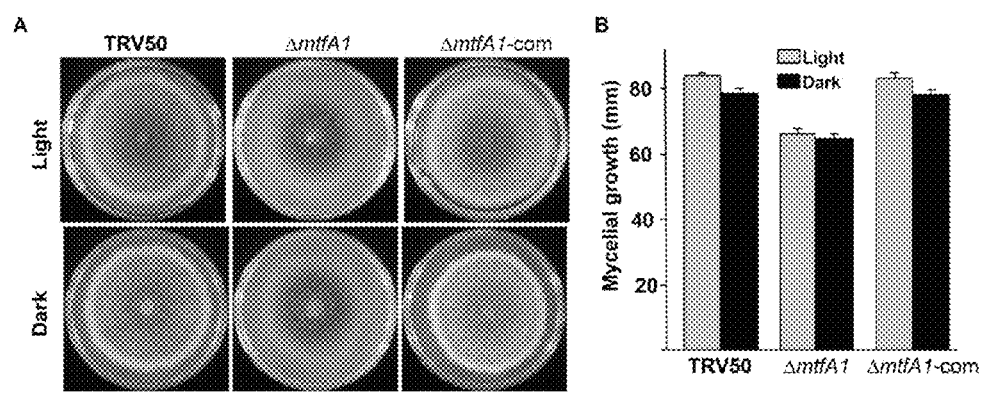
FIG. 4 ΔmtfA mutant is defective in growth. (A) Mycelial growth: Approximately 500 conidia of each strain were inoculated in the center of the GMM plates and incubated at 37° C. in dark and light conditions for 6 days. (B) Quantification of colony diameter of ΔmtfA strains and control strains on GMM.
Figure 5:
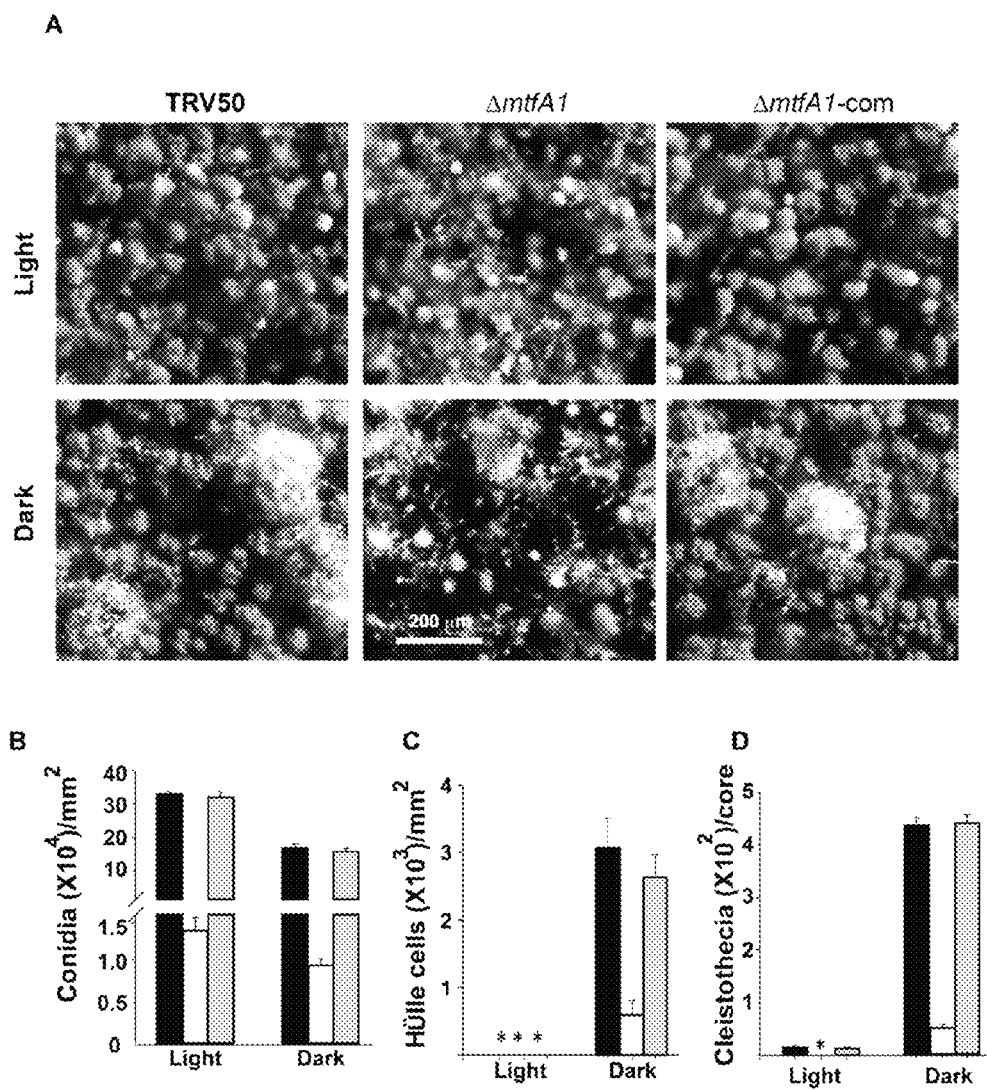
FIG. 5 ΔmtfA mutant is defective in asexual and sexual development. Conidiogenesis: strains grown in dark as described in 4(A) were observed for overall development of conidial head formation. Pictures of conidial masses were taken at 2 cm away from the point of inoculation using dissecting microscope. Quantitative analysis of asexual reproduction in ΔmtfA mutant. A 7-mm-diameter core was removed at 2 cm away from the point of inoculation from culture grown as described in FIG. 4(A) and homogenized in water. Conidia were counted using a hemacytometer (B) Values are means of three replications. Error bar indicates standard errors. (C) & (D). Quantitative analysis of sexual reproduction: Strains grown as described in FIG. 4(A) were used for the counting Hulle cells (C) and cleistothecia production (D). Hulle cells were counted simultaneously in the same core that was used for conidial counting in FIG. 5(B). Cleistothecia were counted after spraying the mycelial disc of 15 mm diameter (taken at 2 cm away from the point of inoculation from the cultures grown as described in FIG. 4(A) with 70% ethanol under dissecting microscope. Values are means of three replications. Error bar indicates standard errors. Asterisks indicate no Hulle or cleistothecia production.
Figure 6:
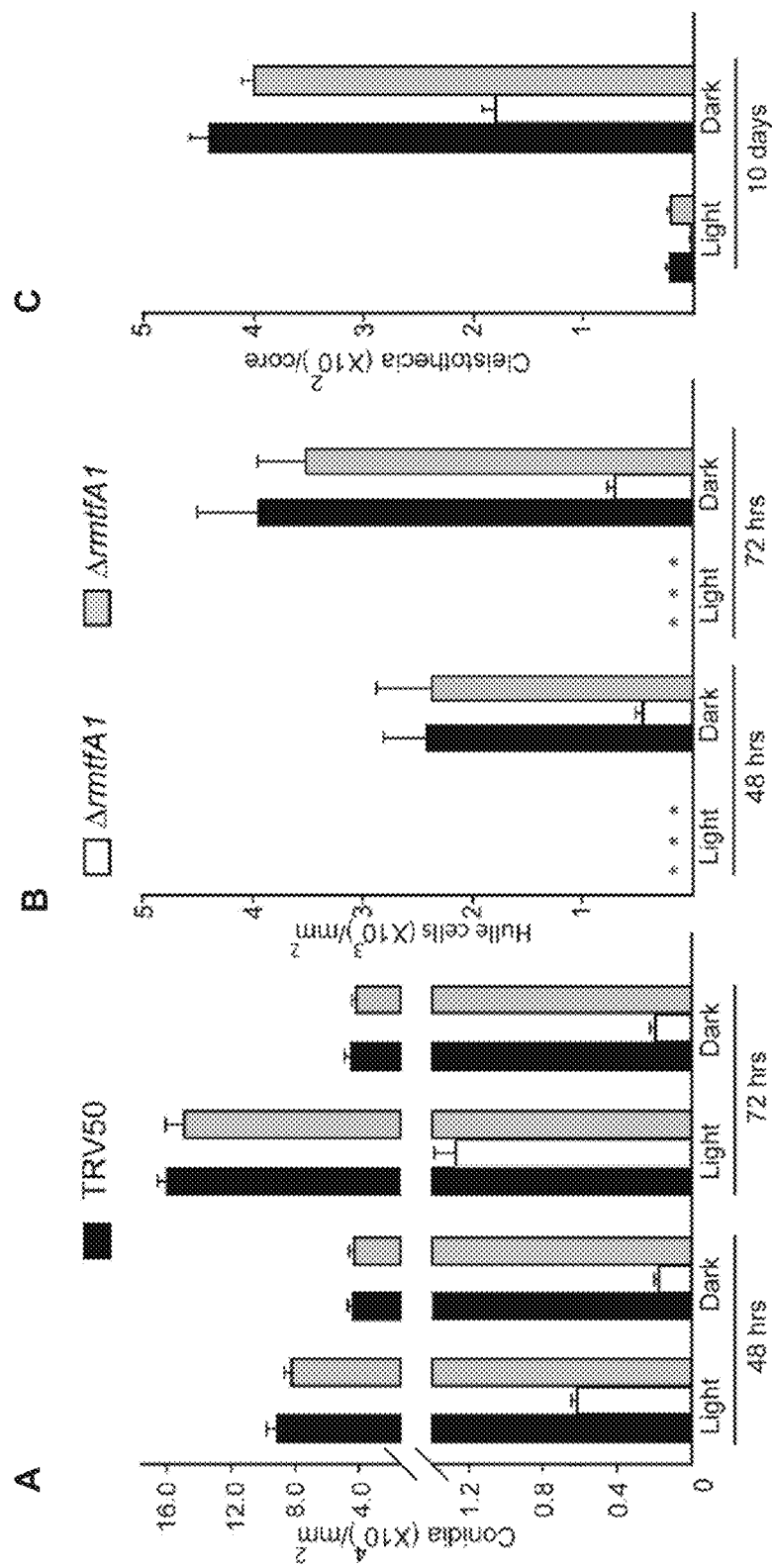
FIG. 6 Analysis of asexual and sexual reproduction of ΔmtfA mutant by top agar inoculation. Quantitative analysis of asexual reproduction in ΔmtfA mutant. Strains were spread-inoculated with 5 ml of top agar containing $10^6$ conidia ml$^{-1}$ on GMM and incubated at 37° C. in dark or light conditions. (A) Culture discs were taken randomly from the plates and the total number of conidia was counted as described in FIG. 5(B). Values are means of three replications. Error bar indicates standard errors. Quantitative analysis of sexual reproduction: Strains grown as described above were used for assessing Hulle cells (B) and cleistothecia production (C). Culture discs were taken randomly from the plates and the total number of Hulle cells and cleistothecia were counted as described in FIGS. 5(C) and 5(D). Values are means of three replications. Error bars indicate standard errors. Asterisks indicate no hulla or cleistothecia production.
Figure 7A:
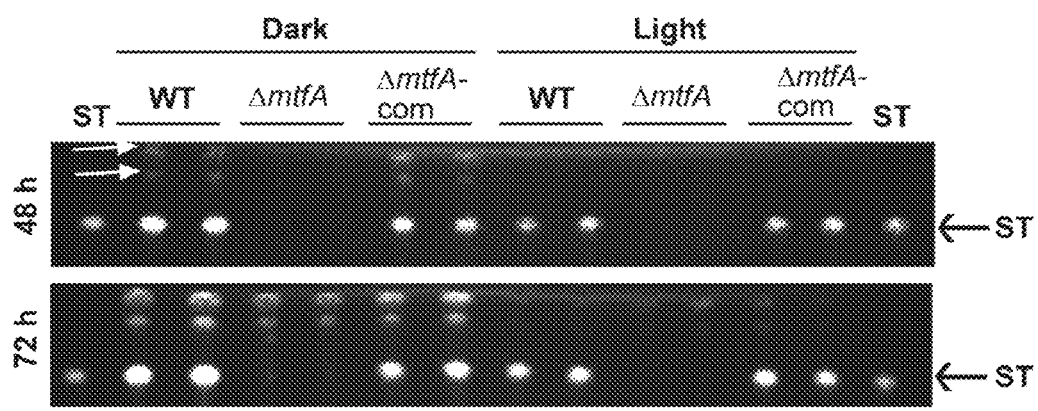
FIG. 7 Effects of mtfA deletion on ST production in A. nidulans strains with a veA+ allele. (A) TLC analysis showing ST production in GMM cultures. Wild type (WT) veA+ control (TRV50.2), ΔmtfA (TRVpΔmtfA) and ΔmtfA-com complementation strain (TRVΔmtfA-com) were spread-inoculated with 5 mL of top agar containing $10^6$ conidia mL$^{-1}$ and incubated at 37° C. in the dark or in the light for 48 h and 72 h. ST was extracted and analyzed by TLC as described in the Material and Methods section. White arrows indicate unknown compounds whose synthesis is also affected by the presence or absence of mtfA. (B) Effect of the mftA deletion on aflR and stcU expression. Wild type (WT) veA+ control (TRV50.2), ΔmtfA (TRVpΔmftA) and ΔmtfA-com complementation strain (TRVΔmtfA-com) were inoculated in liquid GMM. Mycelia were collected 24 h and 48 h after inoculation. Cultures were grown in a shaker incubator at 37° C. at 250 rpm. Expression of aflR and stcU was analyzed by Northern blot. 18S rRNA serves as loading control. Asterisk indicates not detected. (C) TLC showing accumulation of ST in the cultures described in (B). Densitometries were carried out with the Scion Image Beta 4.03 software. doi:10.1371/journal.pone.0074122.g003 (D, E, F).
Figure 7B:
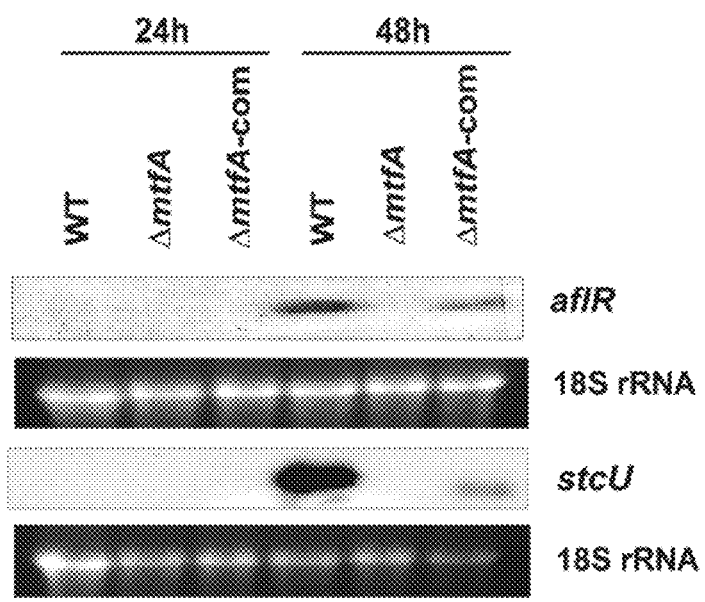
Figure 7C:
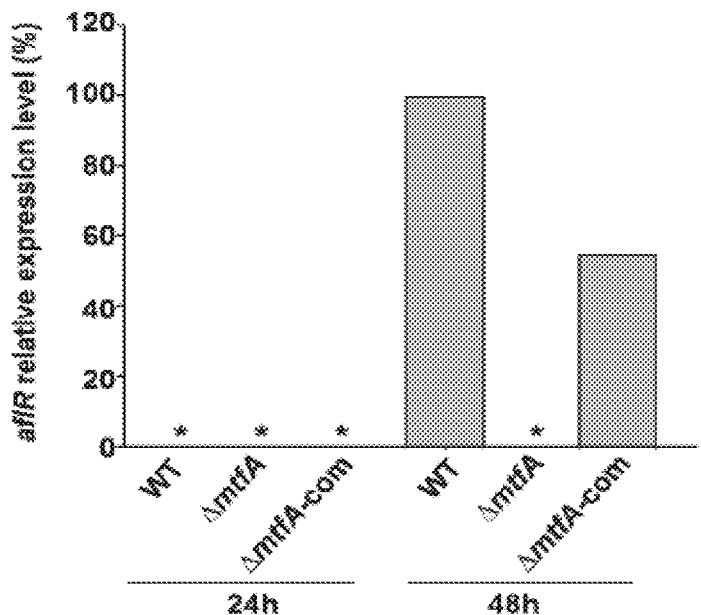
Figure 7D:
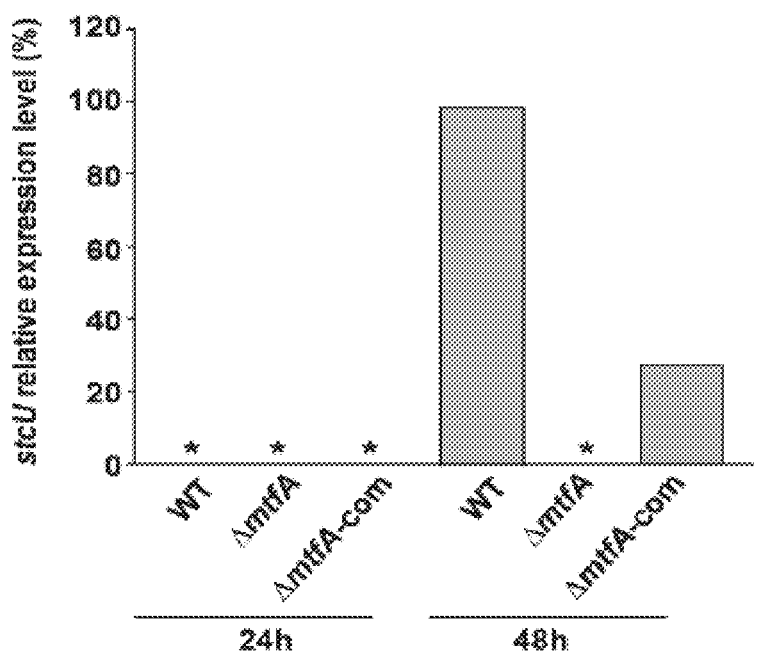
Figure 7E:
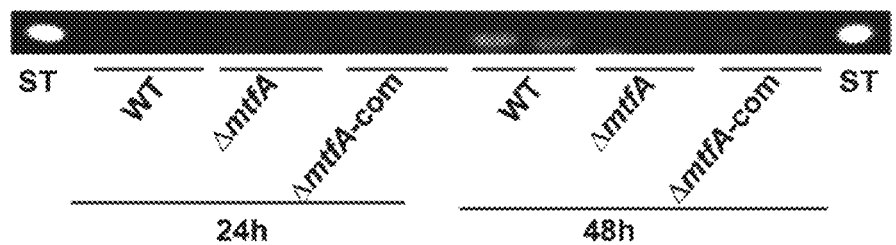
Figure 7F:
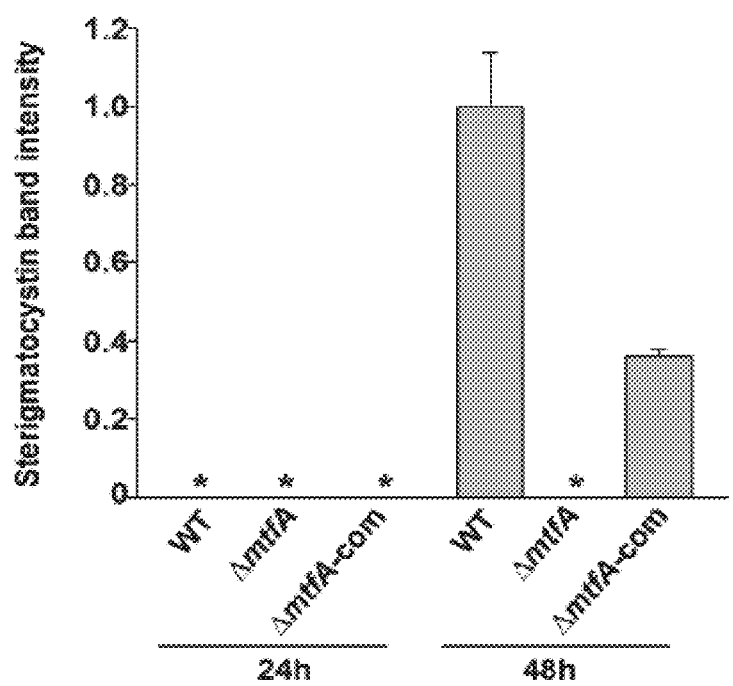

Deletion of mtfA Results in a Slight Decrease on Fungal Growth (FIG. 4) and Defects in Sexual and Asexual Development (FIGS. 5 and 6)

mtfA is a positive regulator of both asexual and sexual development in *A. nidulans*. Deletion of mtfA in *A. nidulans* results in a reduction of conidiation and cleistothecia (fruiting bodies) formation. Complementation of the deletion mutant with the mtfA wild-type allele rescues wild-type morphogenesis.

mtfA Deletion Decreases ST Production in a Strain with a veA Wild-Type Allele

Mutation of mtfA (RM7 strain) and deletion of mtfA (RDAE206ΔmtfA) was reported to restore NOR synthesis in a ΔveA genetic background. Mutation of mtfA in a veA1 genetic background (RM7-R2 strain) also synthesized the same level of NOR as ΔmtfA did. A question was how does mtfA function in ST synthesis in a veA+(veA wild type) genetic background. So, the production of ST levels was determined in an ΔmtfA mutant, veA+. ST analysis indicated that a ΔmtfA mutant does not produce ST, whereas, wild type (TRV50) and complemented strain (ΔmtfA+com) produced higher levels of ST at 48 hrs of incubation on GMM solid cultures (FIG. 7).

The expression of transcript levels of the aflR and stcU gene involved in the ST biosynthetic pathway were analyzed. Northern blot analysis of aflR and stcU transcripts clearly indicated that these genes expression is not observed in ΔmtfA deletion mutant whereas aflR and stcU expression is clearly noticed in its isogenic wild-type and complemented strains (FIG. 7).

Figure 8:
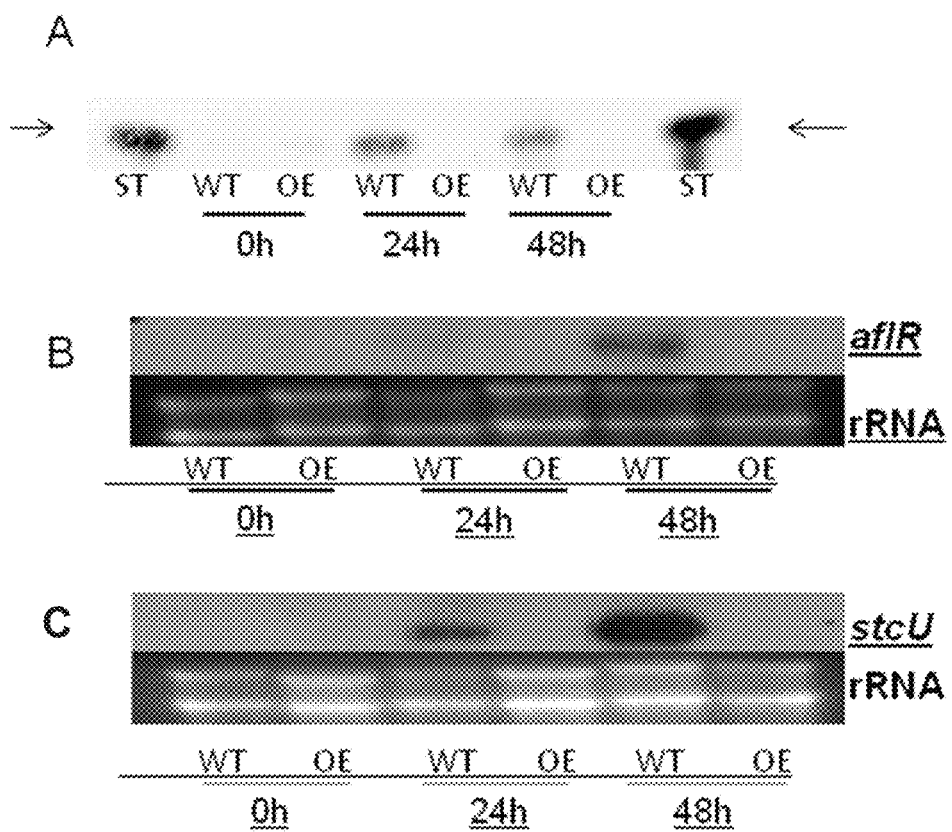
FIG. 8 Overexpression of mtfA suppresses the ST production on GMM medium. TLC analysis of ST production. (A) Strains were inoculated in GMM liquid medium at $10^6$ conidia ml$^{-1}$ and grown for 16 hrs. Mycelia were collected and equal amounts of mycelia were inoculated in TMM agar medium. The cultures were further incubated for 24 and 48 hours. Mycelia were collected and toxin analysis was carried out as described in the experimental procedure. Analysis of aflR (B) and stcU (C) expression by Northern blot. The cultures (A) were used for the expression of aflR and stcU analysis. Mycelia were collected at 0 hrs, shifting time-from liquid GMM to solid TMM, 24 and 48 hours of incubation on TMM. Total RNAs were extracted and expression of aflR and stcU were analyzed. rRNA serves as a loading control.

A mtfA over-expressing strain, mtfA-OE, where expression mtfA is under the control of the alcA promoter. Initially, the strains were grown on liquid GMM for 16 hrs. After shifting the mycelium to the induction medium, the mtfA-OE strain produced less amount of ST compared to the isogenic wild-type strain after 24 and 48 hours of induction. Similarly, the expression analysis of aflR and stcU was analyzed for confirmation of the ST synthesis data. Northern blot analysis of aflR and stcU indicated that the expression of aflR and stcU was suppressed at 24 and 48 hours of incubation (FIG. 8) under inducing conditions for mtfA overexpression.

mtfA Positively Regulates Penicillin Biosynthesis.

Figure 9:
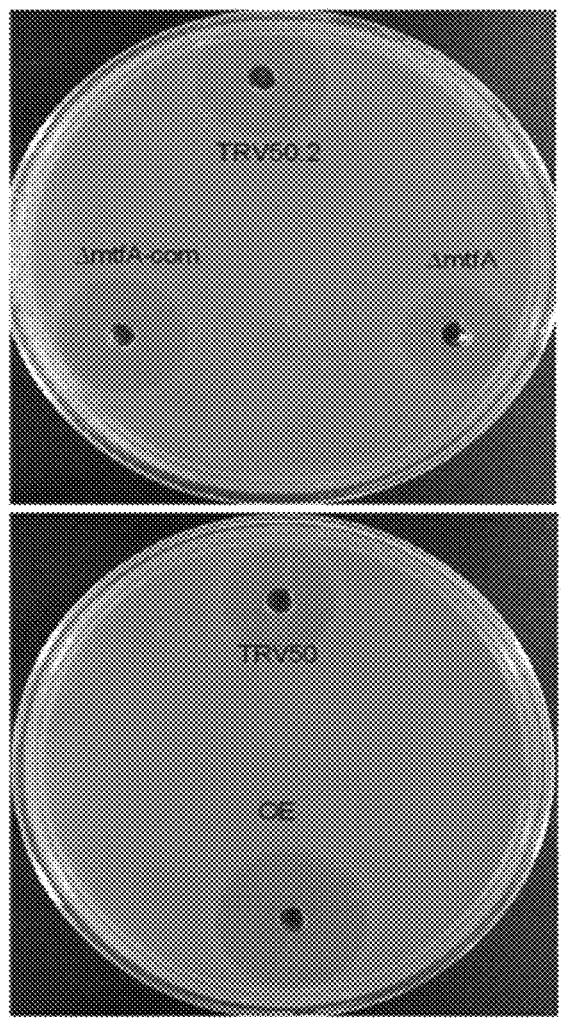
FIG. 9 MtfA regulates penicillin biosynthesis. Deletion of mtfA reduces penicillin production (upper photo) while overexpression of mtfA increases penicillin production (lower photo). The experiment was repeated several times with the same results.

VeA regulates biosynthesis of penicillin (PN) genes and mtfA is also influenced by VeA with regard to ST production. To see whether mtfA regulates the PN production, the amount of PN production in ΔmtfA strains was compared with isogenic wild-type strains TRV50.2 and its complemented strain ΔmtfA–com. Deletion of mtfA significantly reduced the level of PN production compared to its isogenic wild-type strain TRV50.2 (FIG. 9). Overexpression of mtfA showed enhanced levels of PN compared to its isogenic wild-type stain TRV50. mtfA positively regulates PN production (FIG. 9).

mtfA Regulates the Expression of the Terrequinone Gene.

Figure 10:
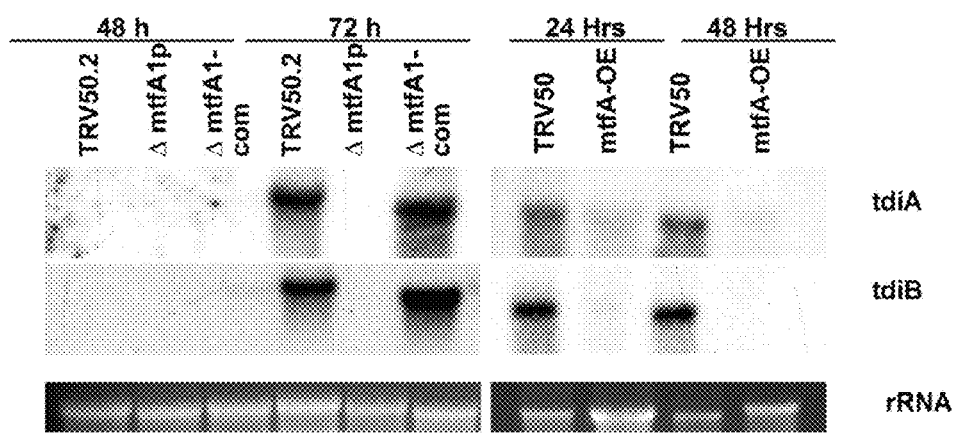
FIG. 10 mtfA controls the expression of genes involved in the synthesis of other secondary metabolites. Deletion or over-expression of mtfA decreases the expression of terraquinone gene tdiA and tdiB. Left panels, strains (WT, deletion mtfA and complementation strain) were grown in GMM liquid shaken cultures (inoculum: $10^6$ conidia $ml^{-1}$) and incubated at 37° C. for 48 and 72 h. Right panels, stains (WT and overexpression mtfA) were inoculated in GMM liquid medium at $10^6$ conidia $ml^{-1}$ and grown for 16 hrs. At that time, mycelia were collected and equal amounts of mycelia were inoculated in TMM liquid medium. The cultures were grown for additional 24 and 48 hours after the shift. Total RNAs were extracted and expression of tdiA and tdiB were analyzed. rRNA serves as a loading control.

In order to determine if mtfA is also involved in regulation of terrequinone, anti-tumor compound, biosynthesis, the expression of mRNA levels of tdiA and tdiB in the terrequinone biosynthetic cluster were analyzed. At 48 and 72 h of incubation in GMM, the expression of tdiA and tdiB were noticed in TRV50.2 and ΔmtfA–complementation strains, however, the ΔmtfA did not exhibit expression of tdiA nor tdiB mRNA transcript at 48 or 72 h of incubation on GMM (FIG. 10). The mtfA-OE strain showed lower levels of both tdiA and tdiB transcripts compared to the isogenic wild-type strain, TRV50 at both 24 and 48 hours after induction shift for mtfA overexpression (FIG. 10).

MtfA Subcellular Localization

MtfA is located mainly in nuclei.

EXAMPLES

Examples are provided for illustrative purposes and are not intended to limit the scope of the disclosure.

Example 1

The Putative $C_2H_2$ Transcription Factor MtfA is a Novel Regulator of Secondary Metabolism and Morphogenesis in *Aspergillus nidulans*

Locus AN8741.2, mutated in RM7, encodes a putative $C_2H_2$ type transcription factor. Seven revertant mutants (RMs) were generated capable of restoring normal levels in the production of the orange ST intermediate norsonolinic acid (NOR) in a ΔstcE strain lacking the veA gene (RDAE206). Classical genetics analysis revealed that these RMs belong to different linkage groups. The mutated gene in RM7 that restores toxin production in a deletion veA genetic background (was subsequently identified, see FIG. 1). The mutation in RM7 was recessive and the specific affected locus was found by complementation of RM7-R2 with an *A. nidulans* genomic library (pRG3-AMA1-NOT1). Several positive transformants showing wild-type phenotype were obtained. Sequencing of the rescued plasmids from these fungal transformants and comparison of these sequences with the *A. nidulans* genomic database (http://www.aspgd.org) by BLAST analysis indicated that they contained the same genomic insert including two ORFs, one of them encoding a putative $C_2H_2$ finger domain protein, and another encoding an unknown hypothetical protein (FIG. 2). In order to determine where the mutation was located in RM7, the corresponding genomic DNA fragment was PCR-amplified. Sequencing of this PCR product revealed that the mutation occurred in a gene encoding the novel putative $C_2H_2$ transcription factor, that we designated mtfA (master transcription factor A). The mutation was a G-T transversion at nucleotide +3 of the mtfA coding region, changing the start codon from ATG to ATT (FIG. 2A).

MtfA Orthologs are Present in Other Fungal Species

Figure 11:
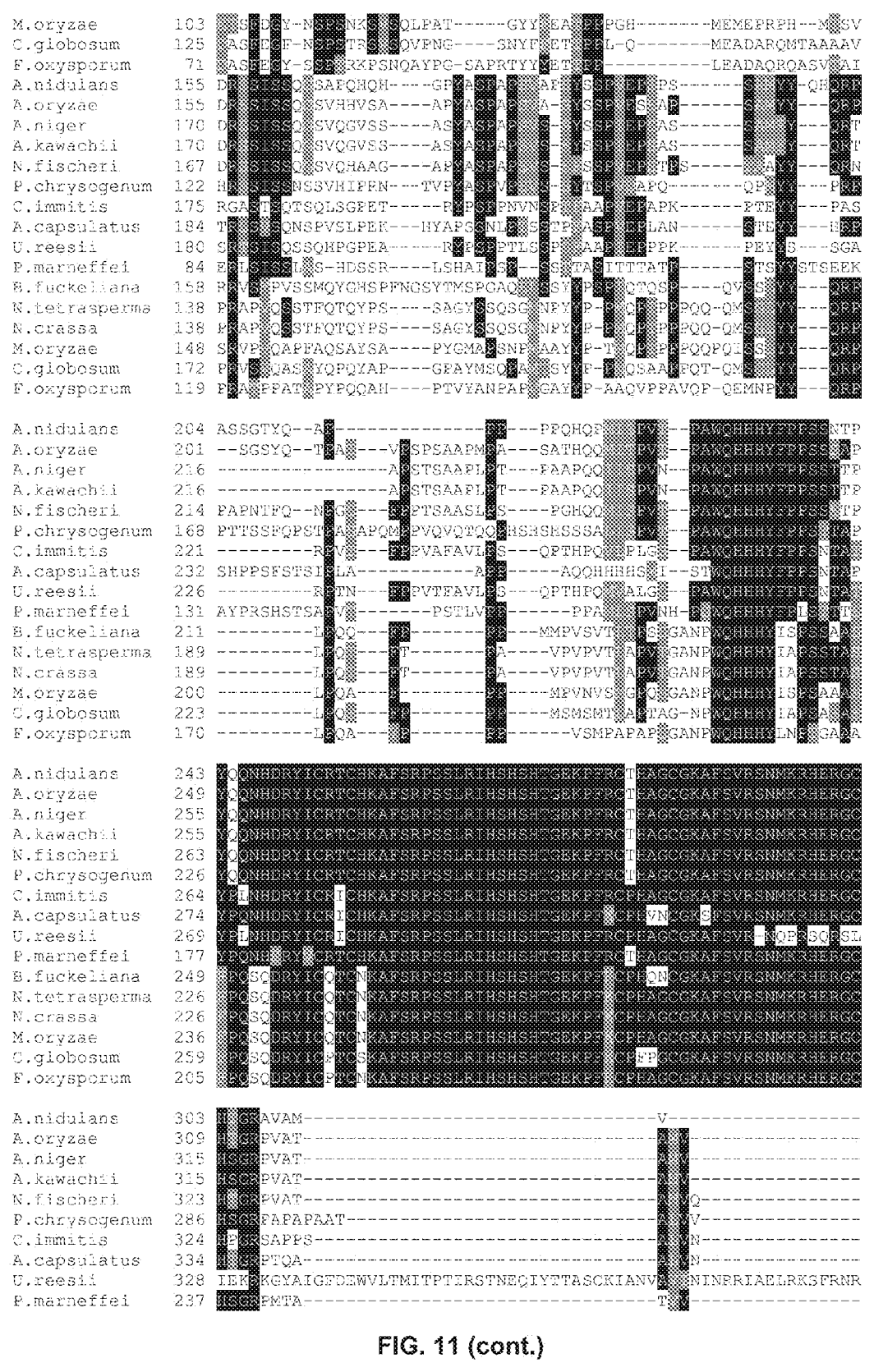
Figure 12:
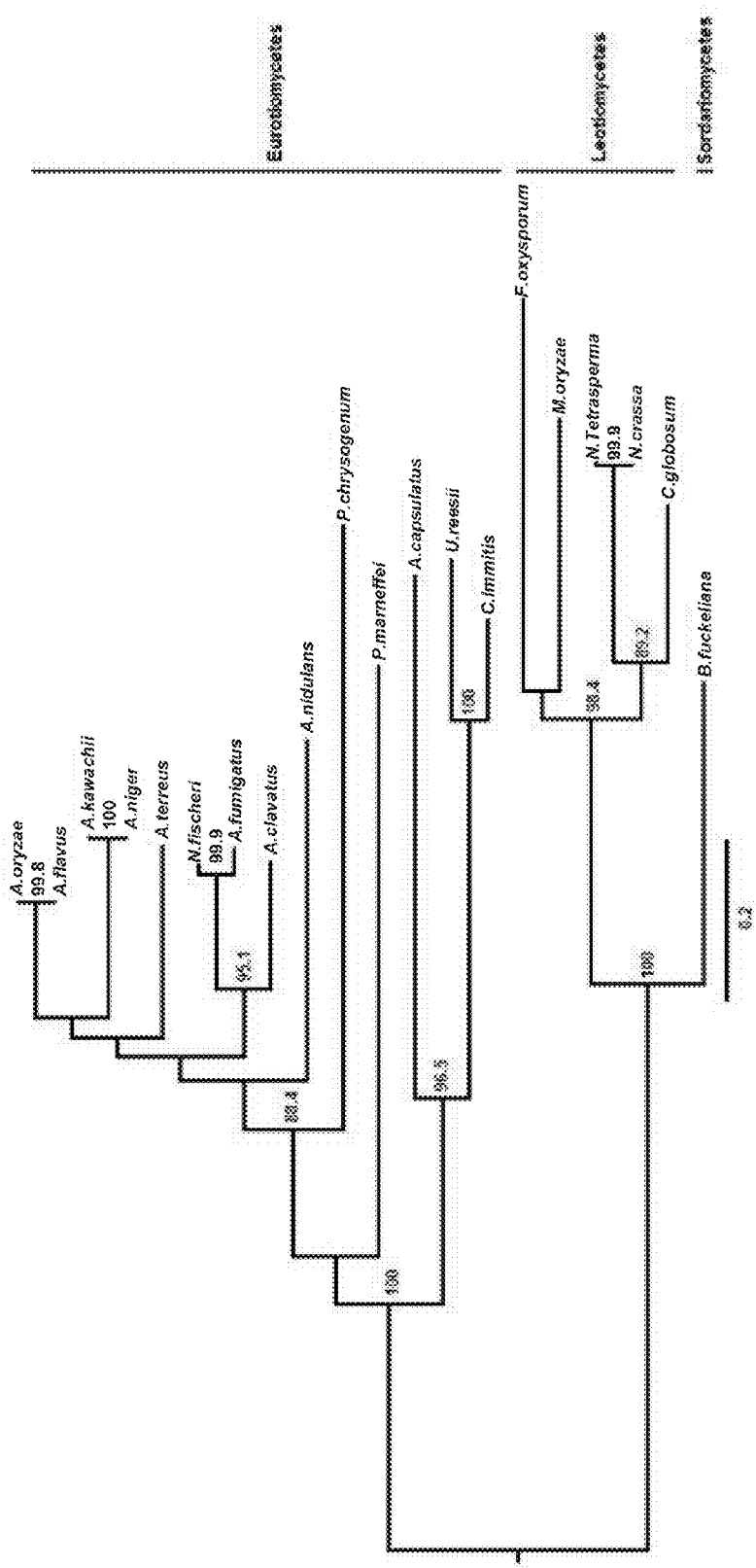
FIG. 12 Maximum-Likelihood (ML) phylogenetic tree inferred from ortholog sequences of MtfA (*A.nidulans*) across genomes from several fungal species. Protein alignment was done with MUSCLE; aLRT (approximate Likelihood Ratio Test) branch support values were calculated with PhyML v3.0 and the tree was plotted using FigTree v1.4.0. Only alRT branch support values >80% are indicated. The protein sequences used are as follows: *Aspergillus oryzae* (*A.oryzae*), *Aspergillus flavus* (*A. flavus*), *Aspergillus kawachii* (*A.kawachii*), *Aspergillus niger* (*A.niger*), *Aspergillus terreus* (*A. terreus*), *Neosartorya fischeri* (*N.fischeri*), *Aspergillus fumigatus* (*A.fumigatus*), *Aspergillus clavatus* (*A.clavatus*), *Aspergillus nidulans* (*A.nidulans*), *Penicillium chrysogenum* (*P.chrysogenum*), *Penicillium marneffei* (*P.marneffei*), *Ajellomyces capsulatus* (*A. capsulatus*), *Uncinocarpus reesii* (*U.reesii*), *Coccidioides immitis* (*C. immitis*), *Fusarium oxysporum* (*F.oxysporum*), *Magnaporthe oryzae* (*M.oryzae*), *Neurospora tetrasperma* (*N.tetrasperma*), *Neurospora crassa* (*N.crassa*), *Chaetomium globosum* (*C.globosum*) and *Botryotinia fuckeliana* (*B.fuckeliana*). NCBI (National center for Biotechnology Information) accession numbers for all sequences utilized in these analyses are shown in (Table 7).

The deduced amino acid sequence of *A. nidulans* MtfA revealed significant identity with ortholog proteins from other *Aspergillus* spp., such as *A. clavatus* (64% identity), *A. terreus* (61%), *A. flavus* (61) %, or *A. fumigatus* (59%). Further analysis of other fungal genomic databases indicated that MtfA is also conserved in other fungal genera in Ascomycetes (Table 7, FIGS. 11 and 12). The $C_2H_2$ DNA binding domain is highly conserved among these putative orthologs. A MtfA ortholog was not found in the strict-yeast fungus *Saccharomyces cerevisiae*. Similarly, MtfA putative orthologs were not found in plants or animals. Examples of orthologs from other fungal genera are listed in Table 4. An extensive alignment and phylogenetic tree is shown in FIGS. 11 and 12. MtfA orthologs were particularly conserved among *Aspergillus* spp. The MtfA tree topology was consistent with established fungal taxonomy. MtfA presents similarity to other *A. nidulans* $C_2H_2$ DNA binding domain proteins (Table 8), showing the highest similarity with FlbC (25.3% identity in the full protein comparison and 29% identity when comparing the DNA binding domains).

mtfA Regulates Mycotoxin Biosynthesis

To confirm that NOR production in RM7 (ΔveA, X–) was indeed due to a loss-of-function mutation in mtfA, and to assess the effect of this mutation on ST production in a strain with a wild-type veA allele (veA+), a complete deletion of mtfA was performed in RDAE206 (ΔveA) and RJMP1.49 (veA+), obtaining TDAEΔmtfA and TRVΔmtfA strains, respectively (FIG. 3). Deletion of mtfA in these strains was confirmed by Southern blot analysis, using the 5' UTR as probe template P1 (FIG. 3(A)). This probe revealed a 7.1 kb PstI fragment in the wild-type control and a 6.3 kb PstI fragment in the deletion mutants as expected. Also, hybridization with the transformation marker gene used for gene replacement, AfpyrG (specific probe template P2), revealed 6.3 kb and 2.2 kb PstI fragments in mtfA deletion mutants, while these bands were absent in the wild-type control, as predicted.

Similarly to RM7p (ΔstcE, ΔveA, mtfA–) (p, indicates prototrophy), the TDAEpΔmtfA (ΔstcE, ΔveA, ΔmftA) strain shows an increase in NOR production with respect to RDAEp206 (ΔstcE, ΔveA), (FIG. 1). The mutation in mtfA also allowed NOR production in a strain with a veA1 allele, RM7-R2p (ΔstcE, veA1, mtfA⁻), a common veA mutant genetic background used in numerous *A. nidulans* research laboratories that still allows ST production. The levels of NOR production by RM7-R2p were similar to those detected in the isogenic control RAV1p (ΔstcE, veA1).

To elucidate the role of mtfA in mycotoxin biosynthesis in a strain with a veA wild-type genetic background (veA+) ST production was analyzed in the TRV ΔpmtfA strain and compared with that of the isogenic wild-type control strain and the complementation strain. Interestingly, TRVpΔmtfA mutant did not produce ST after 48 h of incubation under both light and dark conditions in the veA wild-type background, whereas the wild type and complementation strain produced clearly detectable levels of ST (FIG. 3(A)). At 72 h only very low levels of ST were detected in the TRVDΔmtfAp culture under these experimental conditions (FIG. 3(A)). In addition, the TLC analysis indicated that deletion of mtfA also resulted in a delay in the synthesis of two additional unknown compounds in cultures growing in the dark (FIG. 3A).

mtfA Controls aflR Expression and Activation of the ST Gene Cluster

Figure 13:
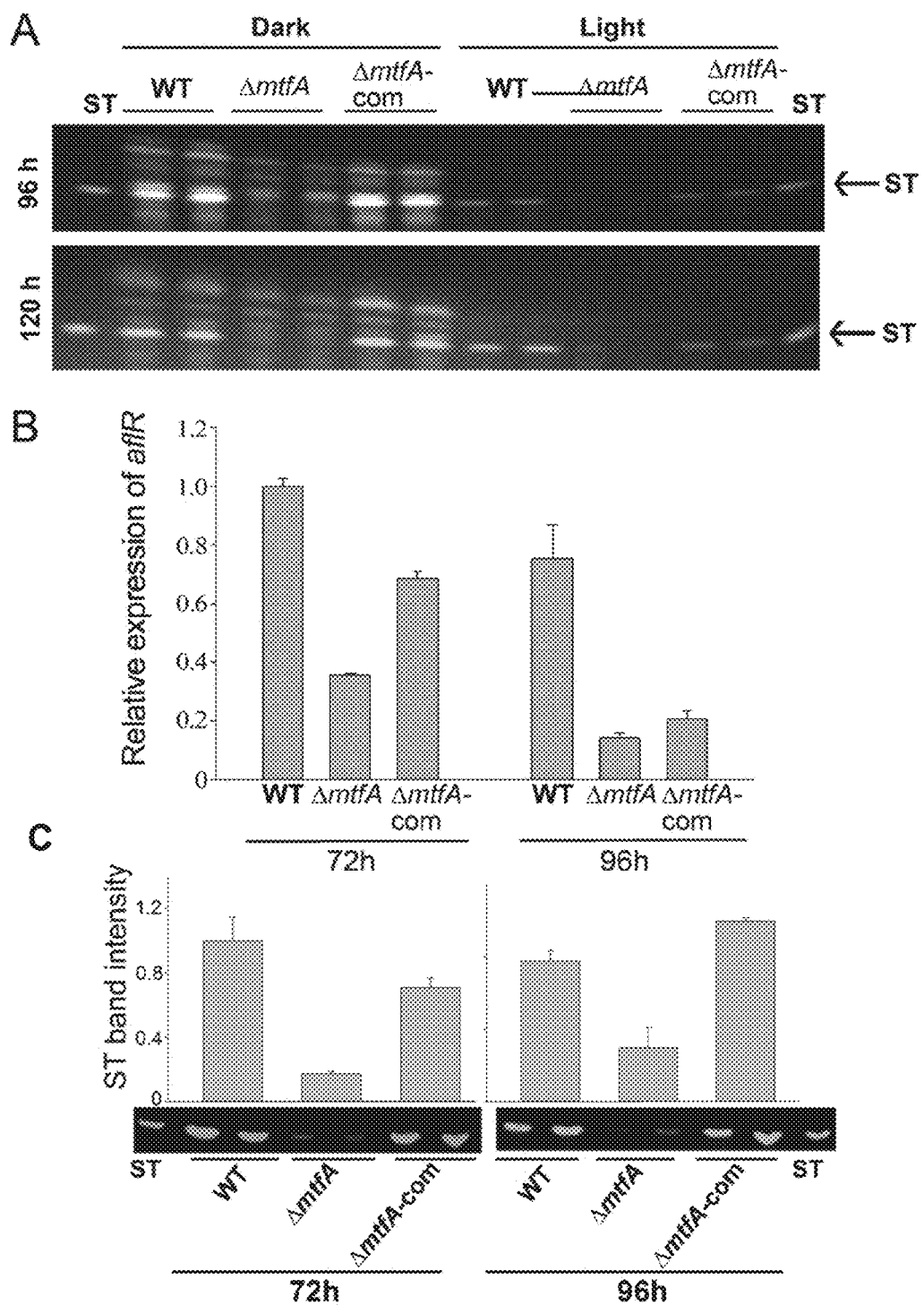
FIG. 13 Effects of mtfA deletion on ST production and aflR expression at late time points. (A) TLC analysis showing ST production in GMM cultures. Wild type (WT) veA+ control (TRV50.2), ΔmtfA (TRVpΔmftA) and ΔmtfA–com complementation strain (TRVΔmtfA–com) were spread-inoculated with 5 mL of top agar containing $10^6$ conidia $mL^{-1}$ and incubated at 37° C. in the dark or in the light for 96 h and 120 h. ST was extracted and analyzed by TLC. (B) Effect of the mftA deletion on aflR expression. Wild type (WT) veA+ control (TRV50.2), ΔmtfA (TRVpΔmftA) and ΔmtfA–com complementation strain (TRVΔmtfA–com) were inoculated in liquid GMM. Mycelia were collected 72 h and 96 h after inoculation. Cultures were grown in a shaker incubator at 37° C. at 250 rpm. Expression of aflR was analyzed by qRT-PCR. (C) A TLC showing accumulation of ST in these cultures and corresponding densitometry is also shown.

Expression of the specific ST regulatory gene aflR, and expression of stcU, gene encoding a ketoreductase that is used as indicator for cluster activation, were analyzed in liquid shaken cultures of wild type, deletion mtfA and complementation strain at 24 h and 48 h after spore inoculation. Neither aflR nor stcU were expressed in the mtfA deletion mutant, while transcripts for both genes accumulated at the 48 h time point analyzed (FIG. 3(B)). The presence of these transcripts coincided with the presence of ST in the control cultures. Mycotoxin was not detected in the mtfA deletion cultures under the experimental conditions assayed (FIG. 3(C)). Analysis of later time points also showed a notable reduction of ST production as well as a reduction in OR expression in the ΔmtfA strain with respect to the controls (FIG. 13), Over-expression of mtfA (alcA(p)::mftA, veA+) also prevented the transcription of aflR and stcU as well as ST production under conditions that allowed the control strains to activate the transcription of ST genes and mycotoxin production (FIG. 13).

Figure 14:
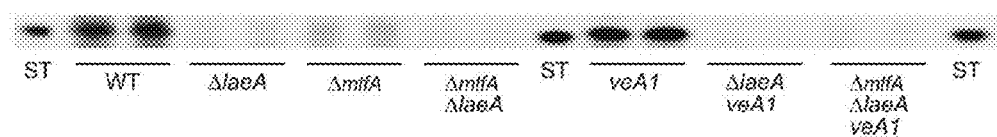
FIG. 14 Deletion of mtfA does not rescue mycotoxin production in ΔlaeA strains. TLC analysis of ST produced by the wild type (WT) veA+ control (TRV50.2), ΔlaeA veA+ (RJW41.A), ΔmtfA veA+(TRVpΔmtfA) and ΔmtfA ΔlaeA veA+ strains (RSD11.2), veA1 (RDIT2.3), ΔmtfA veA1 (RJW46.4), ΔmtfA ΔlaeA veA1 (RSD10.1) grown on GMM at 37° C. for 5 days.

Deletion of mtfA does not Recover Mycotoxin Biosynthesis in a Deletion laeA Genetic Background Since VeA and LaeA proteins can interact in the nucleus and are, at least in part, functionally dependent, whether loss of mtfA results in rescue of ST production in a ΔlaeA strain was investigated. For this purpose, double ΔmtfAΔlaeA mutants were generated in veA1 and veA+ genetic backgrounds by meiotic recombination from crosses between RJW34-1 (pyrG89; wA3; ΔstcE::argB; ΔlaeA:: methG; trpC801; veA1) and TRVΔmtfA (Table 1). TLC analysis showed that deletion of mtfA did not recover ST biosynthesis in the strains with laeA deletion (FIG. 14).

mtfA Positively Regulates PN Biosynthesis by Controlling the Expression of the PN Gene Cluster Results from chemical analysis indicated that mtfA also affects the synthesis of other metabolites (FIG. 18). Based on this finding, whether mtfA controls PN biosynthesis was investigated. The production of this antibiotic in TRVpΔmtfA was evaluated and compared with PN levels in the isogenic wild-type control and complementation strain. A strain of *B. calidolactis* was used as the testing organism. Deletion of mtfA decreases penicillin production approximately 7-fold with respect to the wild type (FIG. 18(A)), indicating that mftA is necessary for wild-type levels of penicillin biosynthesis. Gene expression analysis revealed that acvA, ipnA and aatA, genes in the PN gene cluster, are down-regulated in the mftA deletion mutant (FIGS. 18 (B), (C), (D), (E)) particularly at the 24 h time point (24 h after mycelium is transferred to PN induction medium).

Figure 19A:
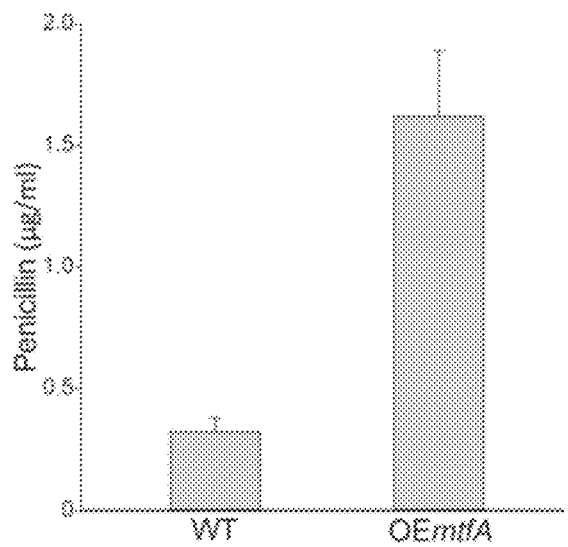
FIG. 19 Over-expression of mftA increases penicillin production. (A) Extracts from wild-type (WT) veA+ control (TRV50.1), and over-epxression (OE) mtfA strain (TRV60) were analyzed for penicillin content as described in Materials and Methods section. (B), (D), (E) qRT-PCR expression analysis of acvA from mycelial samples collected after 24 hours and 48 hours of incubation in PN inducing medium. (C) Northern blot analysis of ipnA and aatA from samples collected after 24 hours and 48 hours of incubation in PN inducing medium. Densitometries were carried out with the Scion Image Beta 4.03 software.
Figure 19B:
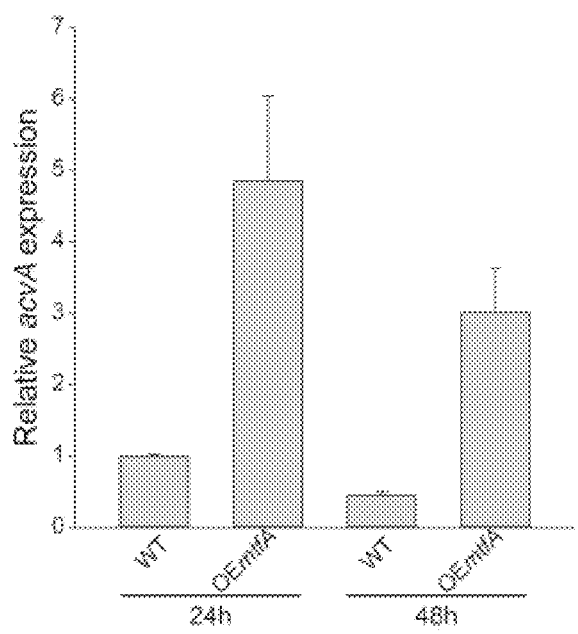
Figure 19C:
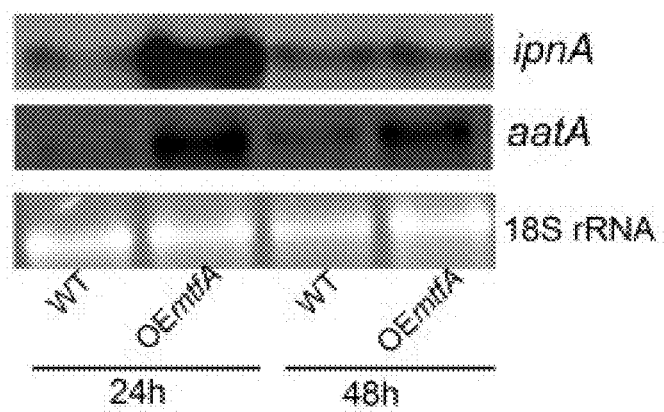
Figure 19D:
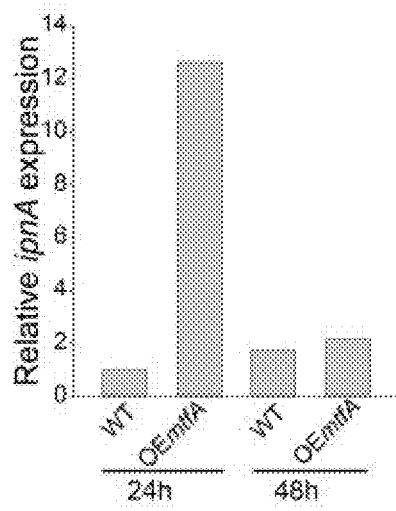
Figure 19E:
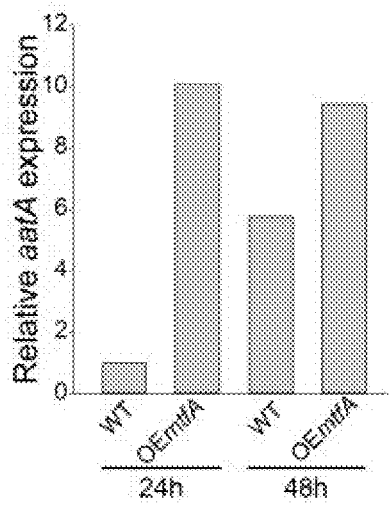

Over-expression of mtfA clearly increases production of PN (approximately 5-fold) with respect to the PN production levels obtained in the wild-type strain (FIG. 19(A)). Expression of acvA, ipnA and aatA, was greater in the mtfA over-expression strain than in the control strain (FIGS. 19 (B), (C). The experiment was repeated several times with similar results.

mtfA Regulates the Expression of Terrequinone Genes

Figure 20A:
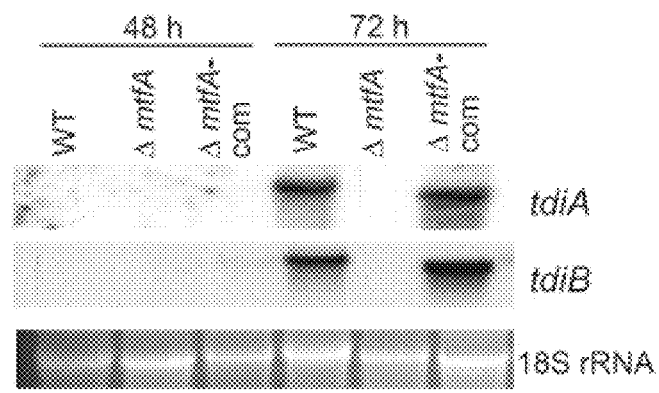
FIG. 20 mtfA is necessary for normal express of terrequinone genes. (A) Wild type (WT) veA+ control (TRV50.2) ΔmtfA and ΔmtfA.com complementation strain (TRV ΔmtfA–com) were inoculated in liquid GMM. Mycelia were collected at 48 hours and 72 hours after inoculation for RNA extraction. Cultures were grown in a shaker incubator at 37° C. at 250 rmp. Expression of tdiA and tdiB was analyzed by Northern blot. 18S rRNA serves as loading control. (B) Isogenic wild type (WT) veA+ control (TRV50.1) and overexpression (OE) mtfA strain (TRV60) were inoculated in liquid GMM and grown from 16 hours. After that, equal amounts of mycelium were transferred to TMM and further incubated for 24 hours and 48 hours. tdiA and tdiB expression was analyzed as (A). Densitometries were carried out with Scion Image Beta 4.03 software for relative expression of tdiA, tdiB and their overexpression (C), (D), (E) and (F). Asterisks indicates not detected.
Figure 20B:
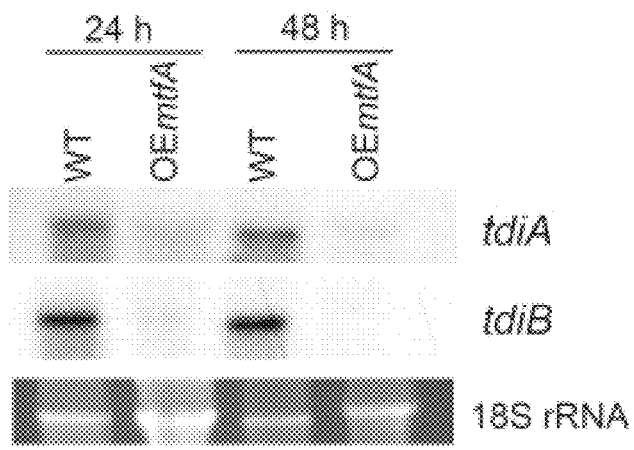
Figure 20C:
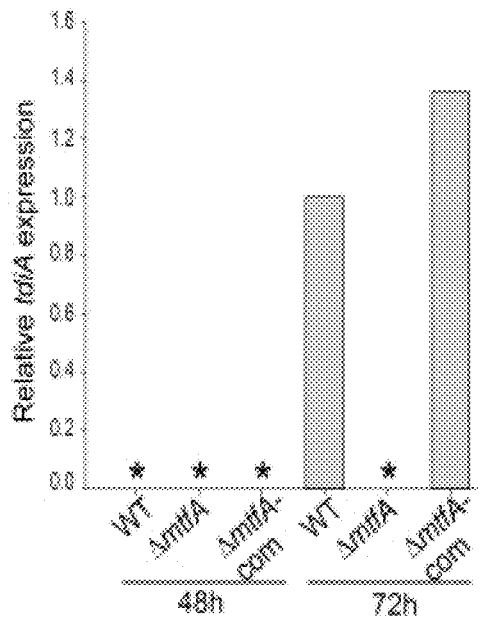
Figure 20D:
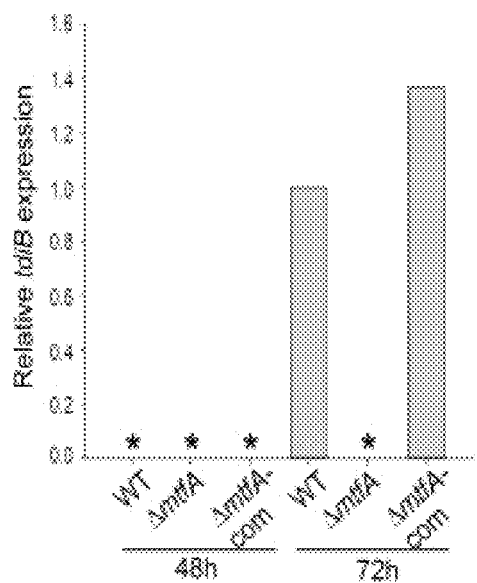
Figure 20E:
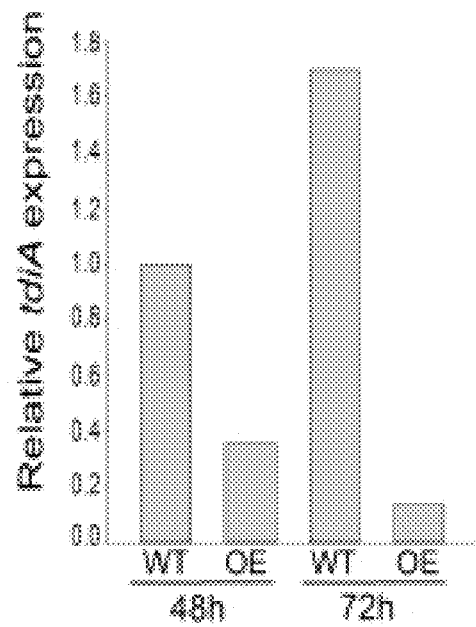
Figure 20F:
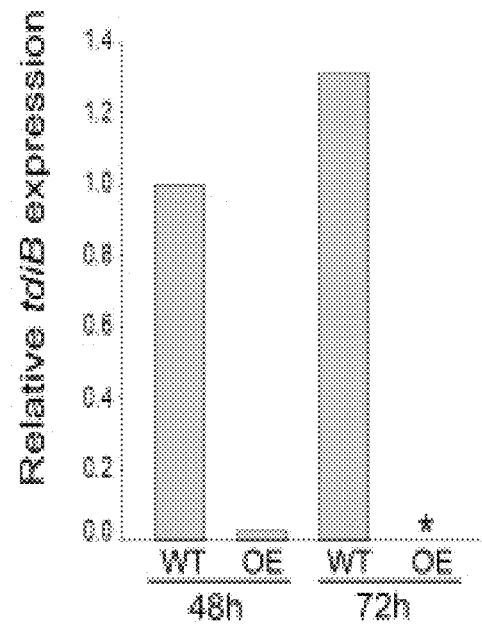

Whether mtfA controls the expression of genes involved in terrequinone biosynthesis, a compound known for its anti-tumoral properties was tested. Specifically the expression of tdiA and tdiB was examined. At 24 h and 48 h of incubation, expression of tdiA and tdiB was detected in the wild-type control and complementation strains, while transcripts of these genes were absent in the mtfA deletion mutant (FIG. 20(A)). Similarly to the case of ST production, over-expression of mtfA negatively affected the expression of tdiA and tdiB (FIG. 20(B)); Although transcripts were detected for both genes in the mtfA overexpression strain, tdiA expression levels were drastically reduced compared with the control at both 24 and 48 hours after induction, and tdiB expression was only detected at 24 h in the overexpression mtfA at very low levels, while it was clearly detectable in the control strain at both time points analyzed.

MtfA Subcellular Localization

Figure 21:
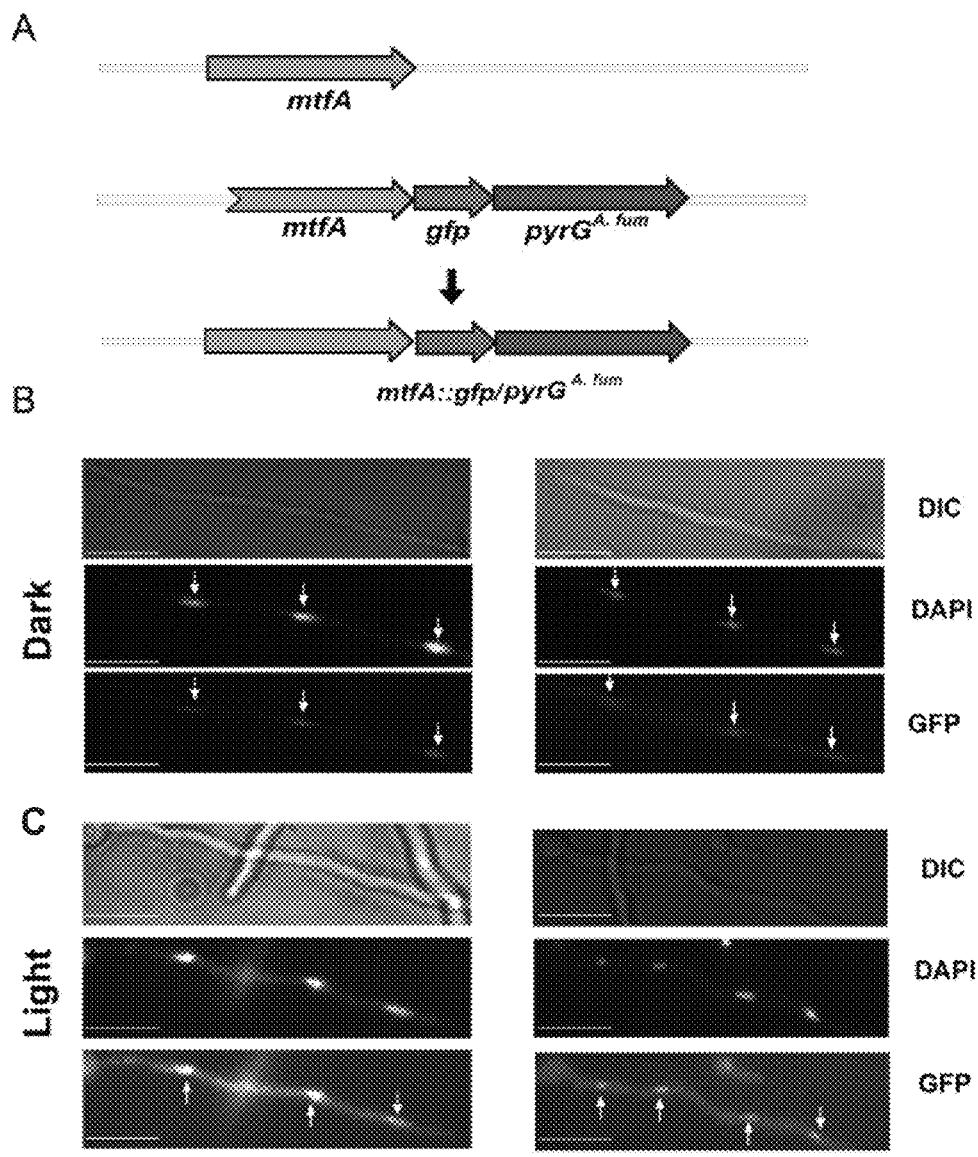
FIG. 21 mftA localizes in nuclei. A) Diagram of the strategy utilized to fuse GFP to mtfA. The tagged construct was introduced at the mtfA locus by a double-over event. B) Micrographs showing the subcellular localization of the mtfA::GFP in *A. nidulans* growing in the light or in the dark. Scale bar represent 20 micrometers.
Figure 22:
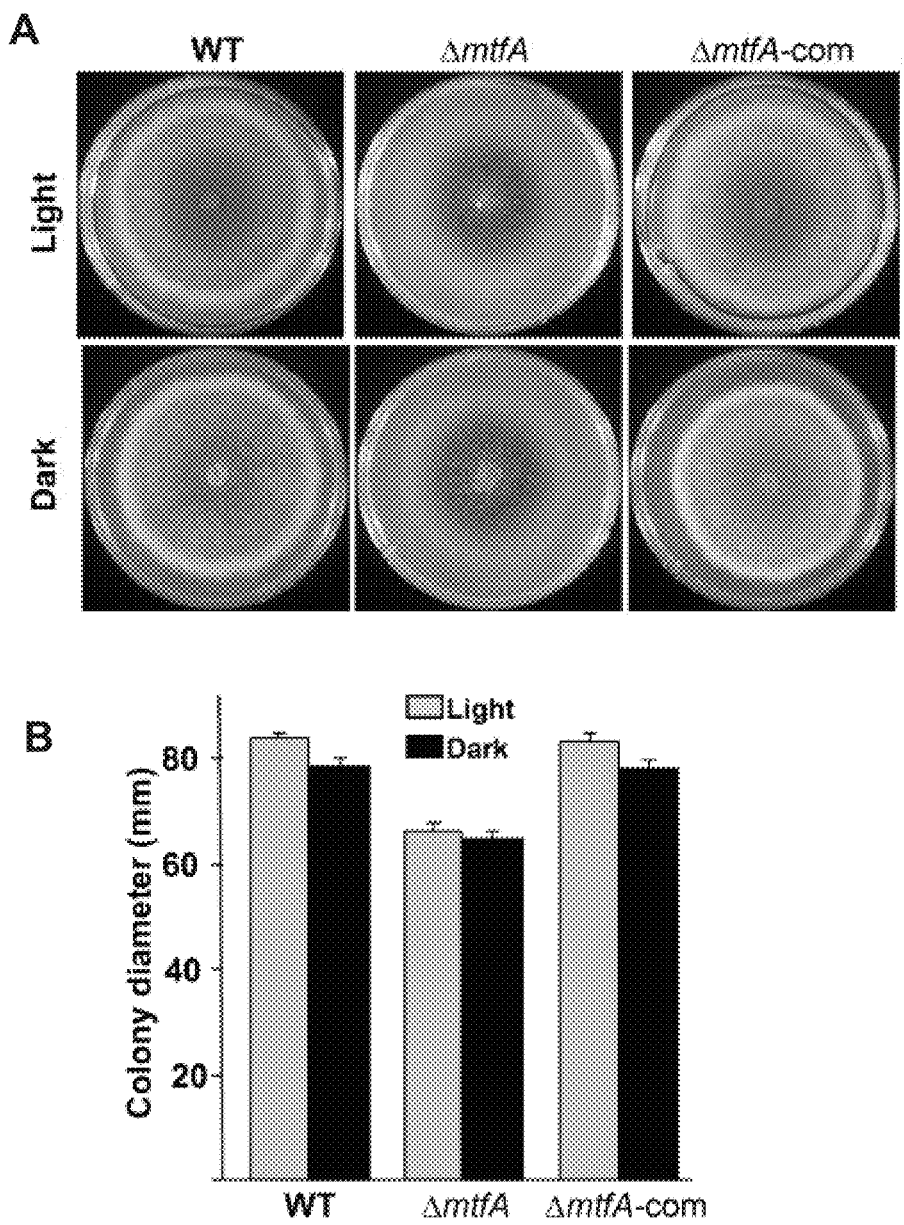
FIG. 22 Deletion of mtfA affects fungal growth and colony pigmentation. (A) Wild type (WT) veA+(TRV50.2), ΔmtfA (TRVp ΔmtfA) and ΔmtfA–com complementation (TRV ΔmtfA–com) were point-inoculated on GMM plates and incubated at 37° C. in either dark or light for 6 days. (B) Fungal growth was measured as colony diameter. Values are means of four replicates. Standard error is shown.

The function of the *A. nidulans* mtfA gene product was studied by examining its subcellular localization in both light and dark conditions. Because the predicted MtfA has a $C_2H_2$ DNA binding domain it could be found in nuclei. A strain containing MtfA fused to GFP was generated. Observations using fluorescence microscopy indicated that indeed MftA localizes in nuclei, as revealed when compared with DAPI staining. Nuclear localization of MtfA was independent of the presence or absence of light (FIG. 21).

mtfA Regulates Asexual and Sexual Development in *A. nidulans*

Figure 15:
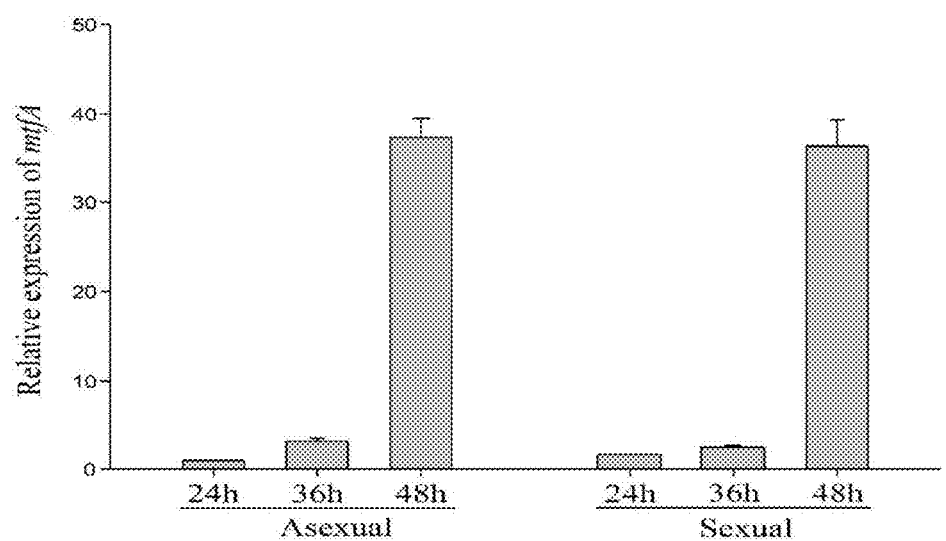
FIG. 15 Expression of mtfA in the wild-type strain. qRT-PCR analysis showing mtfA expression in the wild-type strain (TRV50.2) at the times indicated under conditions promoting asexual (light) or sexual development (dark). The strains were topagar inoculated on GMM and incubated at 37° C.
Figure 16:
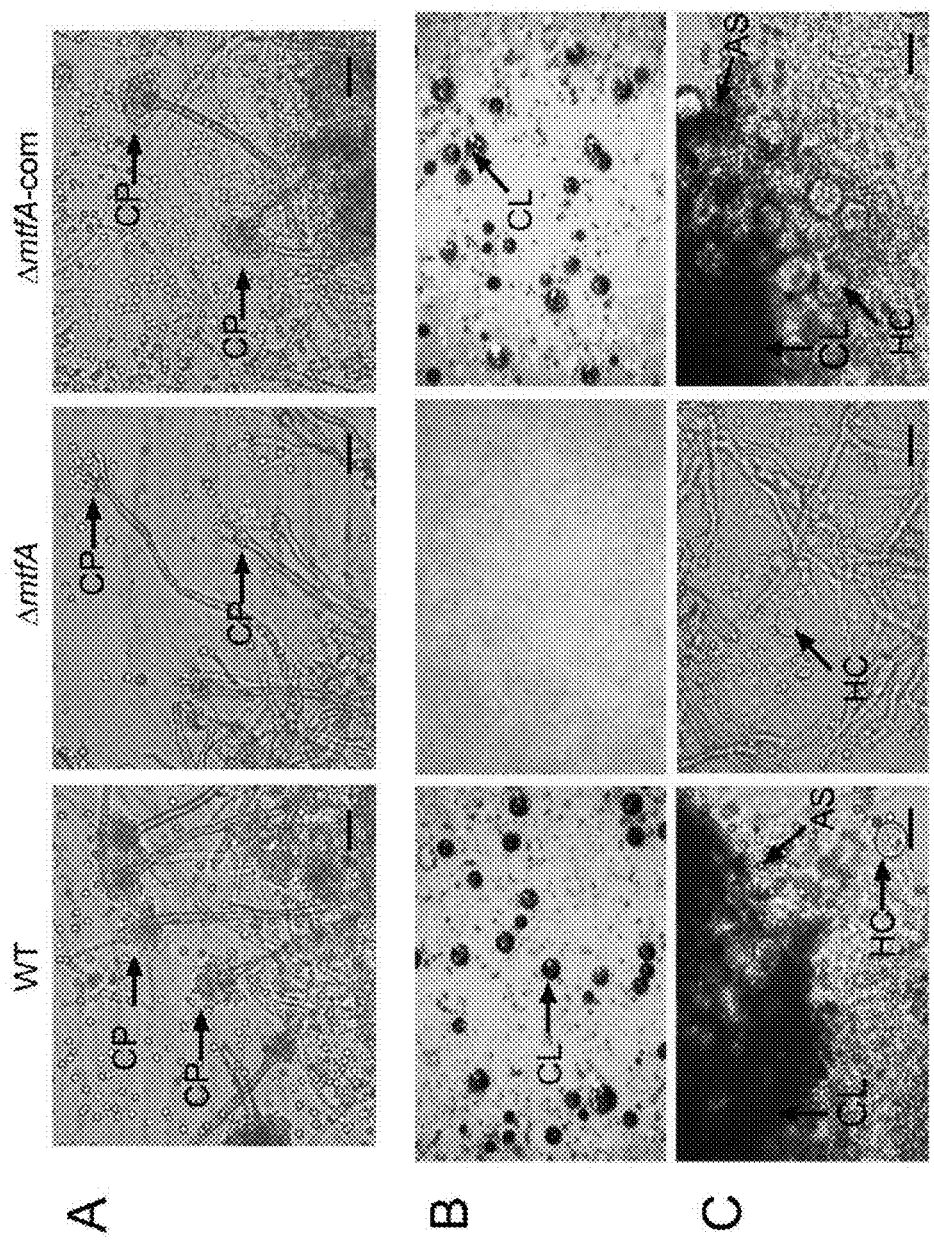
FIG. 16 Micrographs of asexual and sexual structures. (A) Conidiophores forming in wild type (WT) veA+(TRV50.2), ΔmtfA (TRVpΔmtfA) and ΔmtfA–com complementation (TRVΔmtfA–com) strains in top agar-inoculated solid GMM cultures incubated for 5 days in the light at 37° C. Bar represent 20 micrometers. CP, conidiophores. (B) Micrographs showing the presence of cleistothecia (CL) in wild type (WT) veA+(TRV50.2), and ΔmtfA–com complementation (TRVΔmtfA–com) cultures growing in the dark for 5 days. Magnification 50×. (C) Micrographs showing details of sexual structures. Bar represents 15 micrometers. CL, portion of an open cleistothecium; AS, ascospores; HC, Mille cells.
Figure 17:
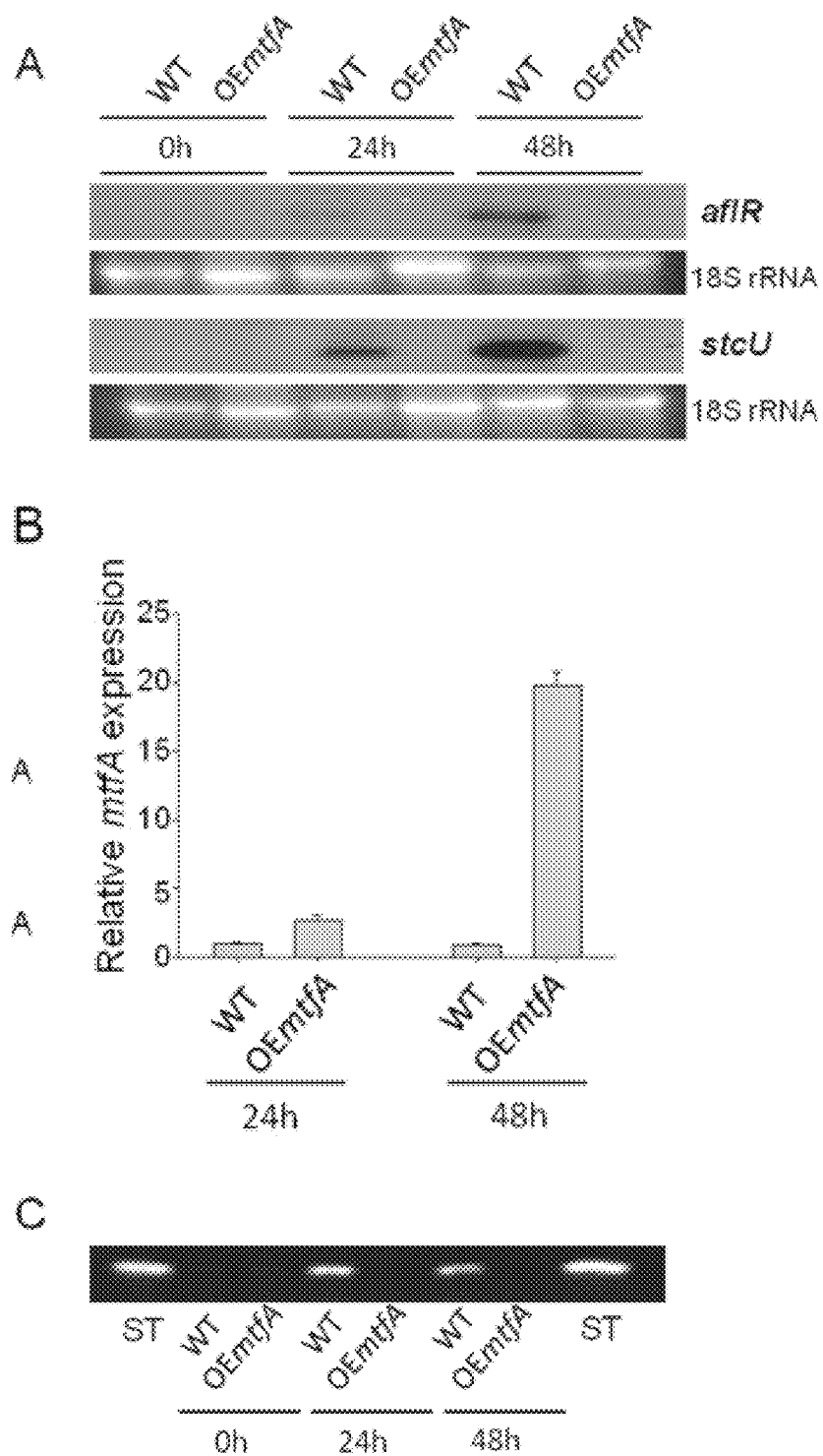
FIG. 17 Over-expression of mtfA suppresses aflR and stcU expression and ST production. (A) Northern blot analysis of OR and stcU expression. Wild-type isogenic control (WT) veA+(TRV50.1) and over-expression (OE) mtfA strain (TRV60) were inoculated in GMM liquid medium ($10^6$ conidia $mL^{-1}$) and grown for 16 hours in a shaker incubator at 37° C. and 250 rpm. Then, equal amounts of mycelium were transferred and spread onto TMM agar medium. The cultures were further grown for 48 hours and 72 hours. Mycelial samples were collected at 0 hour (shift time), and 24 and 48 hours of incubation after shifto onto TMM. 18S rRNA serves as loading control. (B) qRT-PCR expression analysis of mftA from mycelial samples collected after 24 hours and 48 hours of incubation after transfer onto TMM agar medium. (C) TLC analysis of ST production from cultures described in (A-B).
Figure 18A:
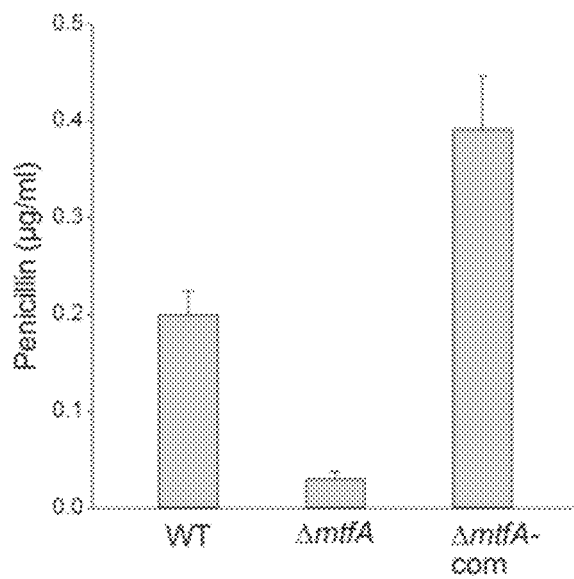
FIG. 18 Deletion of mtfA results in a reduction of penicillin biosynthesis. (A) Extracts from wild-type (WT) veA+ control (TRV50.2), ΔmtfA (TRVpΔmftA) and ΔmtfA–com complementation strain (TRVΔmtfA–com) were analyzed for penicillin content as described in Materials and Methods, (B), D), (E)) qRT-PCR expression analysis of acvA, ipnA and aatA from mycelial samples collected after 24 hours and 48 hours of incubation in PN inducing medium. (C) Northern blot analysis of ipnA and aatA from samples collected after 24 hours and 48 hours of incubation in PN inducing medium. Densitometries were carried out with the Scion Image Beta 4.03 software.
Figure 18B:
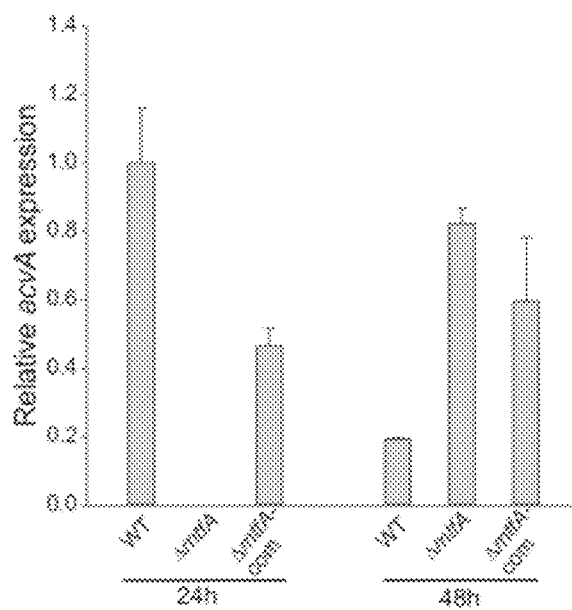
Figure 18C:
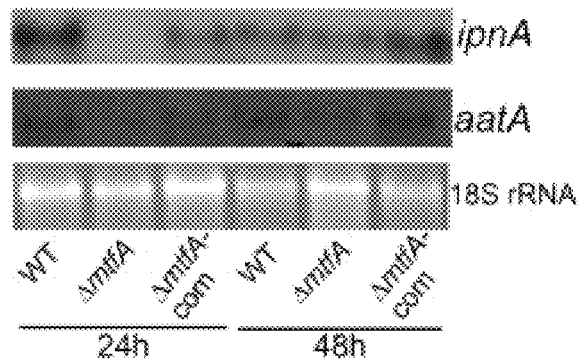
Figure 18D:
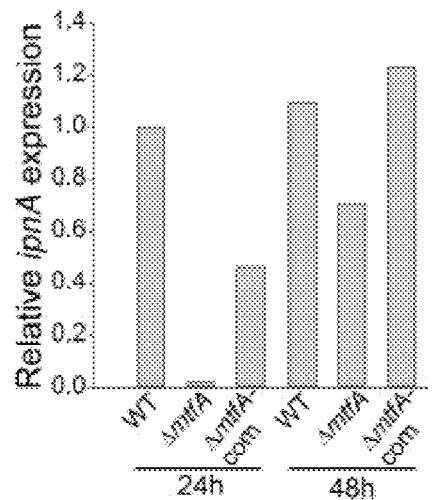
Figure 18E:
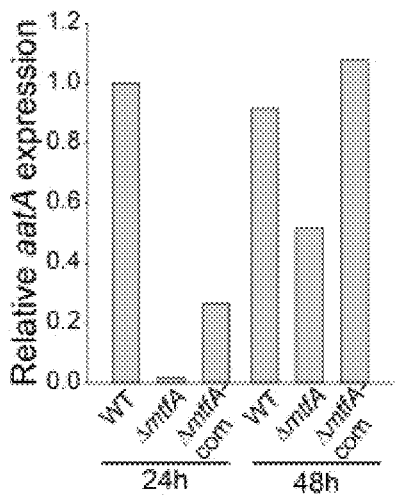
Figure 23A:
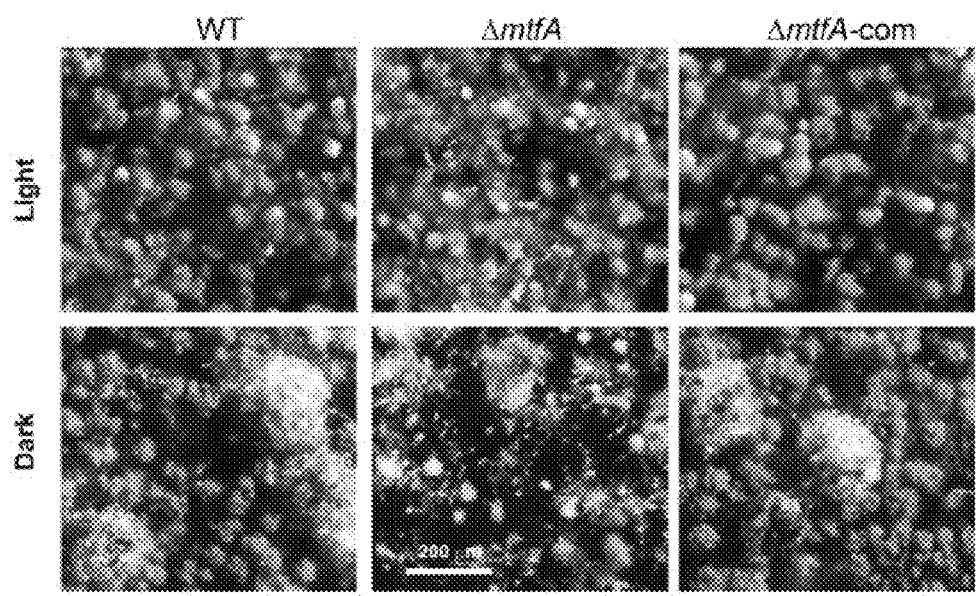
FIG. 23 Deletion of mftA mutant negatively affects conidiation and sexual development. (A) Micrographs of point-inoculated cultures of wild type (WT) veA+(TRV50.2), ΔmtfA (TRVpΔmtfA) and ΔmtfA–com complementation (ΔmtfA–com) strains grown in the light or in the dark for 6 days. Microscopy samples were collected 2 cm from the point of inoculation. Images were captured using upright Leica MZ7S stereomicroscope, (B) Quantitative analysis of conidial production. Strains were top-agar inoculated ($10^6$ conidia mL$^{-1}$) and grown for 48 hours and 72 hours on GMM. (C) qRT-PCR quantification of brlA expression from the cultures described in (B). (D) Quantitative analysis of Hülle cell production after 48 hours and 72 hours of incubation. (E) Quantitative analysis of cleistothecial production after 10 days of incubation. Cleistothecia were counted after spraying the cultures with 70% ethanol to improve visualization. Core diameter was 16 m. Asterisks in (D) and (E) indicate not detected. Values are means of three replicates Error bar indicates standard errors.
Figure 23:
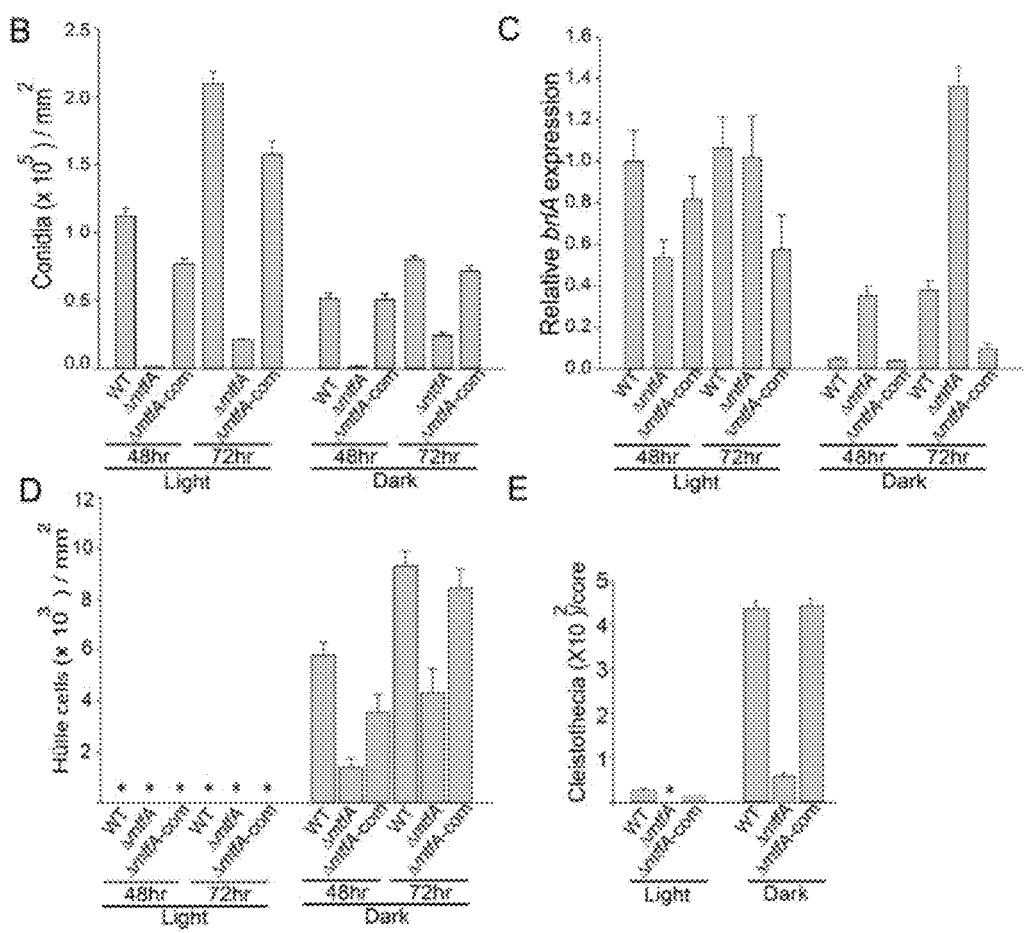

Deletion of mtfA results in slightly smaller colonies than the wild-type (FIG. 9), indicating that mtfA positively influences fungal growth in both light and dark conditions. The mtfA deletion colonies presented a brownish pigmentation which is absent in the control strain. mtfA was expressed at similar levels under conditions promoting either asexual or sexual development, increasing transcript accumulation over time (FIG. 15), Conidiophore formation and conidial production was drastically reduced in the mtfA deletion strains with respect to the wild type (FIG. 23). This effect was observed in both light and dark cultures. The differences in conidiation levels were more pronounced in the light, a condition that promotes asexual development in *A. nidulans*. In addition, the conidiophores produced by the ΔmtfA strain presented fewer metula and phialides than the control strains (FIG. 16(A)). The reduction in conidiation observed in ΔmtfA coincided with alterations in the expression of brlA (FIG. 23(C)), a key transcription factor in the initiation of conidiophore formation. Reduction in brlA expression was observed after 48 h of incubation in the light, condition that promotes conidiophore formation. In the dark brlA levels in the wild type were low, as expected. However, expression of this gene in the mtfA mutant was abnormally high in the dark, a condition that represses conidiation. The increase of brlA expression in ΔmtfA in the dark not only did not result in hyperconidiation, but the conidial production was as low as that observed in ΔmtfA growing in the light.

Sexual development is also influenced by mtfA. Absence of mtfA in *A. nidulans* results in a more than 2-fold reduction in Hülle cells, nursing cells participating in the formation of cleistothecia (fruiting bodies) (FIG. 23(D)). Cleistothecial production was delayed and decreased in this mutant (FIGS. 23(A), (E) and FIGS. 16(B), (C)). The cleistothecia present in ΔmtfA were of reduced size. Expression of nsdD and steA, encoding transcription factors necessary for the activation of sexual development in *A. nidulans* did not significantly change in the absence of mtfA under the experimental conditions assayed. Complementation of the deletion mutant with the mtfA wild-type allele restored wild-type morphogenesis.

Materials and Methods

Novel veA-Dependent Genetic Elements

To identify novel veA-dependent genetic elements involved in the regulation of ST biosynthesis in the model system *A. nidulans*, a mutagenesis in a deletion veA strain to was performed to obtain revertant mutant that regain the capacity to produce toxin. Several revertant mutants (RM) were obtained. In the present study one of the selected revertants, RM7 is disclosed. This revertant presented a point mutation in a gene that we denominated mtfA (master transcription factor) encoding a novel putative $C_2H_2$ zinc finger domain type transcription factor. The mtfA effect on ST production is veA-dependent. Additionally, mtfA regulates the production of other secondary metabolites, such as penicillin and terraquinone. Furthermore, mtfA is also important for sexual and asexual development in *A. nidulans*.

A. *Aspergillus nidulans* mtfA coding region was fused to the alcA(p) promoter and introduced into *Aspergillus nidulans* cells. Cells were grown in penicillin inducing medium were antibiotic levels increased approximately 25% to 5-fold.

B. *Aspergillus nidulans* mtfA coding region was fused to the alcA(p) promoter and introduced into *Aspergillus nidulans* cells. Cells were grown under conditions that allow the production of the mycotoxin sterigmatocystin, an aflatoxin-related mycotoxin. Induction of the overexpression promoter under these conditions C. Deletion of the mtfA coding region results in elimination or reduction of the mycotoxin sterigmatocystin even under conditions that induce toxin production.

Improved yield in penicillin G production has been already achieved by overexpression of mtfA. Over-expression can be also be achieved by using other strong promoters (contitutive or inducible) or by introducing multicopies of all or parts of the mtfA gene in cells.

Fungal Strains and Growth Conditions

Fungal strains used in this study are listed in Table 1. Media used include complete media YGT (0.5% yeast extract, 2% dextrose, trace elements), glucose minimal media (GMM) (1% dextrose, nitrate salts, trace elements pH-6.5) and oat meal media (OMM) (1% oat meal). Nitrate salts, trace elements and vitamins were as described previously (KAFER 1977). Uridine and uracil, amino acids and vitamins were added when necessary to supplement the auxotrophic markers. Uracil and uridine were added to YGT media for pyrG auxotroph. Glucose was replaced with threonine in threonine minimal medium (TMM) for induction of alcA promoter.

Genetic Techniques

Crosses between strains were followed as described (PONTECORVO et al. 1953.). Crossing between RAV-pyrol and RM7 was made and progenies were analyzed for the presence/absence of veA and suppressor mutation based on production of NOR and colony morphology and finally confirmed by PCR. The cross resulted in progenies that falls in four groups based on phenotype such as 1. RM7 Parental type (strongly defective in conidiation, positive for NOR production); 2. RAV-pyrol parental type (normal condiation, positive for NOR production); 3. Recombinant type RM7-R1 (ΔveA and ΔstcE) (appeared as that of RDAE 206 strain. i.e. slightly defective in conidiation and negative for NOR production) and recombinant type RM7-R2 (moderately defective in conidiation and positive for NOR production).

Identification of Mutated Gene in the RM7 Mutant

To find mutated gene in RM7 mutant, it should be complemented with genomic library and positive complemented strain should not produce NOR as that of parental RDAE206 in which mutagenesis was carried out.

RM7-R2 (sup−) producing a brownish-pink pigmentation and moderated defect in conidiation was used for complementation with the *Aspergillus nidulans* genomic library. Positive transformants that restored wild-type phenotype were selected. Genomic DNA was prepared from these transformants; plasmid DNA was rescued by transforming *E. coli* cells with total genomic DNA. For each gene, 5-10 ampicillin-resistant colonies were picked and the plasmid DNA was extracted and analyzed by restriction digestion and PCR as described previously (OSHEROV and MAY 2000). Finally, both the ends of insert DNA fragments of the isolated plasmid were sequenced and the total genomic sequences present in the plasmid DNA were acquired from the *A. nidulans* genome database at broad Institute webpage (http://www.broadinstitute.org/annotation/genome/*aspergillus*_group/MultiHome.html) by BLAST analysis. The exact location of the mutation in RM7 mutants is identified by PCR amplifying and sequencing the corresponding genomic region.

Fungal Transformation and Genetic Manipulation

Polyethylene glycol-mediated transformation of protoplasts was carried out as described earlier (MILLER et al. 1985; YELTON et al. 1983). DNA and RNA isolation, gel electrophoresis, standard molecular manipulations, and Southern and Northern blot analysis were performed as described previously (MILLER et al. 1987; MILLER et al. 1985; SAMBROOK and RUSSELL 2003; VALLIM et al. 2000).

Creation of the mtfA Deletion Mutant by Gene Replacement and Generation of the Complementation Strain The entire coding region of mtfA gene (locus AN8741.2) was replaced in RDAE206 and RJMP1.49 strains using the gene deletion cassette obtained from FGSC (http://www.fgsc.net). The deletion cassette was transformed into protoplasts of RDAE206 and RJMP1.49 strains and transformants were selected on appropriate selection medium and finally confirmed by Southern blot analysis. The deletion strains were designated as RDAEΔmtfA and ΔmtfA respectively.

To complement ΔmtfA, the entire mtfA gene with upstream and downstream fragment was amplified with RM7com1 and RM7com2 primer pair, digested with SacII and KpnI and cloned into pSM3 vector as pSM3-rm7com. The complementation vector, pSM3-rm7com was transformed into ΔmtfA strain and transformants selected on appropriate selection medium and complementation was confirmed by PCR and Southern blot analysis. The complemented stain is designated as ΔmtfA-corn.

Strains isogenic with respect to the auxotrophic markers were generated and used in this study, differing only in the presence or absence of mtfA.

Overexpression of mtfA

To over express the mtfA gene, the entire gene of mtfA was amplified starting from start codon to stop codon with RM7-OE1 and RM7-OE2 primer pair, digested with kpnI and PacI and cloned into pmacro having alcA promoter and trpC terminator as pMacroRm7OE vector. The pMacroRm7OE vector was transformed into RJMP1.49 and transformants were selected on appropriate selection medium and confirmed by Southern blot analysis.

For mtfA over-expression analysis, 400 ml of liquid GMM was inoculated with spore suspension to the final concentration of $10^6$ conidia/ml and incubated for 16 hrs at 37° C. and 250 rpm. The mycelium was collected, washed with double distilled water and squeezed in between paper towel. Equal amount of mycelium was then inoculated on the induction medium, threonine minimal medium. The mycelium was collected at 24 and 48 hours after shift to the induction medium and ST and RNA analysis for aflR and stcU were carried out.

The strains used were isogenic with respect to the auxotrophic markers differing only in the modifications at the mtfA locus.

Toxin Analysis

Plates containing 25 ml of solid GMM or OMM with appropriate supplements were inoculated with five milli liter of top agar with spore suspension containing $10^6$ spores/ml. The cultures were incubated in dark. Three cores (16 mm diameter) from each replicate plate were collected in a 50 ml Falcon tube. Alternatively, strains were grown in GMM liquid shaken cultures (inoculum $10^6$ conidia ml$^{-1}$) and incubated at 37° C., Twenty-four h and 48 h old culture supernatants were analyzed for ST. NOR and ST was also analyzed in TMM overexpression mtfA and control cultures NOR or ST were extracted with CHCl$_3$. The extracts were dried overnight and then resuspended in 200 µl of CHCl$_3$. Two micro litre of ST/NOR standard and 25 µl of the samples were fractionated in the silica gel thin-layer chromatography (TLC) plate using benzene and glacial acetic acid [95:5 (v/v)] as a solvent system for ST analysis and chloroform:acetone:n-hexane (85: 15:20) as a solvent system for NOR. The plates were then sprayed with aluminum chloride (15% in ethanol) and baked for 10 min at 80° C. ST/NOR bands on TLC plates were viewed by exposing the plates under UV light (375-nm).

Morphological Studies

Asexual and sexual developmental studies were performed in *A. nidulans* strains TRV50, ΔmtfA, ΔmtfA-COM (Table 1). Plates containing 25 ml of solid GMM with the appropriate supplements were spread-inoculated with 5 ml of top agar containing $10^6$ spores/ml. The cultures were incubated at 37° C. in dark or in light conditions. A 7-mm-diameter core was removed from each spread plate culture and homogenized in water to release the spores. Conidia were counted using a hemacytometer. Identical cores were taken to examine cleistothecial production under a dissecting microscope. To increase visualization of cleistothecia, the cores were sprayed with 70% ethanol to remove conidiophores.

For radial growth analysis, approximately 500 conidia of each strain were point inoculated and incubated for 6 days under light and dark conditions. The radial growth was measured after six days of incubation. Experiments were performed triplicate, and the mean and standard error were calculated.

Penicillin Analysis

The PN bioassay was performed as previously described (Brakhage et al., 1992) with some modifications, using *Bacillus. calidolactis* C953 as the test organism. Briefly, strains were inoculated with approximately $10^6$ spores ml$^{-1}$ in 25 ml of seed culture medium, and incubated at 26° C. for 24 h at 250 rpm. Mycelia were then transferred to PN-inducing medium (Brakhage et al., 1992). The experiment was carried out with three replicates. After 96 h, the cultures were filtered using Miracloth (Calbiochem, USA) and the supernatants were collected for analysis. Three hundred millilitres of Tryptone-Soy Agar was supplemented with 20 ml of *B. calidolactis* C953 culture and plated on three 150-mm-diameter Petri dishes. One hundred microlitres of each culture supernatant was added to 7-mm-diameter wells. Bacteria were allowed to grow at 55° C. for 16 h and inhibition halos were visualized and measured. To confirm that the observed antibacterial activity was due to the presence of PN and not to the presence of different fungal compounds in the supernatant, additional controls containing commercial penicillinase from *Bacillus cereus* (Sigma, Mo., USA) were used. A standard curve using various concentrations of PN G (Sigma, Mo., USA) was used to determine PN concentration in the samples.

Gene Expression Analysis

Total RNA was extracted from lyophilized mycelial samples using RNeasy Mini Kit (Qiagen) or Triazol (Invitogen), following the manufacturer's instructions. Northern blots were used to evaluate gene expression levels of aflR, stcU, tdiA and tdiB. For making probe for northern blots were aflR, a 1.3-kb EcoRV-XhoI fragment of pAHK25 (Brown et al., 1996); stcU, a 0.75-kb SstII-SmaI fragment of pRB7 (Yu et al., 1996).

Conservation of MtfA Homologs from Different Fungal Specie

When comparing with other fungal species, the deduced amino acids of the homologs from different fungal species are used. FIG. 24 and Table 2 show a high degree of conservation between MtfA homologs from different fungal species, including species that produce penicillin (*Penicillium chrysogenum*) or other important secondary metabolites such as lovastatin (*Aspergillus terreus*) at industrial levels, among others.

TABLE 1

Study of mMtfA subcellular localization: mtfA was tagged with GFP

| Sl. No | Strain name | Genotype | Description | Reference |
|---|---|---|---|---|
| 1 | FGSC4 | Wild-type | Wild-type control | FGSC |
| 2 | RDAE206 | yA1, pabA1, pyrG89, argB2, ΔstcE::argB, ΔveA ::argB | Mutagenesis study | |
| 3 | RAV1 | wA1, yA2, pabA1, pyrG89, argB2, ΔstcE::argB, veA1 | Positive NOR producer | |
| 4 | RAV-pyrol | wA1, yA2, pyroA4, argB2, ΔstcE::argB, veA1 | To cross with RM7 to find out mutation pattern in RM7 mutants | Ramamoorthy et al., 2011 |
| 5 | RAV-pyrol | wA1, yA2, pyroA4, argB2, ΔstcE::argB, ΔstcE::argB | To cross with RM7 to find out mutation pattern in RM7 mutants | Ramamoorthy et al., 2011 |

TABLE 1-continued

Study of mMtfA subcellular localization: mtfA was tagged with GFP

| Sl. No | Strain name | Genotype | Description | Reference |
|---|---|---|---|---|
| 6 | RM7 | yA2, pabA1, pyrG89, argB2, ΔstcE::argB, ΔveA::argB, mtfA⁻⁻ | mutants | Ramamoorthy et al., 2011 |
| 7 | RM7-R2 | wA1, yA2, pyrG89, argB2, ΔstcE::argB, mtfA⁻⁻, veA1 | For transformation and identification of mutation in the genome | Present |
| 8 | RM7-R2-com | wA1, yA2, pyrG89, argB2, ΔstcE::argB, mtfA⁻⁻ pRG3-AMA-NOT1-mtfA::pyr4, veA1 | Complementation of RM7-R2 with wild-type mtfA | Present |
| 9 | RJMP1.49 | pyroA4, pyrG89 argB2, delnku::argB, veA+ | For generation of mtfA gene replacement | Present |
| 10 | TRV50 | pyroA4, pyrG89, pyrG+, argB2, delnku::argB, veA+ | Wild-type control strain | Present |
| 11 | TRVΔmtfA | pyroA4, pyrG89, ΔmtfA::AfpyrG, argB2, delnku::argB, veA+ | To study mtfA functionality | Present |
| 12 | TRVΔmtfA-com | pyroA4, pyrG89, ΔmtfA::AfpyrG, argB2, delnku::argB, veA+ mtfA::pyroA | Complementation strain of TRVΔmtfA | Present |
| 13 | mtfAOE | pyroA4, pyrG89, alcA::mtfA::pyr4, argB2, Δnku::argB veA+ | To over-express mtfA | Present |
| 14 | TRV-Stag | pyroA4, pyrG89 mtfA::stag::afpyrG, argB2, delnku::argB, veA+ | To study interacting proteins by pull down experiments | Present |
| 15 | TNO2A7 | pyroA4, riboB2, pyrG89, argB2, nkuA::argB veA1 | | Present |
| 16 | | | | |

TABLE 2

Amino acid sequence comparison of MtfA in *Aspergillus nidulans* with other fungal species. The comparisons were done using the BLASTp tool provided by NCBI (National Center for Biotechnology Information) and EMBOSS Needle - Pairwise Sequence Alignment tool provided by EMBL-EBI (European Bioinformatics Institute).

| | NCBI | | EMBOSS Needle - Pairwise Sequence Alignment (global alignment) | | |
|---|---|---|---|---|---|
| Name of the species, with the strain information | Accession number | E-value (Blastp) | Length | % Identity | % Similarity |
| *Aspergillus oryzae* [RIB40] | XP_001823905.1 | 0 | 332 | 64.2 | 70.8 |
| *Aspergillus clavatus* [NRRL 1] | XP_001270264.1 | 2E-111 | 347 | 65.1 | 71.2 |
| *Aspergillus niger* [CBS 513.88] | XP_001395874.1 | 5E-106 | 336 | 62.8 | 71.1 |
| *Aspergillus kawachii* [IFO 4308] | GAA87693.1 | 6E-106 | 336 | 62.8 | 70.8 |
| *Aspergillus fumigatus* [Af293] | XP_747808.1 | 2E-100 | 342 | 62 | 71.3 |
| *Neosartorya fischeri* [NRRL 181] | XP_001257459.1 | 5E-94 | 353 | 60.9 | 68.8 |
| *Aspergillus flavus* [NRRL3357] | XP_002380969.1 | 9E-94 | 332 | 64.2 | 70.8 |
| *Aspergillus terreus* [NIH2624] | XP_001209872.1 | 6E-93 | 344 | 62.5 | 68.9 |
| *Penicillium chrysogenum* [Wisconsin 54-1255] | XP_002566301.1 | 3E-74 | 351 | 49.3 | 58.7 |
| *Coccidioides immitis* [RS] | XP_001239027.1 | 1E-64 | 355 | 44.5 | 54.6 |
| *Ajellomyces capsulatus* [H88] | EGC49893.1 | 9E-64 | 364 | 45.9 | 58.0 |
| *Uncinocarpus reesii* [1704] | XP_002585289.1 | 6E-54 | 440 | 34.1 | 42.0 |
| *Penicillium marneffei* [ATCC 18224] | XP_002148846.1 | 1E-52 | 342 | 38 | 43.9 |
| *Botryotinia fuckeliana* | CCD44702.1 | 6E-47 | 347 | 40.3 | 51.9 |
| *Neurospora tetrasperma* [FGSC 2508] | EGO52630.1 | 2E-44 | 347 | 39.8 | 50.1 |
| *Neurospora crassa* [OR74A] | XP_964590.1 | 2E-44 | 343 | 39.1 | 50.1 |
| *Magnaporthe oryzae* [70-15] | XP_003720663 | 4E-50 | 335 | 38.5% | 50.4% |
| *Chaetomium globosum* [CBS 148.51] | XP_001222401.1 | 6E-39 | 382 | 34.0 | 45.8 |
| *Fusarium oxysporum* [Fo5176] | EGU84033.1 | 3E-38 | 350 | 34.9 | 43.4 |

TABLE 3A

| | Species | Accession | NCE Forward Blast % Value | @Identity | Length |
|---|---|---|---|---|---|
| 1 | *Aspergillus oryzae* [RIB40] | XP 001823905.0 | 0.00E+00 | 64% | 319 |
| 2 | *Aspergillus clavatus* [NRRL 1] | XP 001270264.1 | 2.00E-111 | 64% | 335 |
| 3 | *Aspergillus niger* [CBS 513.88] | XP 001395587.1 | 5.00E-106 | 62% | 325 |
| 4 | *Aspergillus kawachii* [IFO 4308] | GAA87693.1 | 6.00E-106 | 62% | 325 |
| 5 | *Aspergillus fumigatus* [Af293] | XP_747808.1 | 2.00E-100 | 59% | 336 |
| 6 | *Neosartorya fischeri* [NRLL 181] | XP_001257459.1 | 5.00E-94 | 59% | 334 |
| 7 | *Aspergillus flavus* [NRRL3357] | XP_002380969.1 | 9.00E-94 | 64% | 319 |
| 8 | *Aspergillus terreus* [NIH2624] | XP_001209872.1 | 6.00E-93 | 61% | 319 |
| 9 | *Penicillin chrysogenum* [Wisconsin 54-1255] | XP_002566301.1 | 3.00E-74 | 48% | 301 |
| 10 | *Coccidiodes Immitis* [RS] | XP_001239027.1 | 1.00E-64 | 49% | 336 |
| 11 | *Ajellomyces capsulatus* [H88] | EGC49893.1 | 9.00E-64 | 50% | 345 |
| 12 | *Uncinocarpus reesii* [1704] | XP 002585289.1 | 6.00E-54 | 47% | 423 |
| 13 | *Penicillin maneffei* [ATCC 18224] | XP 002148846.1 | 1.00E-52 | 53% | 247 |
| 14 | *Botryotinia Fuckeliana* | CCD44702.1 | 6.00E-47 | 42% | 317 |
| 15 | *Neurospara tetrasperma* [FGSC 2508] | EGO52630.1 | 2.00E-44 | 43% | 305 |
| 16 | *Neurospara crassa* [OR74A] | XP_964590.1 | 2.00E-44 | 45% | 305 |
| 17 | *Magnaporthe oryzae* [70-15] | XP_003720663 | 4.00E-50 | 43% | 309 |
| 18 | *Chaetomium globosum* [CBS 148.51] | XP_001222401.1 | 6.00E-39 | 38% | 342 |
| 19 | *Fusarium oxysporum* [Fo 5176] | EGU84033.1 | 3.00E-38 | 42% | 276 |

TABLE 3B

| | Species | EMBOSS Needle Alignment (Global alignment) | | | | | |
|---|---|---|---|---|---|---|---|
| | | Length | % Identity | % Similarity | Phylum | Class | Genus |
| 1 | *Aspergillus oryzae* [RIB40] | 332 | 64.20% | 70.80% | Ascomycota | Eurotiomycetes | *Aspergillus* |
| 2 | *Aspergillus clavatus* [NRRL 1] | 347 | 65.10% | 71.20% | Ascomycota | Eurotiomycetes | *Aspergillus* |
| 3 | *Aspergillus niger* [CBS 513.88] | 336 | 62.80% | 71.10% | Ascomycota | Eurotiomycetes | *Aspergillus* |
| 4 | *Aspergillus kawachii* [IFO 4308] | 336 | 62.80% | 70.80% | Ascomycota | Eurotiomycetes | *Aspergillus* |
| 5 | *Aspergillus fumigatus* [Af293] | 342 | 62.00% | 71.30% | Ascomycota | Eurotiomycetes | *Aspergillus* |
| 6 | *Neosartorya fischeri* [NRLL 181] | 353 | 60.90% | 68.80% | Ascomycota | Eurotiomycetes | *Neasartarya* |
| 7 | *Aspergillus flavus* [NRRL3357] | 332 | 64.20% | 70.80% | Ascomycota | Eurotiomycetes | *Aspergillus* |
| 8 | *Aspergillus terreus* [NIH2624] | 344 | 62.50% | 68.90% | Ascomycota | Eurotiomycetes | *Aspergillus* |
| 9 | *Penicillin chrysogenum* [Wisconsin 54-1255] | 351 | 49.30% | 58.70% | Ascomycota | Eurotiomycetes | *Penicillin* |
| 10 | *Coccidiodes Immitis* [RS] | 355 | 44.50% | 54.60% | Ascomycota | Eurotiomycetes | *Coccidioides* |
| 11 | *Ajellomyces capsulatus* [H88] | 364 | 45.90% | 58.00% | Ascomycota | Eurotiomycetes | *Ajellomyces* |
| 12 | *Uncinocarpus reesii* [1704] | 440 | 34.10% | 42.00% | Ascomycota | Eurotiomycetes | *Uncinocarpus* |
| 13 | *Penicillin maneffei* [ATCC 18224] | 342 | 38.00% | 43.90% | Ascomycota | Eurotiomycetes | *Penicillin* |
| 14 | *Botryotinia Fuckeliana* | 347 | 40.30% | 51.90% | Ascomycota | Leotiomycetes | *Botryatinla* |
| 15 | *Neurospara tetrasperma* [FGSC 2508] | 347 | 39.80% | 50.10% | Ascomycota | Sordariomycetes | *Neurospara* |
| 16 | *Neurospara crassa* [OR74A] | 343 | 39.10% | 50.10% | Ascomycota | Sordariomycetes | *Neurospara* |
| 17 | *Magnaporthe oryzae* [70-15] | 335 | 38.50% | 50.40% | Ascomycota | Sordariomycetes | *Magnaporthe* |
| 18 | *Chaetomium globosum* [CBS 148.51] | 382 | 34.00% | 45.80% | Ascomycota | Sordariomycetes | *Chaetomium* |
| 19 | *Fusarium oxysporum* [Fo 5176] | 350 | 34.90% | 43.40% | Ascomycota | Sordariomycetes | *Fusarium* |

Gap opening penalty · 10.0
Gap extension penalty · 0.5

TABLE 4

Fungal strains

| Strain name | Pertinent genotype | Source |
|---|---|---|
| FGSC4 | Wild type (veA+) | FGSC |
| RDAE206 | yA2, pabaA1, pyrG89; argB2, ΔstcE::argB, ΔveA::argB | [40] |
| RDAEp206 | yA2, ΔstcE::argB, ΔveA: argB | [40] |
| RAV1 | yA2, pabaA1, pyrG89; wA3; argB2, ΔstcE::argB; veA1 | [40] |
| RAV1p | yA2; wA3; ΔstcE::argB; veA1 | [40] |
| RAV2 | yA2; wA3; argB2, ΔstcE::argB; pyroA4; veA1 | [40] |
| RM7 | yA2, pabaA1, pyrG89; argB2, ΔstcE::argB, ΔveA ::argB, mtfA– | This study |
| RM7p | yA2, ΔstcE::argB, ΔveA ::argB, mtfA– | This study |
| RM7-R2 | yA2; pyrG89; wA3; argB2, ΔstcE::argB, mtfA–, veA1 | This study |
| RM7p-R2 | yA2; wA3; ΔstcE::argB, mtfA– veA1 | This study |
| RM7-R2-com | yA2, pyrG89; wA3; argB2, ΔstcE::argB, mtfA–, pRG3-AMA-NOT1- mtfA::pyr4; veA1 | This study |
| RJMP1.49 | pyrG89; argB2, ΔnkuA::argB; pyroA4; veA+ | [71] |
| TRV50.1 | argB2, ΔnkuA::argB; pyroA4; veA+ | This study |
| TRV50.2 | argB2, ΔnkuA::argB; veA+ | This study |
| TRVΔmtfA | pyrG89; argB2, ΔnkuA::argB; mtfA::pyrG$^{A. fum}$; pyroA4; veA+ | This study |
| TRVpΔmtfA | ΔnkuA::argB; ΔmtfA::pyrG$^{A. fum}$; veA+ | This study |

TABLE 4-continued

Fungal strains

| Strain name | Pertinent genotype | Source |
|---|---|---|
| TRVΔmtfA-com | pyrG89; argB2, ΔnkuA::argB, ΔmtfA::pyrG$^{A.fum}$; pyroA::mtfA; pyroA4; veA+ | This study |
| TRV60 | pyrG89; argB2, ΔnkuA::argB; alcA(p)::mtfA::pyr4; pyroA4; veA+ | This study |
| TDAEΔmtfA | pabaA1, pyrG89; ΔmtfA::pyrG$^{A.fum}$; ΔstcE::argB, ΔveA::argB | This study |
| TDAEpΔmtfA | pyrG89; ΔmtfA::pyrG$^{A.fum}$; ΔstcE::argB, ΔveA::argB | This study |
| RJW41.A | ΔlaeA; veA+ | [36] |
| RDIT2.3 | veA1 | [39] |
| RJW46.4 | ΔlaeA; veA1 | [39] |
| RSD10.1 | pyrG89; wA3; argB2, ΔnkuA::argB; ΔmtfA::pyrG$^{A.fum}$; ΔlaeA::methG; veA1 | This study |
| RSD11.2 | pyrG89; wA3; argB2, ΔnkuA::argB; ΔmtfA::pyrG$^{A.fum}$; ΔlaeA::methG; veA+ | This study |
| TSD12.1 | pyrG89; ΔnkuA::argB; mtfA::gfp::pyrG$^{A.fum}$; pyroA4 | This study |

FGSC Fungal Genetics Stock Center
Doi: 10.1371/journal.pone.0074122.t001

TABLE 5

Primers (SEQ ID NOS 18-53, respectively, in order of appearance)

| Name | Sequence (5' → 3') |
|---|---|
| RM7-F1 | TACGGCGATT CACTCACTTGGGC |
| RM7-R1 | TAACTTACGCATGAGAAGCAGCCG |
| RM7com1 | AAAAAACCGC GGGGATCTGC ACTAGGAGATTG |
| RM7com2 | AAAAAAGGTACCGACCGTGATACCTGATCTTC |
| RM7OE1 | AAAAAAGGTACCATGGATCTCGCCAACCTCATC |
| RM7OE2 | AAAAAATTAATTAATTACACCATCGCGACAGCCC |
| actin-F | ATGGAAGAGGAAGTTGCTGCTCTCGTTATCGACAATGGTTC |
| actin-R | CAATGGAGGGGAAGACGGCACGGG |
| aflR-F | GAGCCCCCAGCGATCAGC |
| aflR-R | CGGGGTTGCTCTCGTGCC |
| stcU-F | TTATCTAAAGGCCCCCCCATCAA |
| stcU-R | ATGTCCTCCTCCCCGATAATTACCGTC |
| rsdD-F | CATCTCACCAGCCACAATTACAGGCGGAACCATCAC |
| rsdD-R | TTGCGAGCCAGACACAGAGGTCATAACAGTGCTTGC |
| steA-F | TCCAGCAAATGGAACCGTGGAATCAGGTGCTC |
| steA-R | GAAGGGATGGGGCAAGAATGAGACTTCTGCGGGTAA |
| brlA-F | AGCTGCCTGGTGACGGTAGTTGTTGTTGGTGTTGC |
| brlA-R | CAGGAACGAATGCCTATGCCCGACTTTCTCTCTGGA |
| acvA_F | GACAAGGACAGACCGTGATGCAGGAGA |
| acvA_R | CCCGACGCAGCCTTAGCGAACAAGAC |
| aatA_F | CCATTGACTTCGCAACTGGCCTCATTCATGGCAAA |
| aatA_R | GCCTTCCGGCCCACATGATCGAAGAC |
| tdiAF | GCCCCAAGTCCATTGTCCTCGTTCAC |
| tdiAR | TCTGCGCCTGCTCGAGAGCAGCATC |
| tdiBF | CATGGACCCTACAGCACTCCITCCT |
| tdiBR | GCGCTCTCAAAGTTCCGCT |
| mtfAgfpF_787 | CCCCACCTCATCTCCAGCATC |

TABLE 5-continued

Primers (SEQ ID NOS 18-53, respectively, in order of appearance)

| Name | Sequence (5' → 3') |
| --- | --- |
| mtfAgfpR_788 | CACCATCGCGACAGCCCT |
| mtfA3'F789 | CCAATTGTGTTACTCCACCTCCTCG |
| mtfA3'R_790 | TTGAGATCGCTTGCGCTCCTAG |
| mtfAlinkerF_791 | AGGGCTGTCGCGATGGTGACCGGTCGCCTCAAACAATGCTCT |
| mtfAlinkerR_792 | CGAGGAGGTGGAGTAACACA ATTGGGTCTGAGAGGAGGCA CTGATGCG |
| aflR06038 | ATGGAGCCCCAGCGATCAGCCAG |
| aflR06039 | TTGGTGATGGTGCTGTCTTTGGCTGCTCAAC |
| mtfA13015 | GCCCTCACCCTCATCGGCAATG |
| mtfA13016 | GGTCGTGGTTCTGCTGGTAGGGTGT |

TABLE 6

Coding region sequences of some mtfA homologs from other fungal species

>ANID_08741 Transcript 1 (*Aspergillus nidulans*)
ATGGATCTCGCCAACCTCATCTCCCAACCGGGGCCTGAGCCTGCTCTGACGGCC
AAATCAAGATACAGCCCTCCTGCCTTTGAACCGGGCTCCTTCTACGCCGCATCT
ACTTCATTCACGCGGACACAAGCGCCACTATCGCCTCCAGTCGAGGATAGATCT
TCTCGCTGCTCACTGCCATCAATCTCTGCGCTTCTTGACAGCGCAGACGGCGCCT
CGACACAAGCTCCAAAGCGCCAACGGCTCAGCTCTCCAATGCACCGTGAACCG
CTTGACAAGAACCCATCTGCCGGCGCTGCTCCCATCCGTCTCCCGCCCACTCCTC
CATTGCGCCCCGGCTCCGGCTTCCACAGCGCCGGCCACTCGCCCTCGAGCTCCA
TCTCATCCATCTCGATGATCAAGTCCGAGTACCCGGCACCACCATCAGCTCCAG
TCTCTCTTCCGGGCCTTCCCAGCCCAACCGACCGCTCGTCCATCTCGAGCCAAG
GGTCTGCGCCGCAGCACCAGCATGGTCCCTACGCCTCGCCAGCTCCCAGCGTGG
CGCCCTCTTACTCCTCGCCCGTTGAGCCCTCACCCTCATCGGCAATGTACTACCA
ACACCAGCGGCCCGCATCCTCAGGCACATACCAGGCTCCTCCACCCCCGCCGCA
ACACCAGCCCATGATCTCGCCCGTGACACCGGCCTGGCAGCACCACCACTACTT
CCCTCCTTCCTCAAACACACCCTACCAGCAGAACCACGACCGATATATCTGCCG
CACCTGCCACAAGGCGTTCTCGCGGCCCTCGAGTCTGCGCATCCACAGCCATAG
CCACACCGGCGAGAAGCCATTTCGGTGCACACATGCCGGATGCGGCAAAGCCT
TTAGTGTACGGAGCAACATGAAGCGCCATGAGCGCGGCTGCCATACCGGAGG
GCTGTCGCGATGGTGTAA (SEQ ID NO: 54)

>AO090120000155 Transcript 1 (*Aspergillus oryzae*)
ATGGATCTCGCCAGCCTTATCACTCCGGGTCCTGAACCCATCTACAAGTCTCGG
GCATCCTACAGCCCTCCTCCCAGCTCTGCGGGTTCCTACAAGCGCCCGGCTGAA
CACGACTCTTACTTCTCGTACTCGCGCGCCCCGCAAGCCCCTCTTTCCCGCCAG
TCGAGGACCAGCCCAAGTGCTCTCTTCCCTCTATCTGACTCTCTTGGAAGGCG
CCGACAGCGCATCGACATATGCTGCAAAGCGTCAAAGAACCAGCCCACCCCCG
CGCAGGGAGTCTGAGTTCCGTTCACCTTATGACTCAGTCTCAACACCAAATGGC
CCTCCTACTCCACCTTTGCGCCCTGAATCGGGCTTCCACAGCGGCCACCACTCTC
CCTCTGCTTCGTCCGTGACTAGTGGAAAGGCCATCAAGCTCGAGTCGTACTCGC
AAACCCCCATGACACTGCCTAGCCCGTCCGATAGATCCTCGATCTCCAGCCAGG
GCTCTGTCCACCACGTTTCCGCTGCTCCCTACGCTTCTCCTGCCCCCAGTGTGGC
CTCGTACTCTTCGCCGGTTGAATCCTCGGCTCCGTCCGCCATGTACTACCAGAG
ACCTTCCGGCTCCTACCAGACCCCCGCTACTGTGCCTAGCCCCTCCGCTGCTCCT
ATGCCTGCATCTGCCACACACCAGCAGATGATTACTCCCGTCACTCCGGCCTGG
CAGCACCACCACTACTTCCCGCCTTCCAGCTCGGCACCCTACCAACAGAACCAC
GACCGGTATATCTGCCGGACTTGCCACAAGGCCTTCTCCAGACCATCCAGCCTG
CGCATCTCACTCTCACAGCCACACTGGCGAGAAGCCATTCCGCTGCACCCACGCC
GGCTGCGGTAAGGCGTTCAGCGTACGAAGCAACATGAAGCGCCACGAGCGCGG
CTGCCACACCGGACGCCCCGTCGCCACCGCCATGGTATAA (SEQ ID NO: 55)

>ACLA_097790 Transcript 1 (*Aspergillus clavatus*)
ATGGATCTCGCAAACCTCATCTCGCATCCCACCTCCGAGGCTGCCTCGACTTTC
AAGTCGAGGTCAGCTCAGAGTCCTCCCGCCTTTCAAGCGAACCCTTACAAGCGT
CTCTCCGGATCGTCGATGAGCTCTTACTTCACCTCCGTACCGACGACCGCGACA
TCGTATTCTCGCACCCCGCAGCCACCACTCTCCCCACCCGTCGACGACCGGCCC
AGATGTTCGCTGCCCTCAATCTCGACTCTACTGGAGGGTGCAGACAGCGCAGCC
GCACATGCAGCGAAACGCCAAAGAACTAGCCTCTCGGCGCATAGGGATCTTGA
TGCCCGTCCTCAGTCGCAACCGTATGACACGATCACCCCACATGCCTTGCCACC
TACGCCGCCATTGCGTCCTGGCTCGGGTTTTCGCAGCAACGGCCATTCGCCTTC TABLE 6-continued Coding region sequences of some mtfA homologs from other fungal species AGCCTCGTCTGTTTCCGCAACGAGCGCCAGCACGGTGATCAAGACCGAAACAT
ATCCTCAGCCTCACATCGGCCTTCCCAGCCCGACAGATCGCTCCTCCATCTCCA
GCCAAGGATCGGTGCAGCATGCGCCCGGAGCGCCGTATGCGTCGCCAGCGCCT
AGCGTGGCATCTTACTCGTCACCTGTCGAGCCTTCCACACCGTCCAGCGCAGCC
TACTATCAAAGAAAGGCCCCTTCAGCTCCCTTCCAGAACCCAGGCAGCGTCCCC
TCAGCATCGGCCGCTCACCAGCAGCTTATCACCCCCATCACCCCCGCCTGGCAA
CACCACCACTATTTCCCCCCATCCAGCTCAACCGCCTACCAGCAGAACCATGAT
CGCTACATCTGCCGCACCTGCCACAAAGCGTTCTCGCGCCCTTCCAGTCTGCGC
ATCCACTCCCACAGCCACACGGGCGAGAAGCCCTTTCGCTGCACACACGCCGGC
TGCGGCAAGGCCTTCAGCGTGCAAGCAATATGAAGCGCCATGAGCGTGGATG
CCATACAGGCCGCCCAGTCGCCACTGCTATGGTGTCATAA (SEQ ID NO: 56)

>gi|317033475: 64-1041 *Aspergillus niger* CBS 513.88 C2H2
finger domain protein, mRNA
ATGGATCTCGCCAGCCTCATCTCCCACCCGGGACCCGATCCCATCATGAAGTCT
AGAGCCTCATACAGCCCTCCCATGACTTCCTACAAGCGCTCCATCGAACACACC
TCGGACTCCTACTTCCCCTCCGTCCCGATCTCCTACACCCGCTCCCCGCAGCCTC
CTCTCTCCCCGCCTGTCGAGGACCAGTCCCCCAAGTGCTCTCTTCCCTCCATCTC
TACCTTGCTCGAGGGCGCAGATGGCGCAGCTATGCATGCAGCAAAGCGCACTA
GAATGACCCCTCCTCTGCAACGCGACCTTGATTCCCGCCAACAGTCGCAAGCAT
ATGACCTCAAAGCTAACGGCCCCCAAATCGCCTTGCCCCCCACCCCCCCATTGC
GCCCCGGTTCTAGCTTCCACAGCGCCGGACACTCCCCCGCCTCCTCCATCTCTGC
TGCCAGCGATGCTGCTGCGCCCAAGCGCTCCGACTCCTACCCTCAAGTGCCCAT
GGCTCTGCCTAGCCCCTCGGATCGCTCGTCATCTCCAGCCAGGGTTCAGTTCA
GGGTGTCTCCAGTGCTTCCTACGCTTCTCCCGCTCCCAGCGTCTCTTCCTACTCC
TCTCCCATTGAGCCTTCGGCCTCGTCCGCCATGTTCTACCAACGCACGGCTCCCT
CCACTTCCGCCGCTCCTCTCCCGACGCCAGCAGCACCGCAACAGATTATCTCCC
CTGTGAACCCTGCCTGGCAGCACCACCACTACTTCCCTCCCTCCAGCACCACGC
CCTACCAGCAGAACCATGATCGCTATATCTGCCGCACCTGCCACAAGGCCTTCT
CGAGACCCTCCAGCCTGCGCATCCACTCCCACAGCCACACGGGCGAGAAGCCC
TTCCGCTGCACCCACGCCGGTTGTGGGAAGGCCTTCAGCGTGCGCAGCAACATG
AAGCGTCATGAGCGTGGCTGCCACAGTGGTCGGCCCGTCGCAACCGCCATGGTT
TAA (SEQ ID NO: 57)

>(gi|358370982: 305608-305869, 305944-306659) *Aspergillus
kawachii* IFO 4308 DNA, contig: scaffold00014, whole genome
shotgun sequence
ATGGATCTCGCCAGCCTCATCTCCCACCCGGGACCCGATCCCATCATGAAGTCT
AGAGCCTCATACAGCCCTCCCATGACCTCTTACAAGCGGTCCATCGAACAGACT
TCCGACTCATACTTCCCCTCCGTCCCGATCTCCTACACCCGCTCCCCGCAGCCTC
CTCTCTCCCCGCCTGTGGAGGACCACTCTCCCAAGTGCTCTCTTCCTTCCATCTC
TACCTTGCTTGAGGGCGCAGATGGCGCAGCTATGCACGCAGCAAAGCGTACTA
GAATGACCCCTCCTCTGCAGCGCGACCTTGATTCCCGCCAACAGTCGCAAGCAT
ATGACCTCAAAGCCAACGGCCCCCAAATCGCCCTGCCCCCACGCCCCCATTGC
GCCCTGGGTCTAGCTTCCACAGCGCCGGCCACTCCCCCGCTTCCTCCATCTCTGC
TGCCAGCGATGCTGCTGCGCCCAAGCGCTCCGACTCCTACCCTCAAGTGCCCAT
GGCTCTGCCTAGCCCTTCGGATCGGTCGTCCATCTCCAGCCAGGGTTCCGTTCA
GGGTGTCTCCAGCGCTTCCTACGCTTCTCCCGCGCCCAGCGTCTCTTCCTACTCC
TCTCCCATTGAGCCTTCGGCCTCCTCCGCTATGTTCTACCAGCGCACGGCGCCTT
CCACTTCGGCCGCTCCTCTCCCGACACCGGCAGCACCGCAACAGATTATCTCCC
CTGTGAACCCTGCCTGGCAACACCACCACTACTTCCCTCCCTCCAGCACCACGC
CCTACCAGCAGAACCATGATCGCTATATCTGCCGCACCTGCCACAAGGCCTTCT
CGAGACCTTCCAGCCTGCGCATCCACTCCCACAGCCACACGGGCGAGAAGCCCT
TCCGCTGCACCCACGCTGGTTGTGGGAAGGCCTTCAGTGTGCGCAGCAACATGA
AGCGTCATGAGCGTGGTTGCCACAGTGGTCGGCCCGTCGCAACTGCCATGGTAT
AA (SEQ ID NO: 58)

>Afu6g02690 Transcript 1 (*Aspergillus fumigatus*)
ATGGATGTCGCAAGCCTCATCTCGCCTTCTGAATCGGATACTGTCCCGACCTTC
AGGTCAAGATCGATTCAGAATTCATCAGCCAGCCATTACAAGCGCCTCTCCGAA
CAATCAACAGGCTCTTACTTCTCTGCTGTGCCAACACATACAACGTCTTACTCTC
GTACCCCTCAGCCACCACTGTCCCCTCCAGCGGAGGACCAGTCCAAATGCTCGC
TTCCTTCCATCTCGATCCTGCTTGAGAACGCAGACGGTGCCGCCGCACACGCAG
CAAAACGCCAACGAAACAGCCTATCAACGCACAGGGATTCGGATCCCCGGCCT
CCATATGACTCGATCACACCACACGCCATGCCGCCAACGCCGCCATTGCGTCCC
GGTTCGGGCTTCCACAGTAATGGCCATTCTCCCTCGACATCATCTGTCTCTGCCG
CTAGCTCCAGCGCTTTGATGAAAAACACAGAATCGTATCCTCAGGCGCCAATTG
GGCTTCCTAGTCCAACGGATCGATCCTCGATCTCGAGCCAAGGGTCCGTTCAGC
ATGCCGCCAGCGCTCCATATGCTTCGCCTGCTCCCAGCGTATCGTCCTTCTCTTC
TCCCATCGAGCCCTCTACACCATCAACTGCCGCTTACTACCAAAGAAATCCTGC
GCCGAACACCTTCCAAAACCCAAGCCCTTCCCCAAACATCCACAGCATCTCT
TCCCTCCCCGGGTCATCAACAGATGATTTCTCCCGTCACCCCCGCCTGGCAACA
TCACCACTACTTCCCCCCGTCCAGTTCCACGTCTTACCAGCAGAACCATGATCG
CTACATCTGCCGGACATGCCACAAGGCCTTTTCGCGGCCCTCCAGCCTGCGCAT
CCACTCCCACAGCCACACTGGCGAGAAGCCTTTCCGTTGCACACATGCCGGCTG
CGGCAAGGCCTTCAGCGTACGGAGCAATATGAAGCGTCATGAGCGTGGTTGCC
ATACGGGCCGCCCAGTTGCTACCGCCATGGTCCAATAG (SEQ ID NO: 59)

TABLE 6-continued

Coding region sequences of some mtfA homologs from other fungal species

>NFIA_049000 Transcript 1 (*Neosartorya fischeri*)
ATGGATGTCGCAAGCCTCATCTCGCCTTCTGAATCGGATACAGTTCCGACCTTC
AGGTCAAGATCGATTCAGAATTCATCAGCCAGCCATTACAAGCGCCTCTCCGAA
CAATATACGGGCTCTTACTTCTCTGCTGCACCAACACATACGACGTCTTACTCTC
GTACCCCTCAGCCACCACTGTCCCCTCCAGCCGAGGACCAGCCCAAATGCTCGC
TTCCTTCCATCTCGATTCTGCTTGAGAACGCAGACGGTGCCGCCGCACACGCAG
CAAAACGCCAAAGAACCAGTCTATCAACGCACAGGGATTCGGGGCCTCCATAT
GACTCGATCACACCACACGCCATGCCACCAACGCCGCCACTGCGTCCTGGTTCG
GGCTTCACAGTAATGGCCATTCTCCCTCGGCATCGTCTGTCTCTGCCACCAGCT
CCAGCGCTGTGATGAAGAACACCGAAACGTATTCTCAGGCGCCAATTGGGCTTC
CTAGTCCGACGGATCGATCCTGATCTCGAGCCAAGGGTCCGTTCAGCATGCCG
CCGGCGCTCCATATGCTTCGCCTGCTCCCAGCGTGTCGTCCTTCTCTTCTCCCGT
CGAGCCCTCTACACCATCAACTGCCGCTTACTACCAAAGAAACCCTGCGCCGAA
CACCTTCCAAAACCCAGGCTCCTTCCCTCCAACATCCGCGGCCTCTCTTCCTTCC
CCGGGTCATCAACAGATGATTTCTCCCGTCACCCCCGCCTGGCAACATCACCAC
TACTTCCCCCCGTCCAGTTCCACGCCTTACCAGCAGAACCATGATCGCTACATCT
GCCGGACATGCCACAAGGCCTTCTCGCGGCCATCCAGCCTGCGCATCCATTCCC
ACAGCCACACTGGCGAGAAGCCTTTCCGCTGCACACATGCCGGCTGCGGCAAG
GCCTTTAGCGTACGAGCAATATGAAGCGTCACGAGCGTGGTTGCCATACGGG
CCGCCCGGTTGCTACCGCCATGGTCCAATAG (SEQ ID NO: 60)

>AFL2G_08180 Transcript 1 (*Aspergillus flavus*)
ATGGATCTCGCCAGCCTTATCACTCCGGGTCCTGAACCCATCTACAAGTCTCGG
GCATCCTACAGCCCTCCTCCCAGCTCTGCGGGTTCCTACAAGCGCCCGGCTGAA
CACGACTCTTACTTCTCGTACTCGCGCGCCCCGCAAGCCCCTCTTTCCCCGCCAG
TCGAGGACCAGCCCAAGTGCTCTCTTCCCTCTATCTCGACTCTCTTGGAAGGCG
CCGACAGCGCATCGACATATGCTGCAAAGCGTCAAAGAACCAGCCCACCCCCG
CGCAGGGAGTCTGAGTTCCGTTCACCTTATGACTCAGTCTCAACACCAAATGGC
CCTCCTACTCCACCTTTGCGCCCTGAATCGGGCTTCCACAGCGGCCACCACTCTC
CCTCTGCTTCGTCCGTGACTAGTGGAAAGGCCATCAAGCTCGAGTCGTACTCGC
AAACCCCCATGACACTGCCTAGCCCGTCCGATAGATCCTCGATCTCCAGCCAGG
GCTCTGTCCACCACGTTTCCGCTGCTCCCTACGCTTCTCCTGCCCCCAGTGTGGC
CTCGTACTCTTCGCCGGTTGAATCCTCGGCTCCGTCCGCCATGTACTACCAGAG
ACCTTCCGGCTCCTACCAGACCCCTGCTACTGTGCCTAGCCCCTTCCGCTGCTCCT
ATGCCTGCATCTGCCACACACCAGCAGATGATTACTCCCGTCACTCCGGCCTGG
CAGCACCACCACTACTTCCCGCCTTCCAGCTCGGCACCCTACCAACAGAACCAC
GACCGGTATATCTGCCGGACTTGCCACAAGGCCTTCTCCAGACCATCCAGCCTG
CGCATCCACTCTCACAGCCACACTGGCGAGAAGCCATTCCGCTGCACCCCACGCC
GGCTGCGGTAAGGCGTTCAGCGTACGAAGCAACATGAAGCGCCACGAGCGCGG
CTGCCACACCGGACGCCCCGTCGCCACCGCCATGGTATAA (SEQ ID NO: 61)

>ATEG_07186 Transcript 1 (*Aspergillus terreus*)
ATGGATCTCGCCAGCCTAATCACCCCGGGACCTACTCCCTTCGCATCTCGTCCG
CCTCGAGCTTCCTACAGTCCCCCGGCTTCTTCGTCCGGTTCATACAAGGCCCCTA
ATGAGCCTCATTATACGGGGTCATACTTCCCCGCCATGCCTACTGCGACTCCAG
TGACCACCACTACTTCCTACTCGCGCTCGCCGCAACCGCCTCTCTCTCCTCCCGT
CGAGGACCAGCCCAAGTGCTCTCTCCCCTTCCATCTCCACCCTTCTCGGTGCCGCA
GACAGCGCCCCAATGCCCCCAGCTAAGCGCCAGCGCCTCAGTACCCCGCGCG
CAGAGAATCCGATAGCTGGCTCCAGACAACACCATGCCTGCCTCCGACCCCCCC
GTTGCGTCCAGGCTCCGGCTTCCACAGCAGCGGCCACCGCTGCCATCATCCAA
CAAGCCCACCGAATCGGCGCCCTTCCCGCAACAGCCCCCGTGACGCTCCCCAG
TCCCACCGAGCGCTCCTCCATCTCCAGCCAGGGCTCCGCGCACGCGCCGTACGC
TTCGCCCGCCCCAGCGTCGCCTCGTACTCGTCTCCCGTCGAGCCCTCCCCGGCT
CCCTCCACGCTGTACTACCAGCGCCCCGCCGCGCCTCCAGCGCCTTCCGCCGCC
GCCGCTGCTCCCGCTCCCGCGCAGCCCTTGATCTCCCCCGTCACCCCGGCCTGG
CAGCACCACCACTACTTCCCGCCTCCAGCTCCACCCCCTACCAGCAGAACCAT
GACCGGTACATCTGCCGTACCTGCCACAAGGCATTCTCGCGCCCCTCGAGTCTG
CGCATCCATTCGCACAGTCACACCGGCGAGAAGCCCTTCCGCTGCACCCCACGCC
GGCTGCGGCAAGGCCTTCAGCGTCCGCAGCAACATGAAGCGCCATGAGCGCGG
ATGCCACAGCGGCCGTCCGGTTGCTACCGCTATGGTATGA (SEQ ID NO: 62)

>gi|255951067|ref|XM_002566255.1|*Penicillium chrysogenum*
Wisconsin 54-1255 hypothetical protein (Pc22g24110) mRNA, complete cds
ATGGATCTCTCCAACCTCCTCTCTCACAGCGCGGCTGTCAAGCCGATCTATACTC
CTGTCGAGTCCAGTTACTATAAGCGCTCGCCGCCTCTGTCGCCGCCAGCCGAAG
AGCCCAAGGTCTCATTGCCTTCAATCTCGTCTCTCTTTGAGGGTGCTGATGGTGC
TCAGCACGCAGCTACCTCGCTAACCCTAAACCTTCCAGAGCGCCAACGCTTGTC
ACCATCTCTCGGTGACCGCCATGTCCGGGTTCAGTCCTACGAACTGCCCCCAAC
ACCACCTCTGCGCCCCGGCTCTGGCCACGCCCACCGCCGCGCATCTCCCGTGGA
GTCGCTGTCTCACAAGGAAGCACACCAGCATCACCTTCACCGTTCCTCTATCTC
CAGCAACAGCTCAGTCCACATCCCTCGCAACACAGTACCCTACGCCTCGCCTGT
ACCAAGCGTCTCATCCTACACATCTCCAGTCGACGCTCCTCAACAGCCAATGTA
CTACCCTCGCCCACCAACCACATCCTCCTTCCAGCCCTCAACACCAGCATCAGC
ACCCCAGATGCCCCCTGTCCAGGTCCAGACGCAGCAGCCGCACTCGCACTCTCA
CTCGTCTTCGGCTCTCATCTCTCCTGTCACCCCGGCCTGGCAACACCACCACTAC TABLE 6-continued Coding region sequences of some mtfA homologs from other fungal species TTCCCGCCCTCCACCACAGCCCCGTACCAGCAGAACCACGACCGCTATATCTGC
CGTACATGCCACAAGGCTTTCTCGCGCCCTTCCTCCCTGCGCATCCACTCGCACT
CGCACACTGGCGAGAAGCCCTTCCGCTGCACGCATGCCGGCTGCGGTAAGGCTT
TCTCCGTGCGCAGTAACATGAAGCGCCATGAGCGTGGCTGCCATTCTGGTCGCC
CTGCCCCTGCCCCTGCTGCTACTGCGCTTGTCGTATAG (SEQ ID NO: 63)

>gi|119173021|ref|XM_001239026.1|*Coccidioides immitis* RS
hypothetical protein (CIMG_10049) partial mRNA
ATGAACGTTTCAAGCCTGATCACTTGCGATCAGCCGCACCAATTGCGCGCGCCT
GCATCTTCATATTCTGAGCACCGTCGATCCCCATCCATCCCCAAGCCTTTGCAGA
CGGAGAGCAGTTCATGCGCTTCTCCATACTCGCGGTTCGAGCGTCTCCCTCTTTC
ACCGCCGGAGGAGGATGGCAAGACACAGTTCTCACTTCCTTCTATCTCGTCTCT
TCTTCGGGGCGTAGATGGTGTTTCTGATGCGCACGTTGCTAAGAGACAACGAAC
CAACCCTCCTCCTAGCATTGACTTAGGGATGGAGAGACGGACTATAGACCAAA
CATTAAAGCAGAGGCCAGCGCTGCCTTTGACGCCTCCTCTAAGGCCTGAGTCTG
GCATGAATAGCACAAGCCAGTCGCCGTCAACATCATCGCCACCACGAAGCGCC
ATCTCACTACCGAGTCTTGTTCGGAGTTATCCGTCTCCAGTTTCAGAAGTTCCAG
AGGGACGACGGATGTCACAGATATCGCGACATTCGCGAGGGGCTTCGACGTCG
CAAACTTCTCAACCTTTCAGGCCCAGAAACACGTTACCCATCGCCACCAAATGTC
AACTCTCCAACCTTTGCTGCCCCTGTTGAACCAGCGCCAAAGCCGACAGAATAC
TACCCAGCCAGCCGACCGGTAACGTTTCCGCCTGTGGCGTTCGCAGTTCTGCCA
AGCCAGCCAACTCATCCTCAGGTGCTTCCTCTTGGAAGTCCTGCGTGGCAGCAC
CATCATTATTTCCCTCCTTCCAACACAGCAACTTATCCTCTCAATCACGATAGAT
ACATCTGCCGAATATGTCATAAGGCTTTCTCAAGACCGTCCAGCCTGCGAATAC
ACTCCCACAGTCATACTGGCGAGAAGCCTTTCCGGTGCCCCATGCCGGCTGTG
GGAAAGCGTTTAGCGTGCGAAGCAACATGAAGCGACACGAAAGGGGTTGCCAT
CCTGGAAGATCAGCACCACCATCGGCCCTGGTTAACTGA (SEQ ID NO: 64)

>(gi|198250550: c746647-746377, c746321-745555) *Ajellomyces
capsulatus* H88 supercont1.9 genomic scaffold, whole genome
shotgun sequence
ATGAATTTATCCCACTTGGTGACCAGCTATCATAGCCCTCCTTCGACGTATCCAC
ACTCAGGCACTTCGCAAAAGCGCCAGTCCTTGCAGAGCGAATCTTCATTATCTG
TATCGAACGGATACTACGATCGCAATGCTTCAAATCTTGCATATGCCCGCTCTC
CTCAACCACCCTTATCCCCACCTGTCGAAGAGCAGTCCAGATTCTCTCTTCCTTC
AATATCTAGTTTATTGCAAGGAGCTGACCAACTCTCTCCTGTTCATATAGCTAA
AAAACATCGTCCCAATCCACTCTCAACTGGAGAAGTTGATTTAAAATCGCAGGG
CCATGGAGCCACCCAAAAGCCCATACACAGGCCGAGAATGATTTTACCACCGA
CCCCTCCCATGCGCCCAGGCTCCGGATTAGATGGAAGAAATCACTCTCCTGCCG
GATCGTCGCCATCGTCTGCACACTCTCCCATTTCAGTAGCCAATCTCACAAGTTC
GTCATCGGCGGACCCTTCCTATCAGCATCGGATGCCCCAAGGTCCGTTACCCCC
ACAGTCAACCAGATCGTCCGTATCTCAAAATTCTCCTGTCTCTCTACCCGAAAA
GCATTACGCTCCATCCTCCAATTTACCCACCAGCTCGACTCCATTCGCTTCCCCA
GTTGAACCCCTAGCGAATTCTACGGAATATTATCACCGCCCATCCCATCCCCCTT
CTTTTCTCGACATCTATTCCTCTGGCAGCCCCGCCAGCGCAACAGCACCATCACC
ATTCTATGATCTCAACCTGGCAACACCACCACTATTTTCCACCGTCAAATACGG
CTCCCTACCCACAAAATCATGACAGGTATATCTGTCGAATATGTCACAAGGCGT
TTTCTCGGCCTTCTAGTCTGCGGATTCACTCGCACAGCCATACCGGCGAAAAGC
CATTCAAATGCCCGCATGTCAACTGTGGCAAGTCATTTAGTGTCAGGAGTAACA
TGAAGCGACATGAACGGGGTTGTCATACAGGCAGACCTACGCAAGCAGCTTTG
GTGAATTAA (SEQ ID NO: 65)

>gi|258569089|ref|XM_002585243.1|*Uncinocarpus reesii* 1704
conserved hypothetical protein, mRNA
ATGAACGTTTCTAGCCTGATTAGTTGTGATCAGACTGCTCCCTTCCACGGGTCTG
CAACATCATATTTCGAGCATCATCAAAGAATCCGATCGCCTTCCATTCCCAAAA
GATCACACGAAGAGAACAGCTCATCCGCCTCTCCCTACCCTCCTTTTGCAACCC
TGCCTCTTTCGCCACCAGAAGATGACGGGAAGACAACCTTCTCGCTTCCTTCTA
TCTCATCCCTTCTTCAAAGCGTCGACGCTGCTTCTGACACTCACGTTGCCAAACG
GCAACGAGCCAACCCCCCTCCTAGCATTGATTTAGCTCTGGAAGAGACGAGGTGC
CTGTGCGGACCAAGCAATCAGACAAAGGCCAGCCCTTCCACTAACGCCTCCCCT
GCGACCAGAGTCGGGAATGGGCGGTGTAAATCACTCGCCATCTGCATCATCCCC
TCCCCGAACCGCTATCTCACTACCCAGCCTCATTGGAAGTTACCCATCGCCAGT
TTCAGAGGCTCCAGAAGGACGACGAATGTCGCAAATCTCACGACACTCAAGCA
GAACTTCCATCTCTCAATCCTCCCAACATCCAGGGCCGGAAGCCCGCTACCCAT
CGCCACCAACTCTCAGCTCTCCTTCCTTCGCCGCTCCTATTGAACCACCTCCAAA
GCCAGAGTACTACTCTTCTGGTGCCCGACCGACCAACTTTCCGCCAGTAACTTT
CGCTGTCCTTCCAAGTCAACCAACGCATCCGCAGATGGTGGCCTTGGGGAGTCC
TGCCTGGCAGCATCACCACTACTTTCCTCCATCAAACACAGCAACTTACCCACT
CAACCACGACAGATACATTTGCCGAATATGCCACAAGGCATTCTCACGGCCGTC
AAGCCTGCGAATTCACTCGCATAGTCACACAGGCGAGAAGCCGTTTCGATGCCC
CCATGCCGGCTGCGGGAAGGCATTCAGCGTGCGAAATCAGCCCCGCAGCCAGC
GCTCGTTAATTGAAAAACGGAAGGGGTACGCGATCGGATTTGACGAATGGGTT
TTGACGATGATAACGCCCACAATACGGAGTACCAACGAGCAAATCTACACAAC
TGCATCGTGTAAGATCGCGAACGTGGCGGTGATCAACATCAATAGAAGAATTG
CCGAGCTTCGCAAGTCATTTCGCAACAGACGTTCGAATGGGACGTTGTCCCCGA
CGAAGCGCCGCGTCAAATTGGCATTTTCCCTGGATTGCCAATCTACATCCTCAT TABLE 6-continued Coding region sequences of some mtfA homologs from other fungal species

CCAGGCTTGCCCTTTTACCGCAGTCCCTTTGA (SEQ ID NO: 66)

>gi|212537380: 615-1358 *Penicillium marneffei* ATCC 18224
C2H2 finger domain protein, putative, mRNA
ATGGATAACGTGCCTGCAAGCAAACGTGCCCGCCATGACTCAGGCGACTACAG
CCGTGGCTTCTTACCTCCAACACCGCCAATGCGCCCTGCTCCGGGTTCACAGA
AGGCAGCTCGCCTGCCTCTCTTCCTTCTGGACGATCACATTCTGCTTCTATAAGC
AGCGCAGTTTCGCATCCATCACACCAACAGCGTACATCTTTACCATCTATTTCTG
CATCTCTTCAAAATACACCAATCCACCCTTCAGAGCGTTTATCCATCTCCTCTCT
CGCCTCTCACGACTCTTCCCGCCTTTCTCACGCCATTCCCAGCCCTTCATCTACC
ACAGCCTCGATCACAACCACAGCGACTCCATCAACGTCATATTATTCTACATCA
GAAGAGAAAGCATATCCACGATACATAGCACATCCGCTCCAGTGACCCCATC
AACACTTGTCCCACCACCACCCGCCATGCTCTCGCCTGTGAACCACCCAGGCTG
GCAACACCACCACTACTTCCCACTTTCGACTACGACATCATACCCACAAAACCA
CGAGCGGTATGTCTGCCGTACATGCCACAAGGCATTCTCTCGTCCATCCAGTCT
TCGAATCCACTCGCATAGCCACACTGGCGAGAAGCCATTCCGATGCACACATGC
AGGCTGCGGAAAGGCGTTCAGTGTGCGCAGCAATATGAAGCGCCACGAGCGCG
GCTGTCATAGCGGACGACCTATGACGGCAACTGTTGTCTAA (SEQ ID NO: 67)

>(gi|325974178: c673869-673659, c673604-673177, c673115-672801)
*Botryotinia fuckeliana* isolate T4 SuperContig_50_1 genomic
supercontig, whole genome
ATGGCCTCATCGTTGGTTTCAAACCCTTATACAGTCCATCCTATGGCTCAACACT
CTTCCTACACATACGTTAACGCACCTCAACCACCACCCTCACCACCCGTAGACG
AAACTTCAAAGTGTTCCCTACCATCTATTTCAAGTCTGTTGGGTTTGGCCGATGG
ATCGAGTCCAACAGAGCAGGCTCAGCAACAGTCATCGCCACAACAAGCAGCTT
TCAAGGAAGATTATAGACCAGAGTCTGGACATCAGTACGGTCCTTCCTCATCAA
TGAGCTCTCGAGGTGCTCTTCCACCTACACCCCCAATGCAATCTGACGGTGGAT
TCGACGGCAGACAATCGCCGTCTCAAGCATCTACTTCATCATATTCAGTAGTTT
CTGCGCCAAATTATTACTTTAATCCTTCTCAAGTCTCGGCCATCAACAATATGGA
GCCTCATGCACAACGCCAGCCAGTCCAAACTGTTACTCGAAGAGTTTCAATGCC
AGTGTCTTCAATGCAATATGGCCATTCTCCGTTCAACGGATCCTACACTATGTCT
CCTGGCGCCCAGTCTTTGAGCTCTTACTATCCAAGCCCGATACAAACACAATCT
CCCCAAGTTTCTTCACTATACTATCAAAGACCACTTCCACAGCAATTTCCTCCGC
CAATGATGCCAGTGTCTGTGACTCTGACTCCATCATCCGGTGCTAATCCATGGC
AACATCATCACTATATCTCTCCTTCCTCAGCAGCCTCATTTCCTCAGTCACAAGA
TAGATACATCTGTCAGACTTGTAACAAAGCTTTTTCGAGACCATCGAGTCTCCG
AATCCACAGCCACTCACATACCGGCGAGAAACCCTTCAAGTGTCCACATCAAA
ACTGTGGGAAAGCCTTCAGCGTTAGGAGCAACATGAAGAGACACGAGCGAGGT
TGTCACAGTTTTGAAAGCGCTTCAATGGTCTGA (SEQ ID NO: 68)

>ENA|EGO52630|EGO52630.1 *Neurospora tetrasperma* FGSC 2508
hypothetical protein: Location: 1 . . . 1000
ATGGCACCCACGACGTTAACGCCTCAATATCCTGCCCAGCCTTATGGCTTCGCT
CCGCCACCCTCCCCTCCTTTGGACGACTCCAACAAGTGCTCCCTGCCCTCGATTT
CGAACCTGCTTGTCATGGCCGATCAGGGATCTCCTACCTCAGAGACATCTCCTC
AGTCTCAGCAATTGCACTTCTCAAAGCCTGACAACCGTCCCAACTCTTCCCAGT
TTGGCAACCCAGCATCGATCAGGGCGAACCTCCCCCCTAGTCCTCCCATGTCTT
CGGAAGCTTCTTTTGAAGGATACCGCTCTCCTTCAAGCAAGCCAGCAAGCCAGT
CTCAGGGCAGCTCCAACTACTACTATGAGACCACGCCGCCTTTGAGCCAGCATG
AAGCCGACTCCCGGCAGATGGCCACTGCTGCACCCAGAGCCCCTGTTCAGTCAT
CAACCTTCCAAACACAGTACCCGTCGTCAGCCGGCTACTCGAGTCAGTCAGGCA
TGAACCCTTATTACCCTCCCATGCAGCCGACACCCCCTCCGCAGCAGAGATGT
CGGGCTTGTATTATCAGCGACCACTCCCTCAGACTTTCACCCCTGCTGTGCCAGT
TCCAGTCACTCTCGCACCAGTCACGGGAGCCAACCCTTGGCAACATCACCACTA
TATTGCTCCTTCTTCCACTGCATCTTTTCCGCAGTCTCAAGACCGGTACATCTGC
CAGACTTGCAACAAGGCCTTCTCTCGACCGAGCTCATTGCGAATCCACAGCCAC
TCTCACACTGGTGAGAAGCCTTTCAAGTGCCCCCATGCAGGCTGCGGAAAGGCC
TTCAGCGTTCGCAGTAACATGAAGCGTCATGAGCGTGGCTGCCACAGTTTTGAG
AGCAGCAACGGCAGAAGCAGTGGCAACAGCAACAACGGCGCATCTGCCTAG
(SEQ ID NO: 69)

>gi|85113804|ref|XM_959497.1|*Neurospora crassa* OR74A
hypothetical protein partial mRNA
ATGGCACCCACGACGTTAACGCCTCAATATCCTGCCCAGCCTTATGGCTTCGCT
CCGCCACCCTCCCCTCCTTTGGACGACTCCAACAAGTGCTCTCTACCCTCGATTT
CGAACCTGCTTGTCATGGCCGATCAGGGATCTCCTACCTCAGAGACATCTCCTC
AGTCTCAGCAATTGCACTTCTCAAAGCCTGACAACCGTCCCAACTCTTCCCAGT
TTGGCAACCCAGCATCGATCAGGGCGAACCTCCCCCCTAGTCCTCCCATGTCTT
CGGAAGCTTCTTTTGAAGGATACCGCTCTCCTTCGAGCAAGCCAGCAAGCCAGT
CTCAGGGCAGCTCCAACTACTACTATGAGACCACGCCGCCTTTGAGCCAGCATG
AAGCCGACTCCCGGCAGATGGCCACTGCTACACCTAGAGCCCCTGTTCAGTCAT
CAACCTTCCAAACACAGTACCCGTCGTCAGCCGGCTACTCGAGTCAGTCAGGCA
TGAACCCTTATTACCTCCCATGCAGCCGACACCCCCTCCGCAGCAGAGATGT
CGGGCTTGTATTATCAGCGACCACTCCCTCAGACTTTCACCCCTGCTGTGCCAGT
TCCAGTCACTCTCGCACCAGTCACGGGAGCCAACCCTTGGCAACATCACCACTA
TATTGCTCCTTCTTCCACTGCATCTTTTCCGCAGTCTCAAGACCGGTACATCTGC TABLE 6-continued Coding region sequences of some mtfA homologs from other fungal species CAGACTTGCAACAAGGCCTTCTCTCGACCCAGCTCATTGCGAATCCACAGCCAC
TCTCACACTGGTGAGAAGCCTTTCAAGTGCCCCCATGCAGGCTGCGGAAAGGCC
TTCAGCGTTCGCAGTAACATGAAGCGTCATGAGCGTGGCTGCCACAGTTTTGAG
AGCAGCAACGGCAGAAGCAGTGGCAACAGCAACAACAGCGCATCTGCCTAG
(SEQ ID NO: 70)

>gi|389646062: 228-1157 *Magnaporthe oryzae* 70-15 hypothetical
protein (MGG_12536) mRNA, complete cds
ATGGCCGCCACCATGATACAACAGCCCTACCCAATTCATCAGCAGCAGTCGCAG
TACAGCTACATGGTTCAGCCTCAGGGCCCGCCTTCGCCGCCCATGGACGACAAC
AAGTGCTCGCTTCCATCCATCTCGAACCTGCTCGGCTTGGCGGATCAAGGATCA
CCAACCTCGGAGACCTCGGCCCAATTCCGCGAGGAGCAGAAGCAACAACAAGC
AGCACAACAATCAAGACCCAACTCGTCACACTATAGCAATGCAGTCCAGTCTGT
GCGCCAGGGCATCCCGCCAACGCCGCCAATGACTTCTGAGACCTCATTCGACGG
TTACAACTCGCCCTCAAACAAGTCGGTCAGCCAGCTTCCCGCCACTGGCTACTA
CTTTGAGGCGACGCCACCCCCAGGCCACATGGAGATGGAGCCCCGCCCGCACA
TGACCAGCGTTTCCAGGGTCCCAGTTCAGGCTCCCTTCGCTCAGTCTGCCTACTC
AGCTCCCTATGGCATGCCCCCAGCAACCCGATGGCGGCCTACTACCCGACGAT
GCAGCCCACGCCTCCTCCTCAGCAGCCTCAGATCTCTAGCCTTTACTACCAGAG
ACCCCTTCCTCAGGCCTTCCCTCCCATGCCTGTCAACGTCTCCATGGGTCCTCAG
TCTGGCGCCAACCCGTGGCAGCACCACCACTACATCTCGCCATCTGCTGCGGCA
TCTTTCCCTCAGTCCCAGGACCGCTACATCTGCCAGACCTGCAACAAGGCATTC
TCCCGCCCGAGCTCCTTGAGGATACACAGCCACTCGCACACTGGCGAGAAGCCT
TTCAAGTGCCCTCACGCCGGCTGCGGCAAGGCTTTCAGCGTGCGCAGCAACATG
AAGCGCCACGAGAGGGGCTGCCACAACTATGACAGCAGCAGCAGCAACGGCAC
CGCCATGCACTGA (SEQ ID NO: 71)

>gi|116193176|ref|XM_001222400.1|*Chaetomium globosum* CBS
148.51 hypothetical protein (CHGG_06306) partial mRNA
ATGGCAAACACAATGGTCACACACTACGCGCACGTACCTCAACATAGCCTTCAG
TATGGCTACATGCCGCCACCTTCACCGCCAATGGATGAGGCGGCAAAGTGCTCG
CTCCCCTCTATCTCGAACCTCCTCGGGCTTGCAGACCAAGGATCGCCGACTTCG
GAAACGTCGCCCCAGTCCCAGCAGCAGCAACAGGCGCAGCAGCAGCAGCAACA
GCAATGTATGAGCAGCTCGTGGTGGGATATGGGACACCTAGATACTGACTCGA
CCCCAGCGCAAGGATCCAAGCCGGAGACGAGGCCCAACTCYTCGCATTACACC
AACCCGGTAACCATTCGGACAGGACTCCCGCCCAGCCCGCCCATGTCCTCGGAT
GCATCCTTTGAAGGTTTCAACTCGCCATCGACCAGGTCGGTGAGCCAGGTGCCG
AACGGGTCAAACTACTTCTTTGAGACAACGCCACCGCTTCAGATGGAAGCCGAT
GCACGGCAGATGACCGCTGCCGCCGCCGTCCCGCGAGTTTCTGTCCAGGCTTCA
GCCTACCAGCCCCAGTACGCTCCCGGCCCTGCGTACATGAGTCAACCAGCCATG
ACCTCATACTATCCTCCGATGCAATCCGCGGCGCCACCGCAGACGCAAATGTCC
GGCCTCTACTACCAACGACCGCTTCCTCAGTCTTTTCCGCCTCCGATGTCCATGT
CTATGACTCTTGCGCCGACGGCCGGGAACCCCTGGCAGCACCATCACTACATTG
CCCCTTCGGCGTCAGCATCCTTTCCCCAGAGCCAGGACCGGTATATCTGCCCGA
CGTGCAGCAAAGCCTTCTCGCGGCCCAGCTCGCTGCGGATCCACAGCCACTCGC
ACACGGGCGAGAAGCCCTTCAAGTGCCCGTTCCCGGGTTGCGGCAAGGCCTTCA
GTGTGCGCAGCAACATGAAGCGGCACGAACGTGGGTGCCACAACTACGACAGC
AGCAGCACGACGAGCAGCACCGGCACCATGAACAGCAACACCGGGGAAGCC
GTCCCTGA (SEQ ID NO: 72)

>(gi|342883535: 113711-113828, 113878-114590) *Fusarium
oxysporum* Fo5176 contig01821, whole genome shotgun sequence
ATGGAGGAACAAAAGTGCTCTCTACCCTCAATCTCGAACCTCTTGGGTTTGGCC
GATGCCGGCTCACCCACGAGTGAGTCCTCACCAACTTCACGGCAACATTCTCCT
CGCTTTGAAGTTCCTCCACCTTCACATGGTCATAGCCGAGCTGGATCTGAATGG
GCTAAATCATCGCACCGTGGGCTTCCCCCTACACCACCTATGAGCACAGACGCA
TCTTTCGAAGGCTACAGCTCCCCCACAAGGAAACCATCCAACCAGGCGTATCCA
GGCTCAGCACCAAGAACATACTATTACGAGACCACACCACCTCTAGAAGCCGA
TGCACAGCGTCAGGCATCAGTAACGGCTATTCCTCGAGCAACACCTCCAGCAAC
GGCTCCTTATCCTCAGCAAGCTCACCCCACGGTATACGCCAACCCAGCACCAGT
GGGCGCTTATTACCGGCGGCACAGGTGCCTCCTGCTGTCCAGCCTCAAGAGAT
GAACCCTTACTACCAGCGCCCTCTCCCACAGGCTTATCCCCACCAGTGAGCAT
GCCAGCACCTGCTCCCTCGGGAGCAAATCCTTGGCAGCACCATCACTATCTTAA
CCCAACTGGAGCGGCGGCATTCCCGCAAAGCCAGGACCGGTATATTTGCCCGA
CTTGCAACAAAGCCTTTAGCAGGCCCAGCAGTCTCCGAATCCACAGTCACTCAC
ATACCGGAGAGAAACCCTTCAAGTGTCCCCATGCTGGATGTGGCAAGGCTTTCA
GCGTACGCAGCAACATGAAACGTCATGAGAGGGGCTGTCACAGCTTCGAATTT
AATGGGTCTGTGATTCGGGGTTGA (SEQ ID NO: 73)

TABLE 7

Amino acid sequence comparison of *Aspergillus nidulans* MtfA in with putative orthologs in other fungal species.
The comparisons were done using the BLASTp tool provided by NCBI (National Center for Biotechnology Information)
and EMBOSS Needle - Pairwise Sequence Alignment tool provided by EMBL-EBI (European Bioinformatics Institute).

| | NCBI | | EMBOSS Needle - Pairwise Sequence | | |
|---|---|---|---|---|---|
| | | E-value | Alignment (global alignment) | | |
| Name of the species, with the strain information | Accession number | (BLASTp) | Length | % Identity | % Similarity |
| *Aspergillus oryzae* [RIB40] | XP_001823905.1 | 0 | 332 | 64.2 | 70.8 |
| *Aspergillus clavatus* [NRRL 1] | XP_001270264.1 | 2E−111 | 347 | 65.1 | 71.2 |
| *Aspergillus niger* [CBS 513.88] | XP_001395874.1 | 5E−106 | 336 | 62.8 | 71.1 |
| *Aspergillus kawachii* [IFO 4308] | GAA87693.1 | 6E−106 | 336 | 62.8 | 70.8 |
| *Aspergillus fumigatus* [Af293] | XP_747808.1 | 2E−100 | 342 | 62 | 71.3 |
| *Neosartorya fischeri* [NRRL 181] | XP_001257459.1 | 5E−94 | 353 | 60.9 | 68.8 |
| *Aspergillus flavus* [NRRL3357] | XP_002380969.1 | 9E−94 | 332 | 64.2 | 70.8 |
| *Aspergillus terreus* [NIH2624] | XP_001209872.1 | 6E−93 | 344 | 62.5 | 68.9 |
| *Penicillium chrysogenum* [Wisconsin 54-1255] | XP_002566301.1 | 3E−74 | 351 | 49.3 | 58.7 |
| *Coccidioides immitis* [RS] | XP_001239027.1 | 1E−64 | 355 | 44.5 | 54.6 |
| *Ajellomyces capsulatus* [H88] | EGC49893.1 | 9E−64 | 364 | 45.9 | 58.0 |
| *Uncinocarpus reesii* [1704] | XP_002585289.1 | 6E−54 | 440 | 34.1 | 42.0 |
| *Penicillium marneffei* [ATCC 18224] | XP_002148846.1 | 1E−52 | 342 | 38 | 43.9 |
| *Botryotinia fuckeliana* | CCD44702.1 | 6E−47 | 347 | 40.3 | 51.9 |
| *Neurospora tetrasperma* [FGSC 2508] | EGO52630.1 | 2E−44 | 347 | 39.8 | 50.1 |
| *Neurospora crassa* [OR74A] | XP_964590.1 | 2E−44 | 343 | 39.1 | 50.1 |
| *Magnaporthe oryzae* [70-15] | XP_003720663 | 4E−50 | 335 | 38.5 | 50.4 |
| *Chaetomium globosum* [CBS 148.51] | XP_001222401.1 | 6E−39 | 382 | 34.0 | 45.8 |
| *Fusarium oxysporum* [Fo5176] | EGU84033.1 | 3E−38 | 350 | 34.9 | 43.4 |

TABLE 8

Comparison of MtfA with other *A. nidulans* $C_2H_2$ transcription factors

| Transcription Factor | Accession No. (NCBI) | % identity | length | % identity of the DNA binding domain |
|---|---|---|---|---|
| FlbC | ACP28867 | 25.3 | 399 | 29.0 |
| BrlA | XP_658577 | 21.4 | 457 | 19.2 |
| SteA | O74252 | 11.3 | 742 | 27.9 |
| PacC | CAA87390 | 6.1 | 830 | 9.8 |
| SltA | XP_660523 | 11.7 | 720 | 21.7 |
| CrzA | XP_663330 | 14.3 | 746 | 25.8 |
| CreA | AAR02858 | 6.4 | 607 | 25.0 |

Note:
The pairwise sequence alignment was carried out with EMBOSS Needle, provided by EMBL-EBI.

Publications

These publications are incorporated by reference to the extent they relate materials and methods disclosed herein.

Brown, D. W., J. H. Yu, H. S. Kelkar, M. Fernandes, T. C. Nesbitt et al., 1996 Twenty-five coregulated transcripts define a sterigmatocystin gene cluster in *Aspergillus nidulans*. Proceedings of the National Academy of Sciences of the United States of America 93: 1418-1422.

Calvo, A. M., J. Bok, W. Brooks and N. P. Keller, 2004 veA is required for toxin and sclerotial production in *Aspergillus parasiticus*. Applied and Environmental Microbiology 70: 4733-4739.

Calvo A. M. 2008. The VeA regulatory system and its role in morphological and chemical development in fungi. Fungal Genetics and Biology 45:1053-61.

Cole, R. J., and R. H. Cox, 1981 *Handbook of Toxic Fungal Metabolites*. Academic Press, New York.

Duran, R. M., J. W. Cary and A. M. Calvo, 2007 Production of cyclopiazonic acid, aflatrem, and aflatoxin by *Aspergillus flavus* is regulated by veA, a gene necessary for sclerotial formation. Applied Microbiology and Biotechnology 73: 1158-1168.

Kafer, E., 1977 Meiotic and mitotic recombination in *Aspergillus* and its chromosomal aberrations. Adv. Genet. 19: 33-131.

Kato, N., W. Brooks and A. M. Calvo, 2003 The expression of sterigmatocystin and penicillin genes in *Aspergillus nidulans* is controlled by veA, a gene required for sexual development. Eukaryotic Cell 2: 1178-1186.

Keller, N. P., and T. M. Hohn, 1997 Metabolic pathway gene clusters in filamentous fungi. Fungal Genetics and Biology 21: 17-29.

Kim, H. S., K. Y. Han, K. J. Kim, D. M. Han, K. Y. Jahng et al., 2002 The veA gene activates sexual development in *Aspergillus nidulans*. Fungal Genetics and Biology 37: 72-80.

Miller, B. L., K. Y. Miller, K. A. Roberti and W. E. Timberlake, 1987 Position-dependent and position-independent mechanisms regulate cell-specific expression of the spoc1 gene-cluster of *Aspergillus nidulans*. Molecular and Cellular Biology 7: 427-434.

Miller, B. L., K. Y. Miller and W. E. Timberlake, 1985 Direct and indirect gene replacements in *Aspergillus nidulans*. Molecular and Cellular Biology 5: 1714-1721.

Myung, K., S. J. Li, R. A. E. Butchko, M. Busman, R. H. Proctor et al., 2009 FvVE1 Regulates Biosynthesis of the Mycotoxins Fumonisins and Fusarins in *Fusarium verticillioides*. Journal of Agricultural and Food Chemistry 57: 5089-5094.

Osherov, N., and G. May, 2000 Conidial germination in *Aspergillus nidulans* requires RAS signaling and protein synthesis. Genetics 155: 647-656.

PONTECORVO, G., J. A. ROPER, L. M. HEMMONS, K. D. MACKDONALD, A. W. BUFTON et al., 1953. The genetics of *Aspergillus nidulans*. Adv. Genet. 5: 141-238.

SAMBROOK, J., and D. W. RUSSELL, 2003 Molecular cloning: a laboratory manual, 3rd ed. Cold Spring Harbor Laboratory Press, Cold Spring Harbor, N.Y.

YELTON, M. M., J. E. HAMER, E. R. DESOUZA, E. J. MULLANEY and W. E. TIMBERLAKE, 1983 Developmental regulation of the *Aspergillus nidulans*-Trpc Gene. Proceedings of the National Academy of Sciences 80: 7576-7580.

YU, J. H., R. A. Butchko, M. Fernandes, N. P. Keller, T. J. Leonard, and T. H. Adams. 1996. Conservation of structure and function of the aflatoxin regulatory gene aflR from *Aspergillus nidulans* and *A. flavus*. Curr. Genet. 29: 549-555.

The invention claimed is:

1. A genetically modified fungal strain selected from the strains listed in FIG. 11 wherein the modification is in an mtfA homolog.

2. A method to control expression of secondary metabolites by fungal genes encoding a fungal transcription factor, the method comprising:
   (a) selecting a gene encoding a fungal transcription factor; and
   (b) manipulating expression of the gene in a fungal strain of claim 1 to increase or decrease expression products.

3. The method of claim 2 wherein manipulating is deleting the gene or a part of the gene.

4. The method of claim 2 wherein manipulating is interrupting the coding region of the gene with an insertion.

5. The method of claim 2 wherein the secondary metabolites are selected from the group consisting of mycotoxins and antibiotics.

6. A method to improve production of desirable secondary metabolites during fermentation or reduce undesirable products, the method comprising:
   (a) increasing the production of secondary metabolites by increasing expression of mtfA encoding a fungal transcription factor;
   (b) decreasing the production of undesirable products of fermentation by not expressing a gene encoding a fungal regulator; and
   (c) coordinating expression of the genes in the fungal strain of claim 1 to achieve a predetermined combination of products.

7. The method of claim 6 wherein a desirable secondary metabolite is penicillin.

8. The method of claim 6 wherein an undesirable product is selected from the group consisting of mycotoxin and aflatoxin.

9. The method of claim 2 where the fungal transcription factor is MtfA.

10. A method to increase production of penicillin from a fungus, the method comprising:
    (a) obtaining the fungal strain of claim 1 capable of producing penicillin; and
    (b) causing the fungal strain to overexpress the mtfA gene encoding the MtfA protein.

11. A method to reduce sexual and asexual development of a fungus, the method comprising:
    (a) obtaining the fungus; and
    (b) manipulating expression of the gene encoding MtfA with an insertion or deletion in the gene.

12. A modification of the mtfA genetic locus in a fungal strain of claim 1, wherein the modification is selected from the group consisting of a deletion, alteration and overexpression.

13. A DNA cassette producing the modification of claim 1.

14. The fungal strain of claim 1 selected from the group consisting of TRVΔ mtfA and TRVΔ60.

* * * * *